US010537696B2

(12) United States Patent
Barlow et al.

(10) Patent No.: US 10,537,696 B2
(45) Date of Patent: Jan. 21, 2020

(54) PATIENT INTERFACE SYSTEMS

(71) Applicant: ResMed Pty Ltd, Bella Vista (AU)

(72) Inventors: Adam Francis Barlow, Sydney (AU);
Rupert Christian Scheiner, Sydney (AU); Justin John Formica, Sydney (AU); Aaron Samuel Davidson, Sydney (AU); Kai Stuebiger, Sydney (AU)

(73) Assignee: ResMed Pty Ltd, Bella Vista, NSW (AU)

( * ) Notice: Subject to any disclaimer, the term of this patent is extended or adjusted under 35 U.S.C. 154(b) by 0 days.

(21) Appl. No.: 16/205,714

(22) Filed: Nov. 30, 2018

(65) Prior Publication Data

US 2019/0091433 A1    Mar. 28, 2019

Related U.S. Application Data

(63) Continuation of application No. 16/204,912, filed on Nov. 29, 2018, now Pat. No. 10,449,317, which is a
(Continued)

(51) Int. Cl.
*A61M 16/06* (2006.01)
*A61M 16/08* (2006.01)
(Continued)

(52) U.S. Cl.
CPC .... *A61M 16/0666* (2013.01); *A61M 16/0057* (2013.01); *A61M 16/06* (2013.01);
(Continued)

(58) Field of Classification Search
CPC ....... A61B 5/097; A61B 5/6819; A61B 5/682; A61M 16/0057; A61M 16/0066;
(Continued)

(56) References Cited

U.S. PATENT DOCUMENTS

| 122,905 A | 1/1872 | O'Dell |
| 1,192,186 A | 7/1916 | Greene |

(Continued)

FOREIGN PATENT DOCUMENTS

| AU | 2009/902524 | 6/2009 |
| AU | 2009/906101 | 12/2009 |

(Continued)

OTHER PUBLICATIONS

ACP Composites—Large Stock of Ready to Use Composite Plate, Tube, Sheet, Fabrics and Core Materials, https://www.acpsakes.com/Core-Materials-nd-Foam.html, dated Oct. 5, 2015, 4 pages.

(Continued)

*Primary Examiner* — Annette Dixon
(74) *Attorney, Agent, or Firm* — Fish & Richardson P.C.

(57) ABSTRACT

A patient interface structure for delivery of respiratory therapy to a patient includes a front plate configured to conform to the shape of the patient's face; a mouth cushion defining a breathing chamber and provided to the front plate and configured to seal around the patient's mouth; and a nasal cushion configured to seal the patient's nasal airways. The nasal cushion is supported by the mouth cushion, does not contact a bridge of the patient's nose in use, and extends at least partially into the breathing chamber. A patient interface system includes a patient interface structure and a patient interface structure positioning system configured to position, stabilize and secure the patient interface structure in sealing engagement with the patient's face.

29 Claims, 95 Drawing Sheets

Related U.S. Application Data continuation of application No. 16/198,492, filed on Nov. 21, 2018, now Pat. No. 10,456,545, which is a continuation of application No. 16/032,722, filed on Jul. 11, 2018, which is a continuation of application No. 14/645,457, filed on Mar. 12, 2015, now Pat. No. 10,052,448, which is a continuation of application No. 13/876,624, filed as application No. PCT/AU2011/001258 on Sep. 30, 2011, now Pat. No. 9,010,330.

(60) Provisional application No. 61/388,357, filed on Sep. 30, 2010, provisional application No. 61/443,623, filed on Feb. 16, 2011, provisional application No. 61/457,981, filed on Jul. 27, 2011, provisional application No. 61/528,524, filed on Aug. 29, 2011.

(51) Int. Cl.
*A61M 16/20* (2006.01)
*A61M 16/00* (2006.01)

(52) U.S. Cl.
CPC .... *A61M 16/0611* (2014.02); *A61M 16/0616* (2014.02); *A61M 16/0622* (2014.02); *A61M 16/0683* (2013.01); *A61M 16/0816* (2013.01); *A61M 16/0825* (2014.02); *A61M 16/0875* (2013.01); *A61M 16/20* (2013.01); *A61M 16/208* (2013.01); *A61M 2202/0225* (2013.01); *A61M 2205/0216* (2013.01); *A61M 2210/0618* (2013.01); *A61M 2210/0625* (2013.01)

(58) Field of Classification Search
CPC .. A61M 16/01; A61M 16/06; A61M 16/0605; A61M 16/0611; A61M 16/0616; A61M 16/0622; A61M 16/0633; A61M 16/0638; A61M 16/0655; A61M 16/0666; A61M 16/0683; A61M 16/0694; A61M 16/0816; A61M 16/0841; A61M 16/0875; A61M 16/10; A61M 16/20; A61M 16/206; A61M 16/209; A61M 2016/0661; A61M 2205/59; A61M 2210/0618; A61M 2210/0625

See application file for complete search history.

(56) References Cited

U.S. PATENT DOCUMENTS

| | | | |
|---|---|---|---|
| 1,229,050 A | 6/1917 | Donald | |
| 1,362,766 A | 12/1920 | Mcgargill | |
| 1,445,010 A | 2/1923 | Feinberg | |
| 1,710,160 A | 2/1925 | Gibbs | |
| 2,126,755 A | 8/1938 | Dreyfus | |
| 2,130,555 A | 9/1938 | Malcom | |
| 2,228,218 A | 1/1941 | Schwartz | |
| 2,578,621 A | 12/1951 | Yant | |
| 2,706,983 A | 4/1955 | Matheson et al. | |
| 3,330,273 A | 7/1967 | Bennett | |
| 3,424,633 A | 1/1969 | Corrigall et al. | |
| 3,682,171 A | 8/1972 | Dali et al. | |
| 4,248,218 A | 2/1981 | Fischer | |
| 4,263,908 A | 4/1981 | Mizerak | |
| 4,537,192 A | 8/1985 | Foster | |
| 4,676,236 A | 6/1987 | Piorkowski et al. | |
| 4,676,241 A | 6/1987 | Webb et al. | |
| 4,782,832 A | 11/1988 | Trimble et al. | |
| 4,919,128 A | 4/1990 | Kopala et al. | |
| 4,944,310 A | 7/1990 | Sullivan | |
| 4,989,596 A | 2/1991 | Macris et al. | |
| 5,005,571 A | 4/1991 | Dietz | |
| 5,042,478 A | 8/1991 | Kopala et al. | |
| 5,062,421 A | 11/1991 | Burns et al. | |
| D322,318 S | 12/1991 | Sullivan | |
| 5,243,971 A | 9/1993 | Sullivan et al. | |
| 5,375,593 A | 12/1994 | Press | |
| 5,513,634 A | 5/1996 | Jackson | |
| 5,560,354 A * | 10/1996 | Berthon-Jones | A61M 16/06 128/204.18 |
| 5,657,752 A | 8/1997 | Landis et al. | |
| 5,662,101 A | 9/1997 | Ogden et al. | |
| 5,724,965 A | 3/1998 | Handke et al. | |
| 5,746,201 A | 5/1998 | Kidd | |
| 5,921,239 A | 7/1999 | McCall et al. | |
| 6,016,804 A | 1/2000 | Gleason et al. | |
| 6,119,694 A | 9/2000 | Correa et al. | |
| 6,123,071 A | 9/2000 | Berthon-Jones et al. | |
| 6,192,886 B1 | 2/2001 | Rudolph | |
| 6,412,488 B1 | 7/2002 | Barnett et al. | |
| 6,418,928 B1 | 7/2002 | Bordewick et al. | |
| 6,431,172 B1 | 8/2002 | Bordewick | |
| 6,435,181 B1 | 8/2002 | Jones, Jr. et al. | |
| 6,457,473 B1 | 10/2002 | Brostrom et al. | |
| 6,467,483 B1 | 10/2002 | Kopacko et al. | |
| 6,478,026 B1 | 11/2002 | Wood | |
| 6,513,526 B2 * | 2/2003 | Kwok | A61B 5/097 128/206.24 |
| 6,530,373 B1 | 3/2003 | Patron et al. | |
| 6,561,190 B1 | 5/2003 | Kwok | |
| 6,581,594 B1 | 6/2003 | Drew et al. | |
| 6,584,975 B1 | 7/2003 | Taylor | |
| 6,631,718 B1 | 10/2003 | Lovell | |
| 6,644,315 B2 | 11/2003 | Ziaee | |
| 6,691,707 B1 | 2/2004 | Gunaratnam et al. | |
| 6,796,308 B2 | 9/2004 | Gunaratnam et al. | |
| 6,823,869 B2 | 11/2004 | Raje et al. | |
| 6,851,425 B2 | 2/2005 | Jaffre et al. | |
| 6,860,270 B2 | 3/2005 | Sniadach | |
| D505,489 S | 5/2005 | Sleeper | |
| 6,907,882 B2 | 6/2005 | Ging et al. | |
| 7,007,696 B2 | 3/2006 | Palkon et al. | |
| 7,152,602 B2 | 12/2006 | Bateman et al. | |
| 7,174,575 B1 | 2/2007 | Scherer | |
| 7,174,893 B2 | 2/2007 | Walker et al. | |
| 7,178,525 B2 | 2/2007 | Matula, Jr. et al. | |
| 7,178,528 B2 | 2/2007 | Lau et al. | |
| 7,210,481 B1 | 5/2007 | Lovell et al. | |
| 7,219,669 B1 | 5/2007 | Lovell et al. | |
| 7,243,650 B2 | 7/2007 | Thornton | |
| 7,353,827 B2 | 4/2008 | Geist | |
| 7,357,136 B2 | 4/2008 | Ho et al. | |
| 7,448,386 B2 * | 11/2008 | Ho | A61M 16/06 128/205.25 |
| 7,509,958 B2 | 3/2009 | Amarasinghe et al. | |
| 7,523,754 B2 | 4/2009 | Lithgow et al. | |
| 7,658,189 B2 | 2/2010 | Davidson et al. | |
| 7,827,990 B1 | 11/2010 | Melidis et al. | |
| 7,909,035 B2 | 3/2011 | Thornton | |
| 8,028,699 B2 | 10/2011 | Ho et al. | |
| 8,042,538 B2 | 10/2011 | Ging et al. | |
| 8,042,539 B2 | 10/2011 | Chandran et al. | |
| 8,402,971 B2 | 3/2013 | Scheiner et al. | |
| 8,443,807 B2 | 5/2013 | McAuley et al. | |
| 8,479,741 B2 | 7/2013 | McAuley et al. | |
| 8,550,084 B2 | 10/2013 | Ng et al. | |
| 8,714,157 B2 | 5/2014 | McAuley et al. | |
| 8,944,061 B2 | 2/2015 | D'Souza et al. | |
| 8,950,404 B2 | 2/2015 | Formica et al. | |
| 8,960,196 B2 | 2/2015 | Henry | |
| 9,010,330 B2 | 4/2015 | Barlow et al. | |
| 9,027,556 B2 | 5/2015 | Ng et al. | |
| 9,119,931 B2 | 9/2015 | D'Souza et al. | |
| 9,242,062 B2 | 1/2016 | Melidis et al. | |
| 9,333,315 B2 | 5/2016 | McAuley et al. | |
| 9,381,316 B2 | 7/2016 | Ng et al. | |
| 9,517,317 B2 | 12/2016 | McAuley et al. | |
| 9,539,405 B2 | 1/2017 | McAuley et al. | |
| 9,907,922 B2 | 3/2018 | Stephenson et al. | |
| 9,907,923 B2 | 3/2018 | Stephenson et al. | |
| 9,974,914 B2 | 5/2018 | McAuley et al. | |
| 2002/0020416 A1 | 2/2002 | Namey | |
| 2002/0029780 A1 | 3/2002 | Frater et al. | |

(56) References Cited

U.S. PATENT DOCUMENTS

| | | |
|---|---|---|
| 2002/0134388 A1 | 9/2002 | Chang |
| 2003/0029454 A1 | 2/2003 | Gelinas et al. |
| 2003/0145859 A1* | 8/2003 | Bohn ............ A61M 16/06 128/206.24 |
| 2003/0196655 A1 | 10/2003 | Ging et al. |
| 2003/0196658 A1 | 10/2003 | Ging et al. |
| 2004/0025882 A1 | 2/2004 | Madaus et al. |
| 2004/0041342 A1 | 3/2004 | Frieman |
| 2004/0067333 A1 | 4/2004 | Amarasinghe |
| 2004/0118406 A1 | 6/2004 | Lithgow et al. |
| 2004/0182398 A1 | 9/2004 | Sprinkle et al. |
| 2004/0211428 A1 | 10/2004 | Jones, Jr. et al. |
| 2004/0226566 A1 | 11/2004 | Gunaratnam et al. |
| 2004/0255949 A1 | 12/2004 | Lang et al. |
| 2005/0001152 A1 | 1/2005 | Stewart et al. |
| 2005/0011524 A1 | 1/2005 | Thomlinson et al. |
| 2005/0028822 A1 | 2/2005 | Sleeper et al. |
| 2005/0121030 A1 | 6/2005 | Bateman et al. |
| 2005/0155604 A1 | 7/2005 | Ging et al. |
| 2005/0199240 A1 | 9/2005 | Hall |
| 2006/0042629 A1 | 3/2006 | Geist |
| 2006/0060200 A1 | 3/2006 | Ho et al. |
| 2006/0112962 A1 | 6/2006 | Tebbutt et al. |
| 2006/0118117 A1 | 6/2006 | Berthon-Jones et al. |
| 2006/0124131 A1 | 6/2006 | Chandran et al. |
| 2006/0174887 A1 | 8/2006 | Chandran et al. |
| 2006/0201514 A1 | 9/2006 | Jones et al. |
| 2006/0207597 A1 | 9/2006 | Wright |
| 2006/0237017 A1 | 10/2006 | Davidson et al. |
| 2006/0272646 A1 | 12/2006 | Ho et al. |
| 2007/0006879 A1 | 1/2007 | Thornton |
| 2007/0044804 A1 | 3/2007 | Matula, Jr. et al. |
| 2007/0125384 A1* | 6/2007 | Zollinger ............ A61M 16/06 128/206.24 |
| 2007/0125385 A1 | 6/2007 | Ho et al. |
| 2007/0175480 A1 | 8/2007 | Gradon et al. |
| 2007/0186930 A1 | 8/2007 | Davidson et al. |
| 2008/0006277 A1 | 1/2008 | Worboys et al. |
| 2008/0110464 A1 | 5/2008 | Davidson et al. |
| 2008/0110466 A1 | 5/2008 | Armitstead |
| 2009/0032026 A1 | 2/2009 | Price et al. |
| 2009/0038619 A1 | 2/2009 | Ho et al. |
| 2009/0044808 A1 | 2/2009 | Guney et al. |
| 2009/0050156 A1 | 2/2009 | Ng et al. |
| 2009/0078259 A1 | 3/2009 | Kooij et al. |
| 2009/0114229 A1 | 5/2009 | Frater et al. |
| 2009/0159084 A1* | 6/2009 | Sher ............ A61M 16/06 128/205.24 |
| 2009/0277452 A1 | 11/2009 | Lubke et al. |
| 2010/0139662 A1 | 6/2010 | Chang |
| 2010/0313891 A1 | 12/2010 | Veliss et al. |
| 2011/0056497 A1 | 3/2011 | Scheiner et al. |
| 2011/0072553 A1 | 3/2011 | Ho |
| 2013/0213400 A1 | 8/2013 | Barlow et al. |
| 2014/0083430 A1 | 3/2014 | Matula, Jr. et al. |
| 2015/0090602 A1 | 4/2015 | Sato et al. |
| 2016/0074613 A1 | 3/2016 | Davidson et al. |
| 2018/0318540 A1 | 11/2018 | Barlow et al. |

FOREIGN PATENT DOCUMENTS

| | | |
|---|---|---|
| AU | 2010/902359 | 5/2010 |
| CN | 1919376 | 2/2007 |
| CN | 101237902 | 8/2008 |
| CN | 101252965 | 8/2008 |
| DE | 4004157 | 4/1991 |
| GB | 2385533 | 8/2003 |
| JP | 2011-104096 | 6/2011 |
| WO | WO 00/50122 | 8/2000 |
| WO | WO 2002/047749 | 6/2002 |
| WO | WO 2003/076020 | 9/2003 |
| WO | WO 2004/022147 | 3/2004 |
| WO | WO 2004/041341 | 5/2004 |
| WO | WO 2004/041342 | 5/2004 |
| WO | WO 2004/052438 | 6/2004 |
| WO | WO 2004/073778 | 9/2004 |
| WO | WO 2005/021075 | 3/2005 |
| WO | WO 2005/051468 | 6/2005 |
| WO | WO 2005/063328 | 7/2005 |
| WO | WO 2005/079726 | 9/2005 |
| WO | WO 2005/123166 | 12/2005 |
| WO | WO 2006/000046 | 1/2006 |
| WO | WO 2006/000770 | 1/2006 |
| WO | WO 2006/074515 | 7/2006 |
| WO | WO 2006/130903 | 12/2006 |
| WO | WO 2007/006089 | 1/2007 |
| WO | WO 2007/008725 | 1/2007 |
| WO | WO 2007/014088 | 2/2007 |
| WO | WO 2007/041751 | 4/2007 |
| WO | WO 2007/045008 | 4/2007 |
| WO | WO 2007/048174 | 5/2007 |
| WO | WO 2007/130067 | 11/2007 |
| WO | WO 2007/133332 | 11/2007 |
| WO | WO 2007/139531 | 12/2007 |
| WO | WO 2007/147088 | 12/2007 |
| WO | WO 2008/007985 | 1/2008 |
| WO | WO 2008/030831 | 3/2008 |
| WO | WO 2008/068966 | 6/2008 |
| WO | PCT/AU2008/906390 | 12/2008 |
| WO | PCT/AU2009/900327 | 1/2009 |
| WO | WO 2009/026627 | 3/2009 |
| WO | WO 2009/052560 | 4/2009 |
| WO | WO 2009/059353 | 5/2009 |
| WO | PCT/AU2009/902731 | 6/2009 |
| WO | PCT/AU2009/904236 | 9/2009 |
| WO | WO 2009/108995 | 9/2009 |
| WO | WO 2012/040792 | 4/2010 |
| WO | WO 2010/066004 | 6/2010 |
| WO | WO 2010/135785 | 12/2010 |
| WO | WO 2010/139014 | 12/2010 |
| WO | WO 2012/040791 | 4/2012 |

OTHER PUBLICATIONS

Extended Search Report dated Mar. 31, 2017 issued in European Application No. 11827828.2 (8 pages).
First Examination Report dated May 9, 2017 issued in New Zealand Application No. 728600 (2 pages).
First Examination Report dated Nov. 9, 2015 issued in New Zealand Application No. 713455 (2 pages).
First Examination Report issued in corresponding New Zealand Application No. 625429, dated Jun. 18, 2014.
Flexifit instructions, http://web.archive.org/web/1 9970126045828/ http:/www.archive.org/ dated Jan. 26, 1997, Affidavit of Christopher Butler dated Sep. 6, 2016, 23 pages.
Further Examination Report dated Dec. 13, 2016 issued in New Zealand Application No. 713455 (2 pages).
Further Examination Report dated Sep. 18, 2017 issued in New Zealand Application No. 728600 (3 pages).
Guidelines for Sandwich Core Materials, http://fibreglast.com/ product/guidelines-for-sandwich-core-materials/Learning_Center, dated Oct. 5, 2015, 3 pages.
International Search Report for PCT/AU2011/001258 dated Dec. 13, 2011.
Malloy, Plastic Part Design for Injection Molding, New York: Hanser Publishers, 1994, 14 pages.
Notice of Allowance dated Jan. 23, 2017 issued in Japanese Application No. 2013-530493 (3 pages).
Notice of Reasons for Rejection dated Aug. 3, 2015 issued in Chinese Application No. 2013-530493 with English translation (8 pages).
Notification of First Office Action dated Nov. 4, 2014 issued in Chinese Application No. 201180047871.3.
Notification of Second Office Action dated Apr. 10, 2015 issued in Chinese Application No. 201180047871.3 with English translation (26 pages).
Notification of Third Office Action dated Oct. 10, 2015 issued in Chinese Application No. 201180047871.3 with English language translation (22 pages).

(56) References Cited

OTHER PUBLICATIONS

Office Action dated Jun. 29, 2018 issued in European Application No. 11827828.2 (4 pages).
Office Action dated May 9, 2016 issued in Japanese Application No. 2013-530493 with English Translation (6 pages).
Opus Brochure, Fisher & Paykel Healthcare, www.fphcare.com, 2 pages, 2004.
ResMed Mask Frames, Nasal Cushions and Headgear, http://web.archive.org/web/19970 1 26045828 /http ://www.a rchive.org/ dated Jan. 26, 1997, Affidavit of Christopher Butler dated Jul. 6, 2017, 8 pages.
ResMed Mirage Swift Nasal Pillows System, www.resmed.com, 2004, 6 pages.
ResMed Mirage Vista Nasal Mask-Component Cards, www.resmed.com Reference No. 1010279/30502, dated 2005, 1 page.
ResMed Origins Brochure dated Apr. 17, 2016, 64 pages.
Ultra Mirage Full Face Mask brochure, http://web.archive.org/web/19970 126045828/http://www.archive.org/ dated Jan. 26, 1997, Affidavit of Christopher Butler dated Sep. 6, 2016, 9 pages.
Users Guide ResMed Mirage Swift Nasal Pillows System, www.myresmed.com dated May 6, 2004, 11 pages.

* cited by examiner

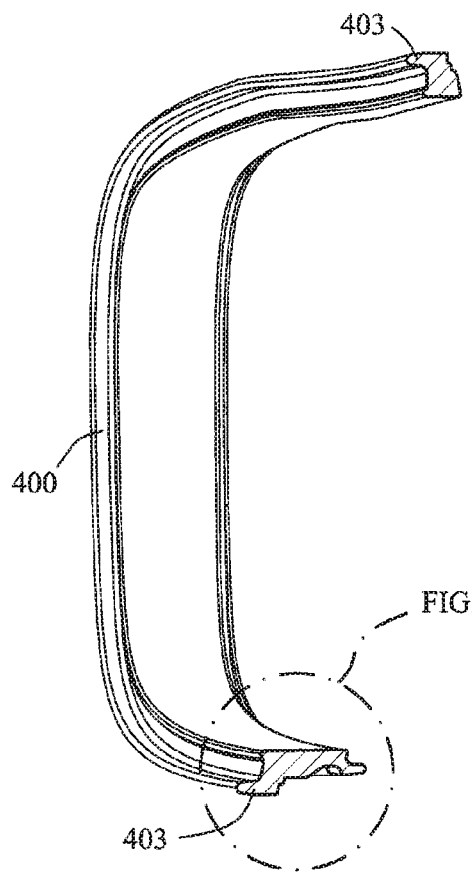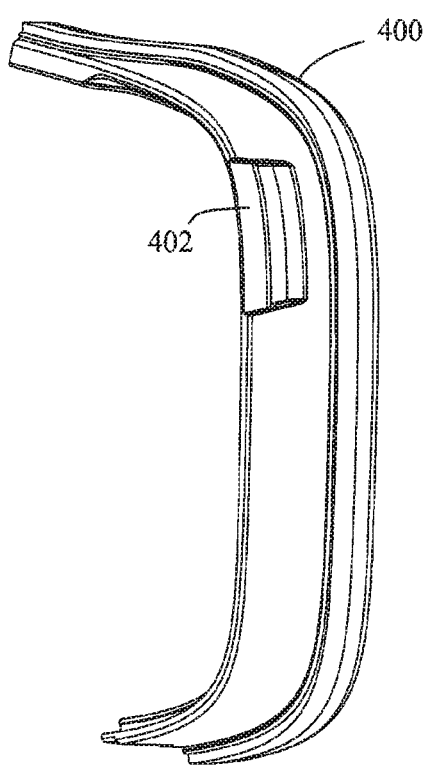
FIG. 125  FIG. 126
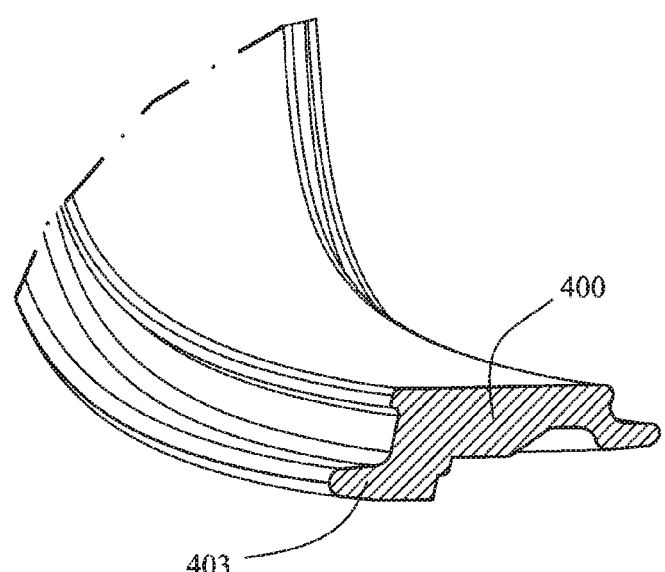
FIG. 127

PATIENT INTERFACE SYSTEMS

CROSS REFERENCE TO RELATED APPLICATIONS

This application is a continuation of U.S. application Ser. No. 16/204,912 filed Nov. 29, 2018, which is a continuation of U.S. application Ser. No. 16/198,492 filed Nov. 21, 2018, which is a continuation of U.S. application Ser. No. 16/032,722, filed Jul. 11, 2018, which is a continuation of U.S. application Ser. No. 14/645,457, now U.S. Pat. No. 10,052,448, filed Mar. 12, 2015, which is a continuation of U.S. application Ser. No. 13/876,624, now U.S. Pat. No. 9,010,330, filed Mar. 28, 2013, which is the U.S. national phase of International Application No. PCT/AU2011/001258 filed 30 Sep. 2011 which designated the U.S. and claims the benefit of U.S. Provisional Applications 61/388,357, 61/443,623, 61/457,981, and 61/528,524, filed Sep. 30, 2010, Feb. 16, 2011, Jul. 27, 2011, and Aug. 29, 2011, respectively, the entire contents of each being incorporated herein by reference in its entirety.

FIELD OF THE INVENTION

The present technology relates to a patient interface, or mask, system for treatment of sleep disordered breathing (SDB).

BACKGROUND

Treatment of sleep disordered breathing (SDB), such as obstructive sleep apnea (OSA), by continuous positive airway pressure (CPAP) flow generator systems involves the continuous delivery of air (or other breathable gas) pressurized above atmospheric pressure to the airways of a human via a conduit and a mask. Typically, the mask fits over or in the mouth and/or nose of the patient. Pressurized air flows to the mask and to the airways of the patient via the nose and/or mouth. Pressurized air is delivered to the mask by a conduit connected to the CPAP device and the mask.

The mask should be comfortable and unobtrusive so that a patient may tolerate therapy and maintain usage. Some patients may prefer a pillows or prongs type mask (as known in the art), or a nasal mask or a full face mask. Some patient's may prefer to use one or a combination of these masks interchangeably. However, this would require the purchase of a number of different mask systems, which may be expensive and/or may not be covered by insurance.

In addition, masks including oro-nasal masks typically include a rigid frame. Patients may not find this comfortable. The frame may also dislodge the sealing portion of the mask away from the face of the patient if it is contacted or forced by bed clothing, pillows, etc.

BRIEF SUMMARY

One aspect of the present technology relates to patent interface, or mask, systems that provide integrated nose and mouth seals that are less obtrusive than currently available systems.

Another aspect of the present technology relates to patient interface systems that have reduced part counts compared to currently available systems.

A further aspect of the present technology relates to patient interface systems, for example oro-nasal masks, that provide a visible mouth region of the patient.

Still another aspect of the present technology relates to patient interface systems, for example oro-nasal masks, that do not obstruct the patient's line of sight.

Further aspects of the present technology relate to patient interface systems, for example oro-nasal masks, that are easier and/or more intuitive to assemble, fit, and use by patients, dealers, and clinicians, and provide improved fitting and sealing.

Yet another aspect of the present technology relates to patient interface systems, for example oro-nasal masks, that provide size selection from remote locations, and without assistance and/or instruction.

Another aspect of the present technology relates to patient interface systems, for example oro-nasal masks, that are considered physiologically non-threatening and will increase patient selection of the system and adherence to therapy.

Further aspects of the present technology relate to patient interface systems, for example oro-nasal masks, that seal the mouth and nasal airways but have no nasal bridge touch points and/or fewer total points of contacts with the patient's face than current systems.

Another aspect of the present technology relates to patient interface systems, for example oro-nasal masks, that comprises a substantially planar fascia that may provide a visible mouth region of the patient.

Another aspect of the present technology relates to patient interface systems, for example oro-nasal masks, that comprises a substantially curved and/or smooth fascia that may provide a visible mouth region of the patient.

Another aspect of the present technology relates to patient interface systems, for example oro-nasal masks, that comprises a substantially curved and/or smooth fascia that may have no ridges, connector portions or other obstructions in the region of the patient's mouth, so that the fascia may provide a visible mouth region of the patient.

Another aspect of the present technology relates to patient interface systems, for example oro-nasal masks, that comprises a substantially smooth fascia that may have no complex shapes, connector portions or other obstructions in the region of the patient's mouth, so that the fascia may provide a visible mouth region of the patient.

Another aspect of the present technology relates to patient interface systems, for example oro-nasal masks, that comprises an air delivery tube connection, the air delivery tube connection positioned on the cushion.

Another aspect of the present technology relates to patient interface systems, for example oro-nasal masks, that comprises an air delivery tube connection, the air delivery tube connection positioned on the fascia and offset from the centre of the fascia, that may provide a visible mouth region of the patient.

Another aspect of the present technology relates to patient interface systems, for example oro-nasal masks, that are substantially comprised of flexible components.

Another aspect of the present technology relates to patient interface systems, for example oro-nasal masks, that are stabilised at the nose sealing portion separately to the mouth sealing portion.

A patient interface structure for delivery of respiratory therapy to a patient according to an example embodiment of the present technology comprises a front plate configured to conform to the shape of the patient's face; a mouth cushion defining a breathing chamber and provided to the front plate and configured to seal around the patient's mouth; and a nasal cushion configured to seal the patient's nasal airways, wherein the nasal cushion is supported by the mouth cushion, does not contact a bridge of the patient's nose in use, and extend at least partially into the breathing chamber.

A patient interface structure for delivery of respiratory therapy to a patient according to an example embodiment of the present technology comprises a front plate configured to conform to the shape of the patient's face; a mouth cushion defining a breathing chamber and provided to the front plate and configured to seal around the patient's mouth; and a nasal cushion configured to seal the patient's nasal airways, wherein the nasal cushion is supported by the mouth cushion, does not contact a bridge of the patient's nose in use, and is raised above the breathing chamber.

A patient interface system according to an example embodiment of the present technology comprises a patient interface structure according to the present technology and a patient interface structure positioning system configured to position, stabilize and secure the patient interface structure in sealing engagement with the patient's face.

A patient interface system according to an example embodiment of the present technology comprises a cushion adapted to sealingly engage with a patient's airways, the cushion comprising a slot adapted to receive a headgear connecting portion of a fascia.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various embodiments of this technology. In such drawings, in which like reference symbols indicate like features:

FIG. 125 is a cross section view of the cushion clip along line 125-125 in FIG. 124;

FIG. 126 is a left side view of the cushion clip;

FIG. 127 is a detailed view of FIG. 125;

DETAILED DESCRIPTION OF ILLUSTRATED EMBODIMENTS

Figure 1:
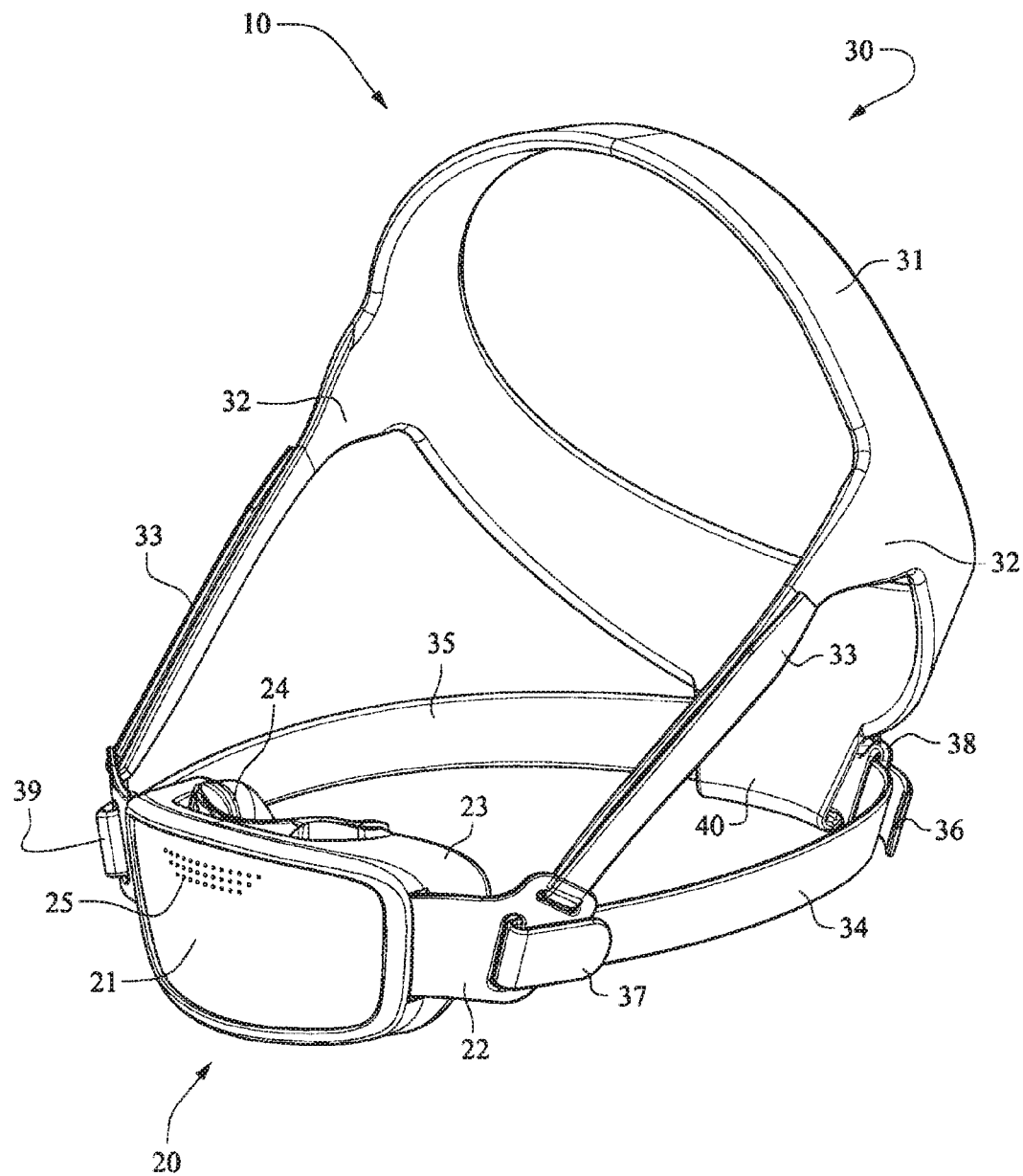
FIGS. 1-6 are front isometric, front, rear, left, right, and bottom views, respectively, of an example embodiment of a patient interface system according to the present technology.
Figure 2:
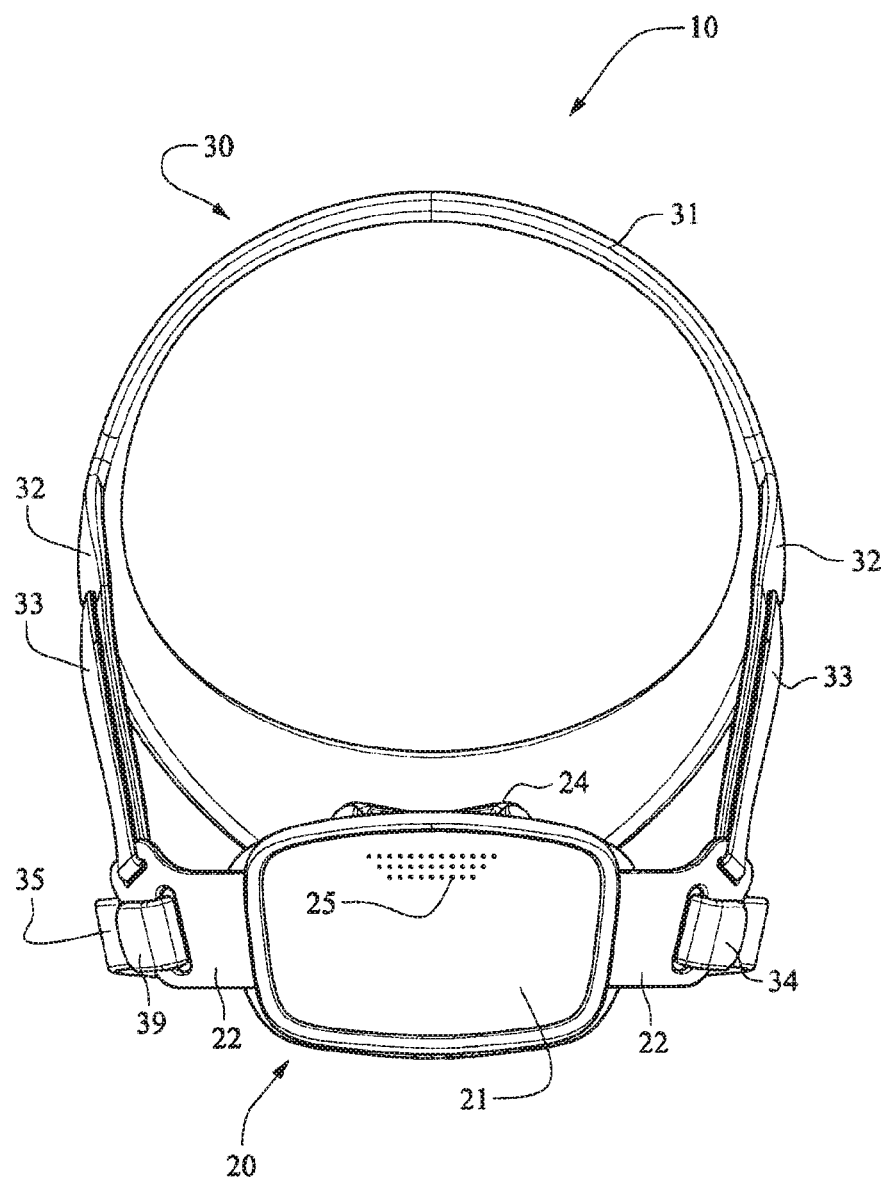
Figure 3:
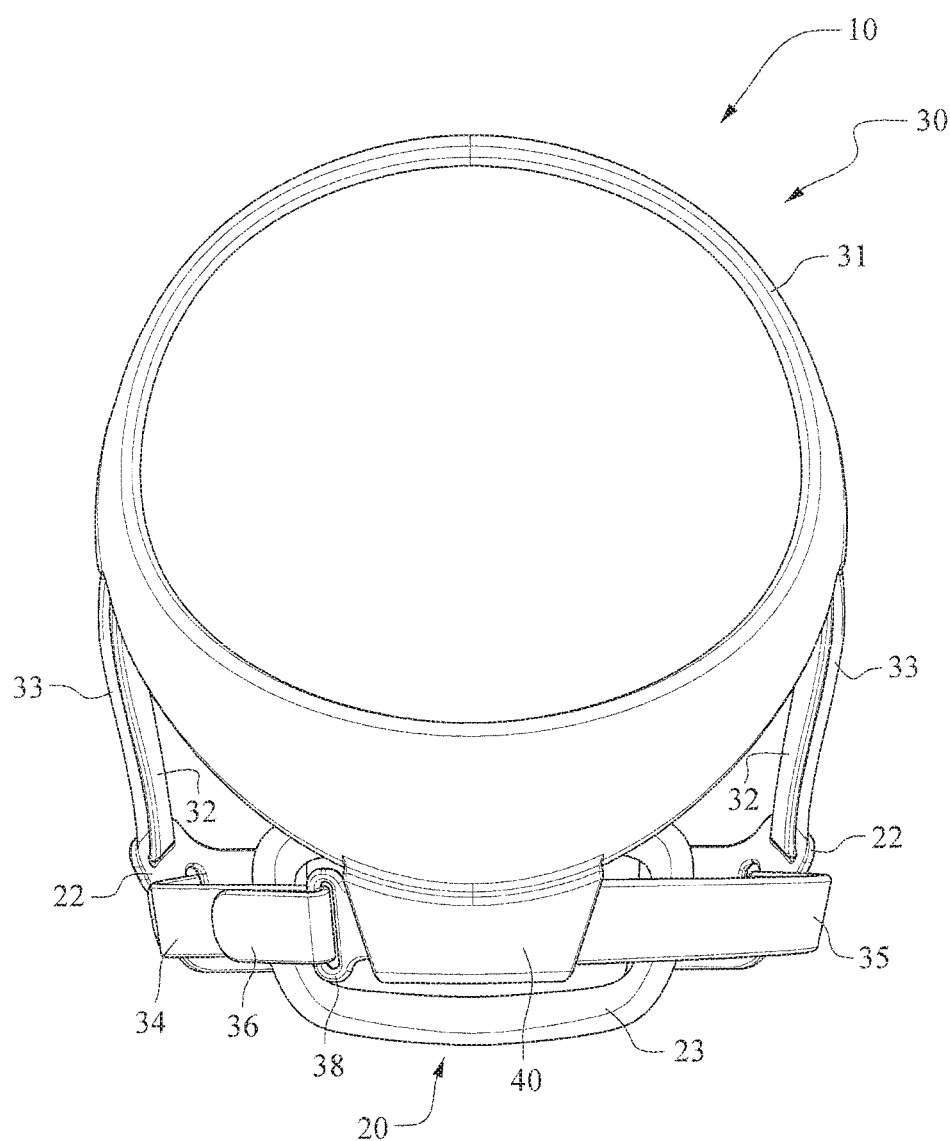
Figure 4:
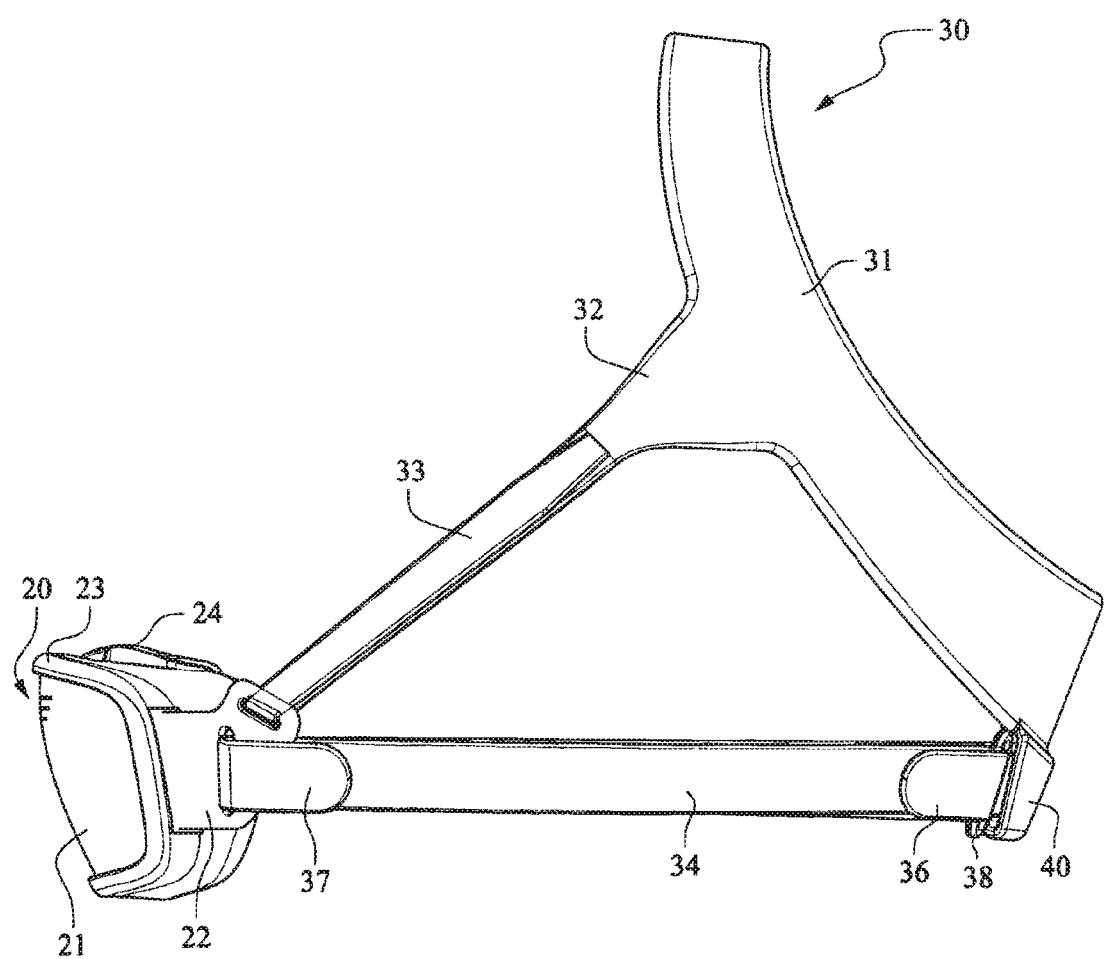
Figure 5:
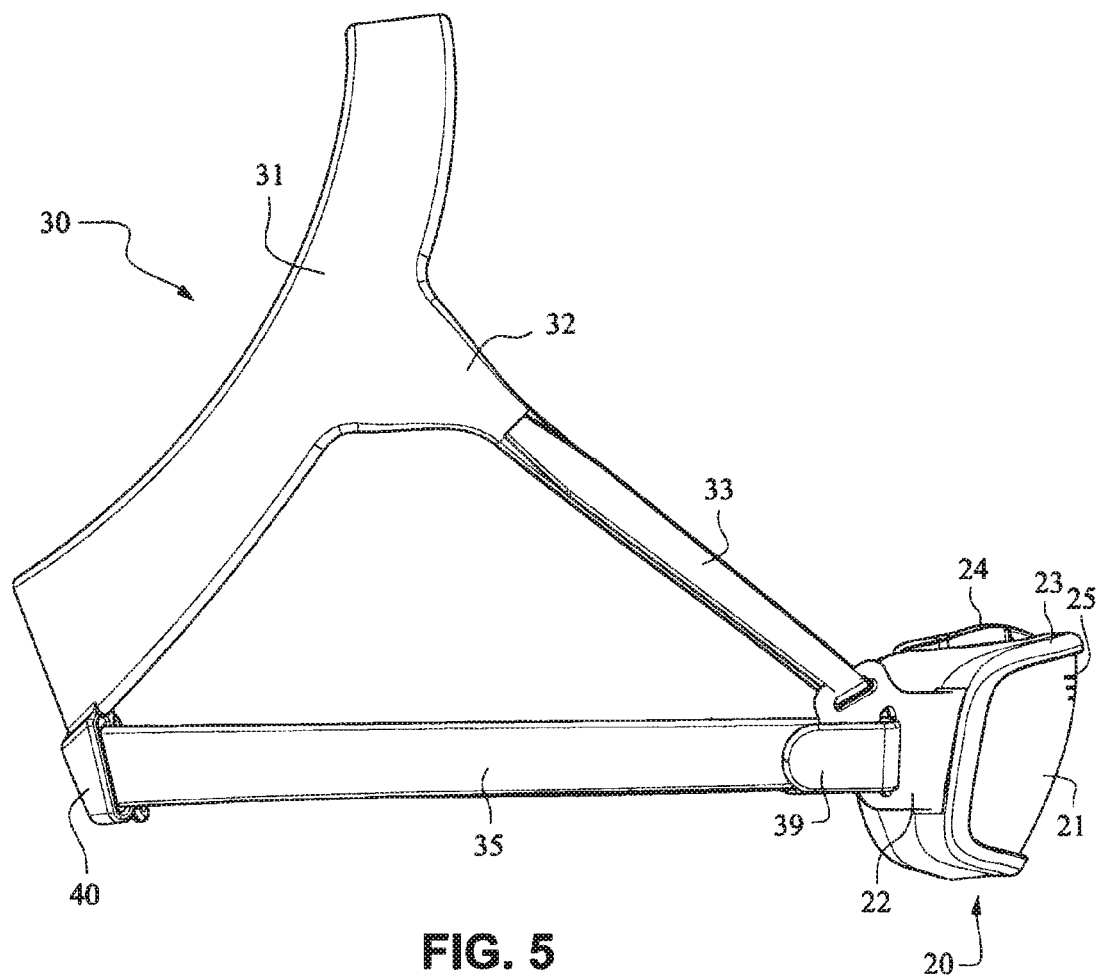
Figure 6:
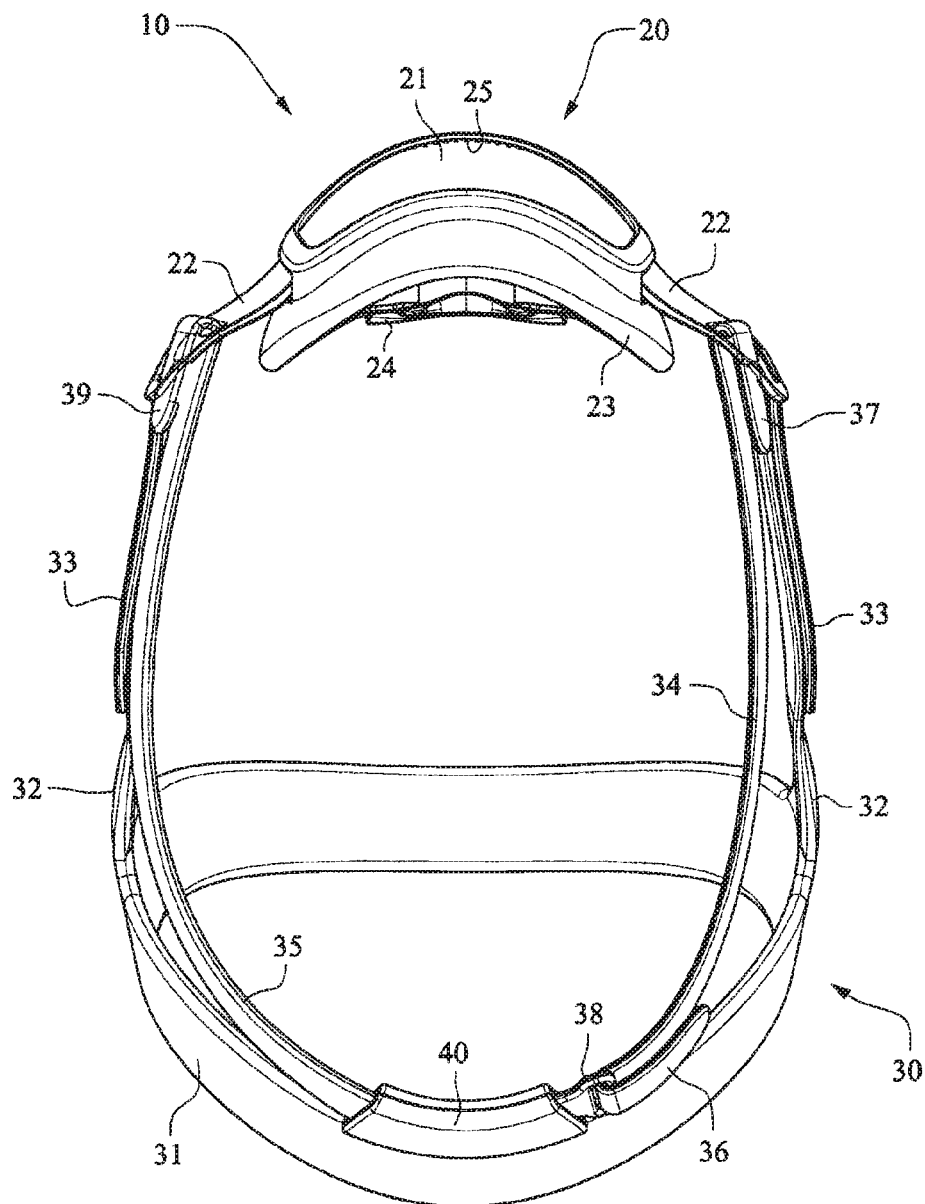
Figure 7:
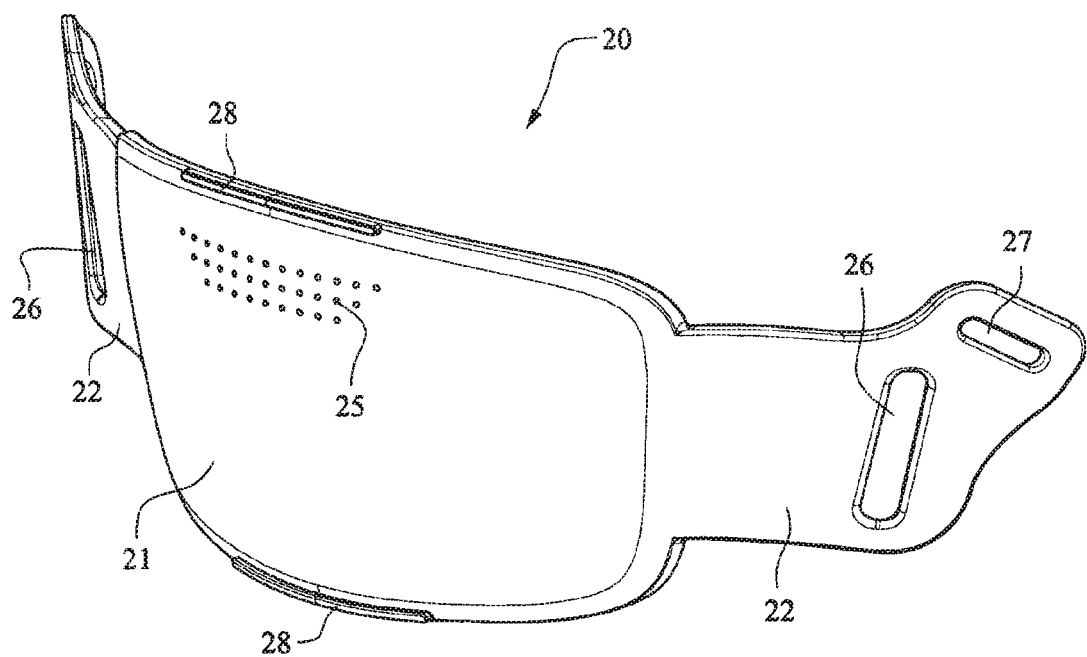
FIGS. 7-13 are front isometric, front, rear, top, bottom, right and left side views, respectively, of a fascia, or front plate, of the patient interface system of FIGS. 1-6.
Figure 8:
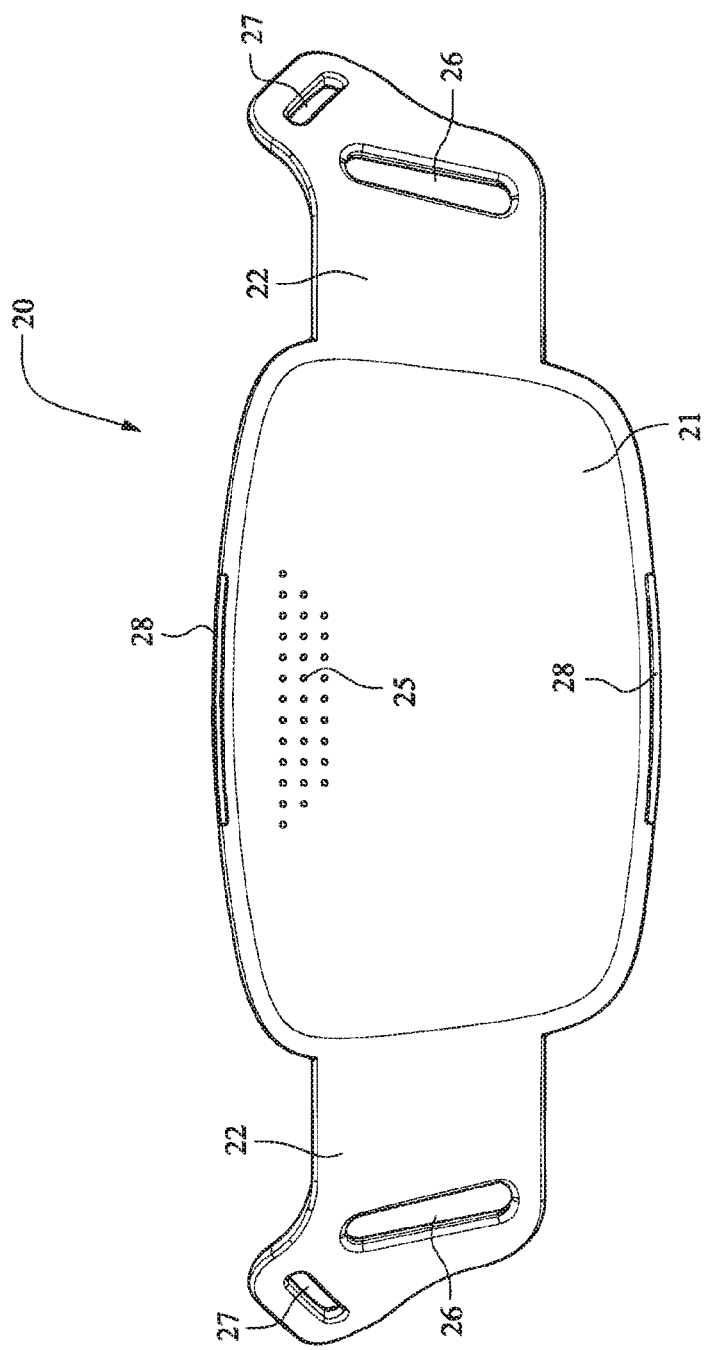
Figure 9:
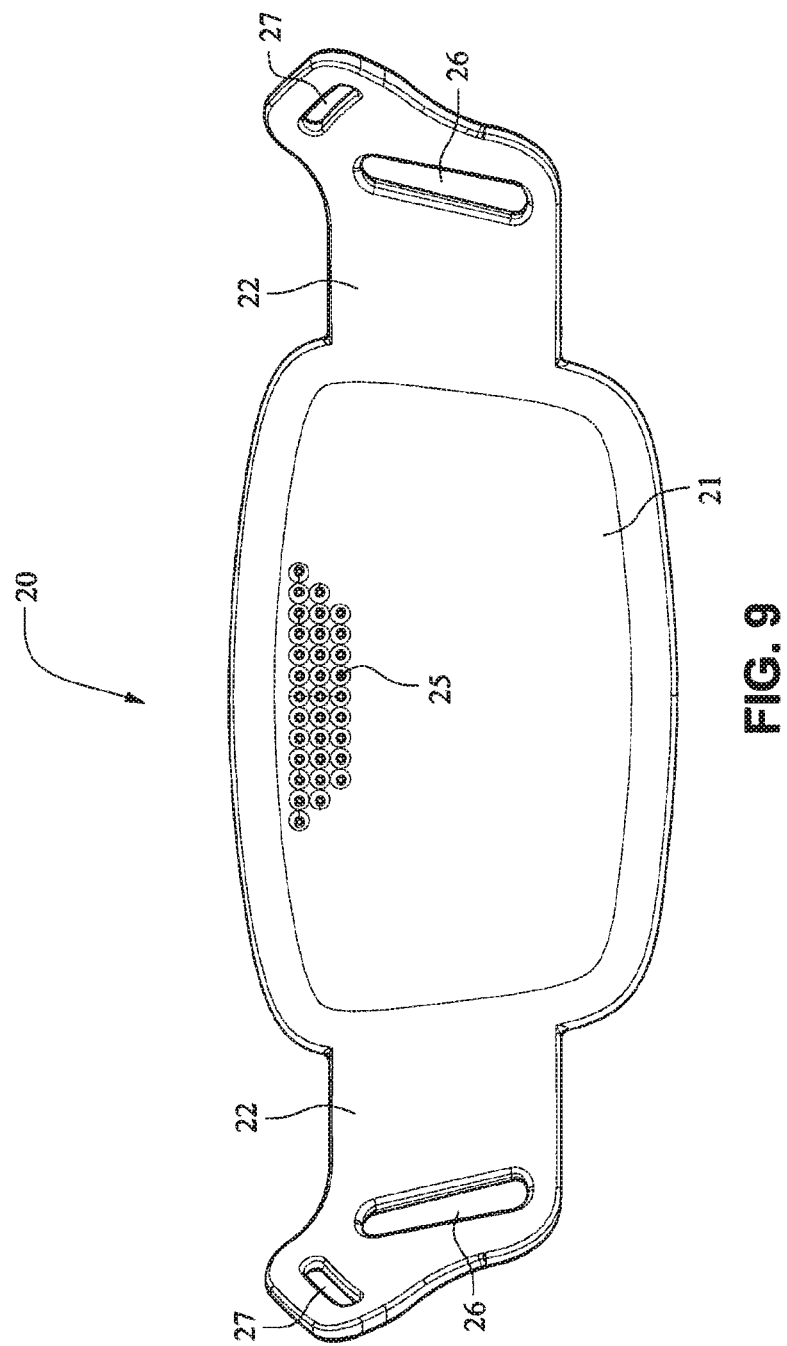
Figure 10:
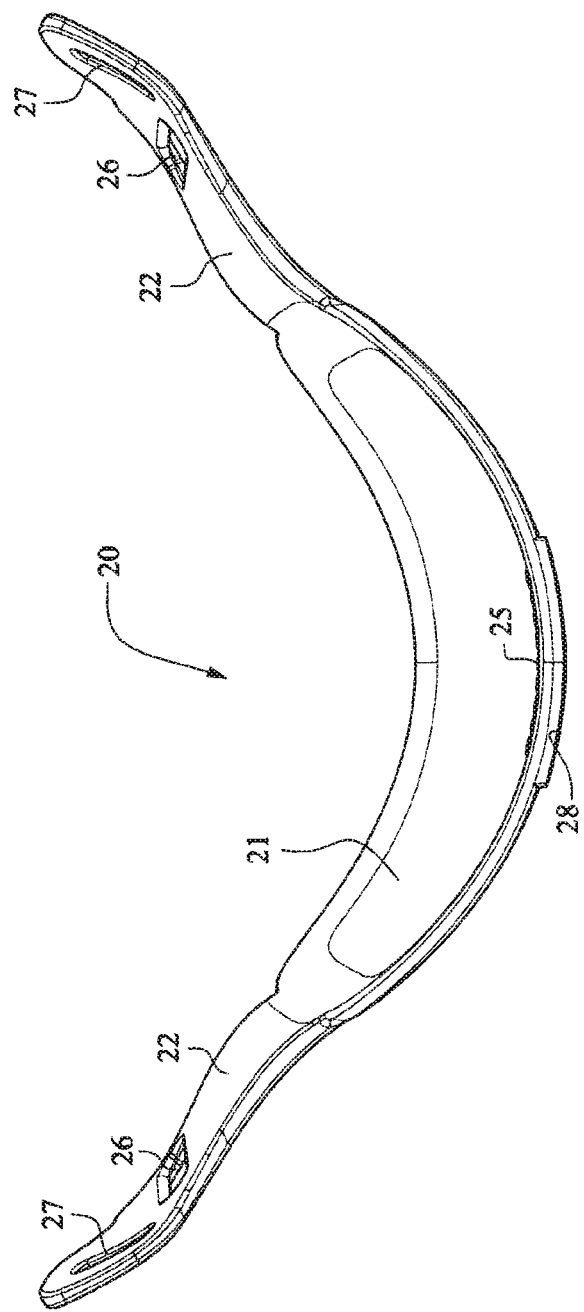
Figure 11:
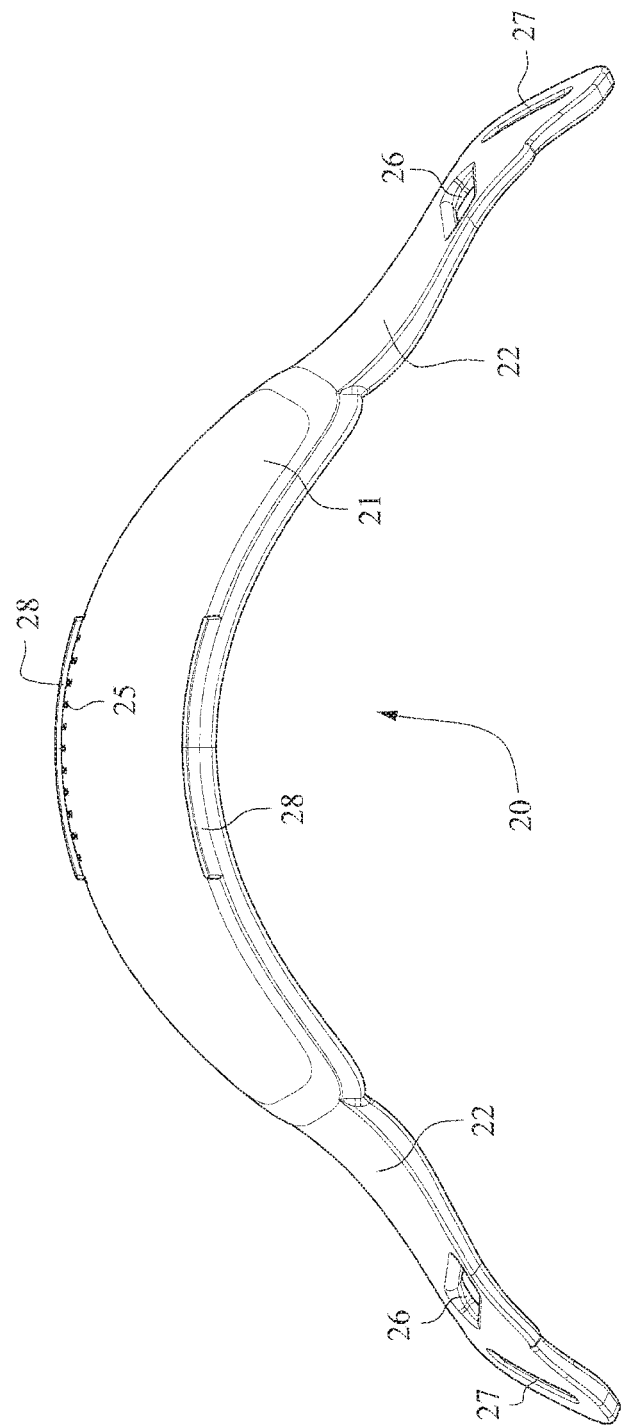
Figure 12:
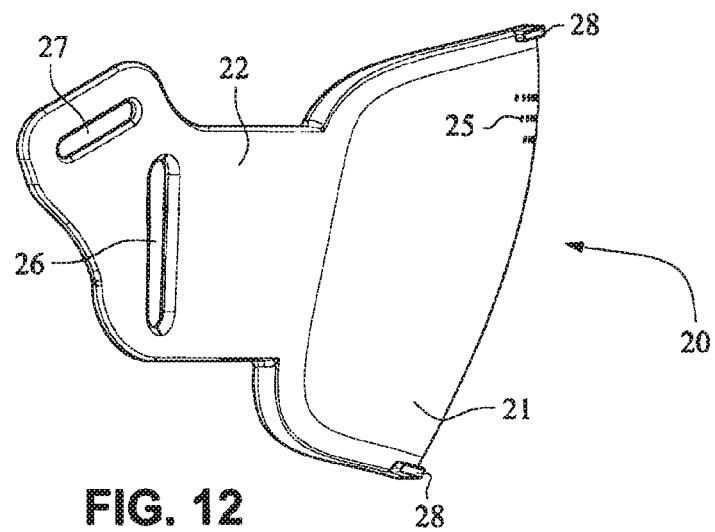
Figure 13:
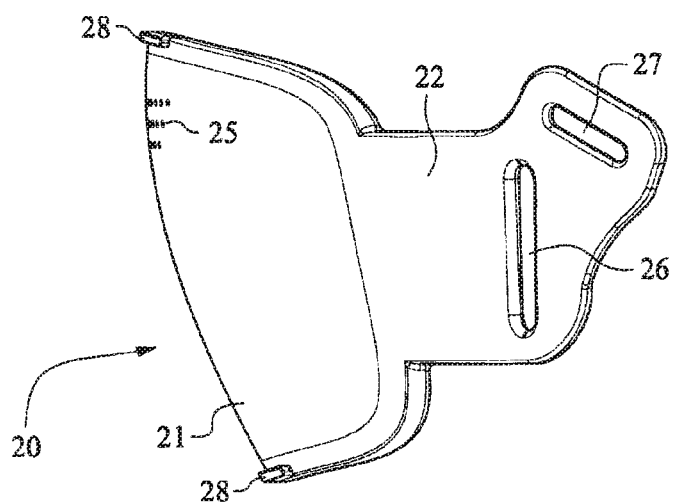

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

Patient Interface Systems

Referring to FIGS. 1-13 and 56-62, a patient interface system or mask system 10 in accordance with an example embodiment of the present technology comprises a patient interface structure or mask structure 20 that is positioned, stabilized and secured on a patient's head in sealing engagement with the patient's mouth and nasal airways by a patient interface positioning system 30, e.g. a headgear. The patient interface structure 20 comprises a fascia or lens or front plate or frame 21 having a mouth seal, or cushion 23 that is connected to the front plate 21. The front plate 21 includes patient interface positioning system connectors 22 (e.g. headgear connectors) to connect the patient interface positioning system (e.g. headgear) 30 to the patient interface structure (e.g. mask) 20. The patient interface structure further comprises a nasal seal, or cushion 24 connected to the mouth seal, or cushion 23 to seal the patient's nasal airways. A vent (e.g., vent holes) 25 may be provided in the front plate 21 to vent exhaled gases in a breathing chamber defined by the front plate 21, the mouth cushion 23 and the nasal cushion 24. The vents may be provided in the front plate 21 proximate the nares and/or mouth of the patient to improve $CO_2$ washout. The array of vent holes 25 may be laser cut, molded or otherwise formed in an upper region of front plate 21.

Patient Interface Positioning System

The patient interface positioning system 30 comprises a crown strap 31 adapted to cup or encircle the crown of the patient's head. Top, or upper side straps 32 extend from the crown strap 31 and connect to the front plate 21 through slots 27. The ends 33 of the top side straps 32 may be looped through the slots 27 and connect to the top side straps 32 by, for example, hook and loop material. It should also be appreciated that other connections, for example buckles, may be used to secure the ends 33 of the top side straps 32. The top side straps 32 may be thickened or widened at the region where they connect to the crown strap 31 to allow ends 33 a larger space to connect to and also a range of angles to position ends 33 relative to slots 27, thereby improving the fit range of the headgear 30. Such an arrangement may also improve comfort and/or to assist in stabilizing and positioning the top side straps 32 on the patient's cheek bone regions.

The crown strap 31 may further comprise a loop 40 through which a right bottom, or lower side strap 35 may pass and connect to a left bottom, or lower side strap 34. It should also be appreciated that the loop may be formed in the lower strap(s) 34 and/or 35, for example as shown in U.S. Applications 61/443,623 and 61/457,981, each of which is incorporated by reference herein in its entirety. It should further be appreciated that other headgear may be used with the patient interface system, for example as disclosed in U.S. Patent Application Publication 2008/0110466 A1, the entire contents of which are incorporated herein by reference. The bottom right side strap 35 may comprise a first end 38 in the form of a loop or slot and a first end 36 of the bottom left side strap 34 may connect to the first end 38 by passing through the loop or slot and connecting through hook and loop material or buckles or other connectors. The second end 37 of the bottom left side strap 34 and the second end 39 of the bottom right side strap 35 may be connected to the front plate 21 through slots 26 in the connectors 22.

Headgear 30 may be formed from a composite e.g. fabric and foam, which may be flame laminated and may be ultrasonically die cut or welded along its edge to create a rounded, more comfortable edge.

Front Plate/Fascia/Lens

The front plate 21 is configured to conform to or accommodate the shape of the patient's face. The front plate 21 may be flexible to allow the front plate to follow the shape of the patient's face. The front plate 21 may be formed of, for example, a flexible polymer that is able to bend and conform around the patient's mouth once the front plate 21 is connected to the patient interface positioning system 30 and fitted to the patient. The front plate 21 may also be malleable to allow the front plate to conform to the shape of the patient's face. A rib(s) 28 may be provided to the front plate 21. The ribs 28 may be provided along the top and bottom of the front plate 21 and aid in alignment and engagement with the cushion 23, as well as providing strength to the fascia.

Front plate 21 may be substantially planar, curved and/or smooth. Masks known in the art tend to include complex shapes and/or structures on the frame, and these complex shapes and/or structures make it difficult to see the patient's mouth clearly and to clean the frame. For example, these complex shapes and/or structures may include elbows, elbow connectors, ports, ridges, contours, headgear connectors, etc. Front plate 21 is adapted to be substantially smooth and without complex shapes or structures i.e. having a substantially planar surface in the region of the patient's mouth, to act as a window to permit clear visibility to the patient's mouth.

Figure 14:
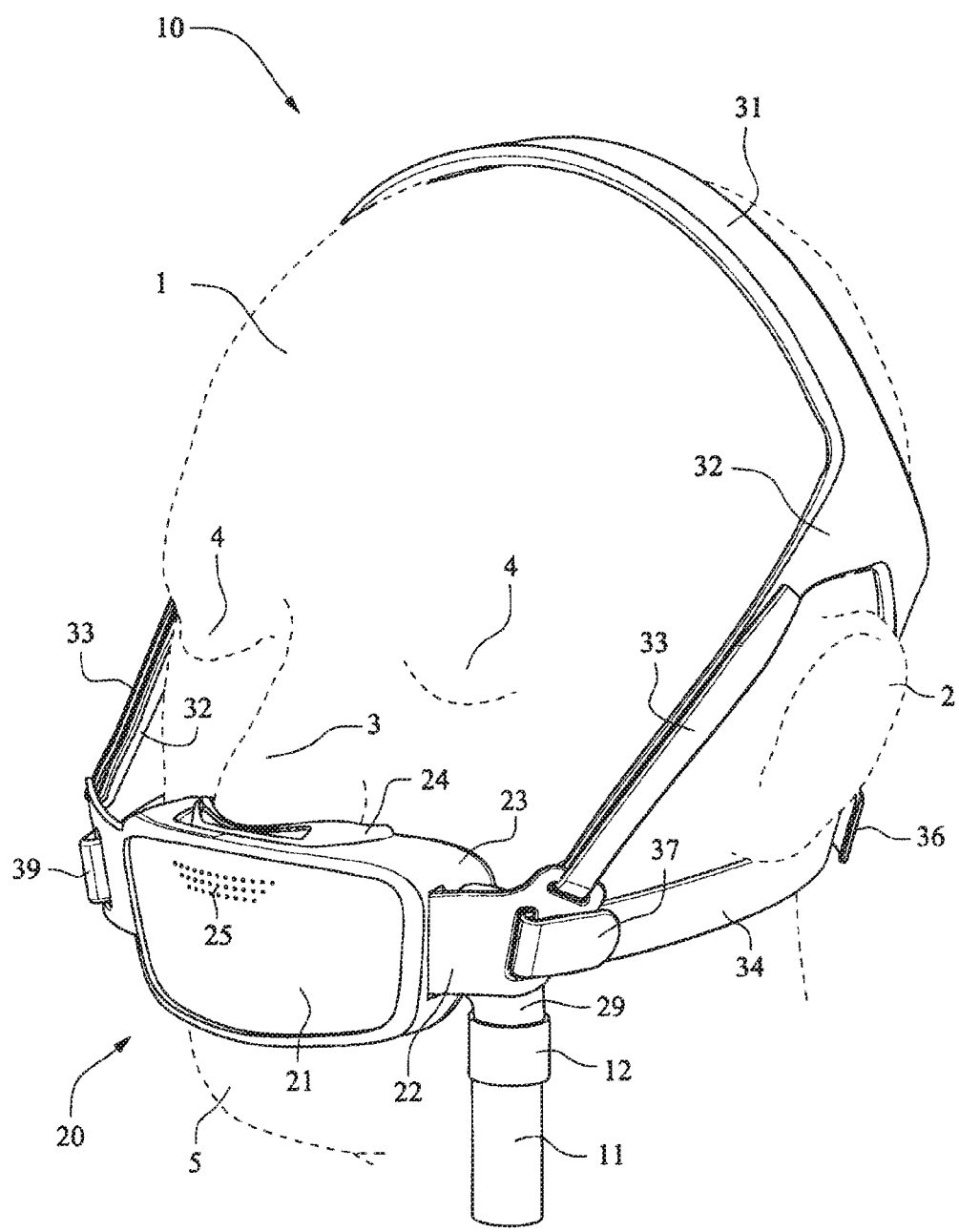
FIGS. 14-19 are front isometric, front, left side, right side, rear and bottom views, respectively, of a patient interface system according to another example embodiment of the present technology.
Figure 15:
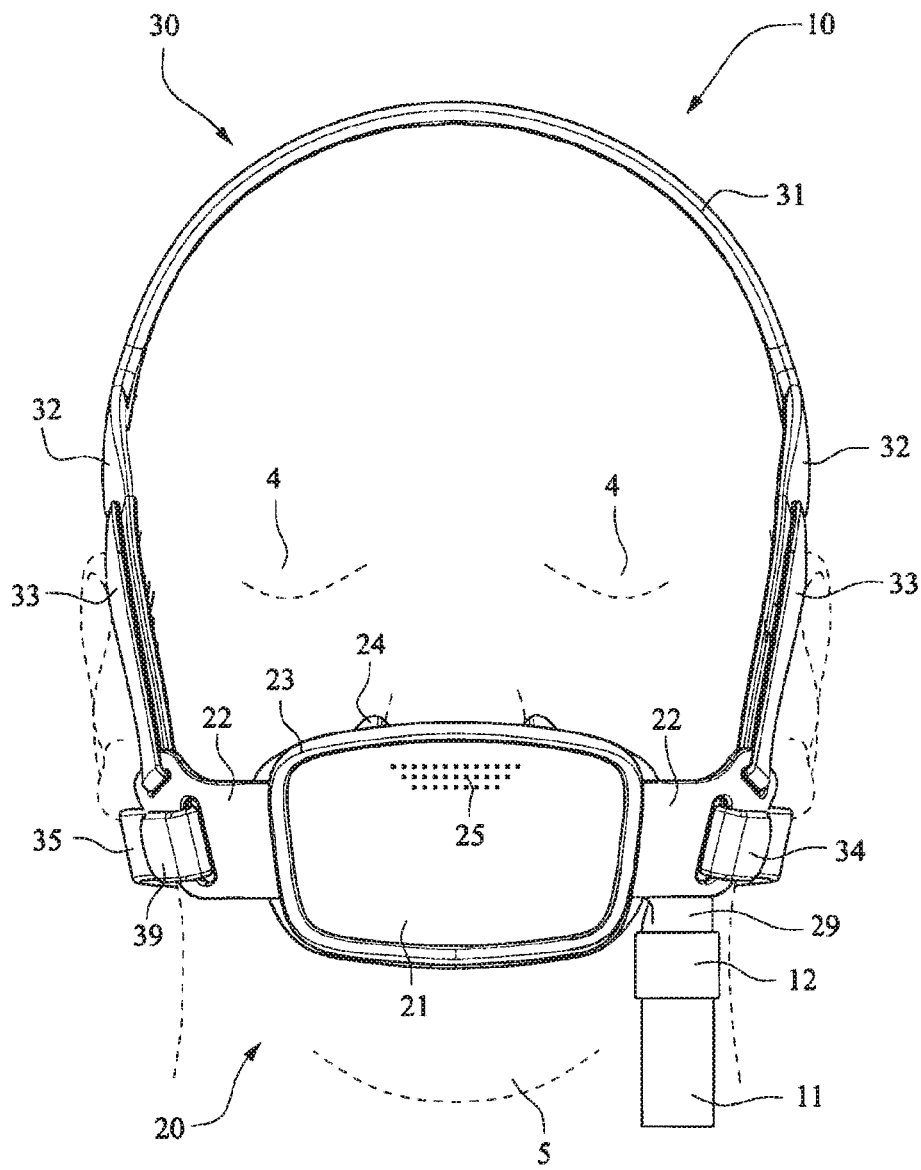
Figure 16:
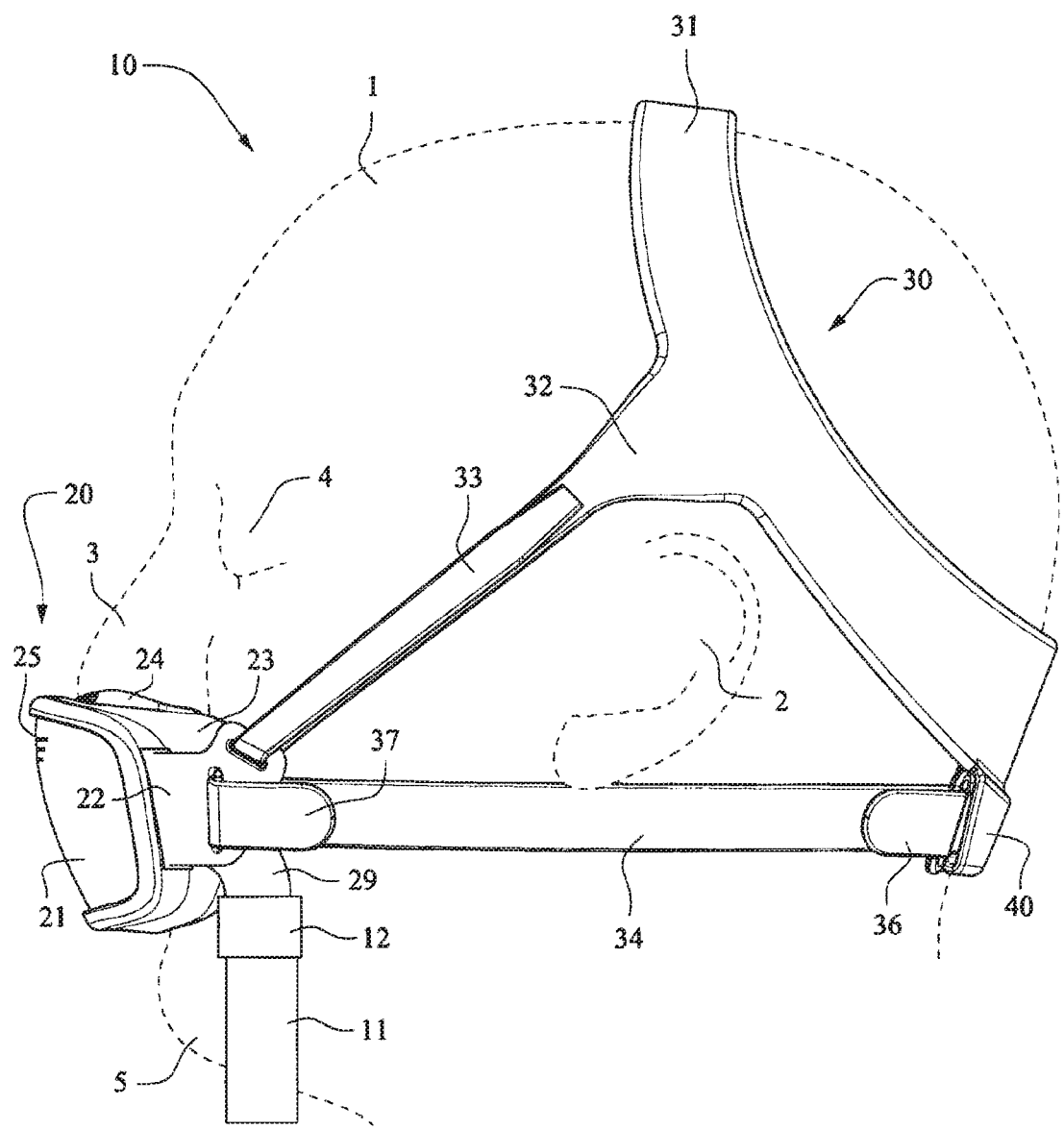
Figure 17:
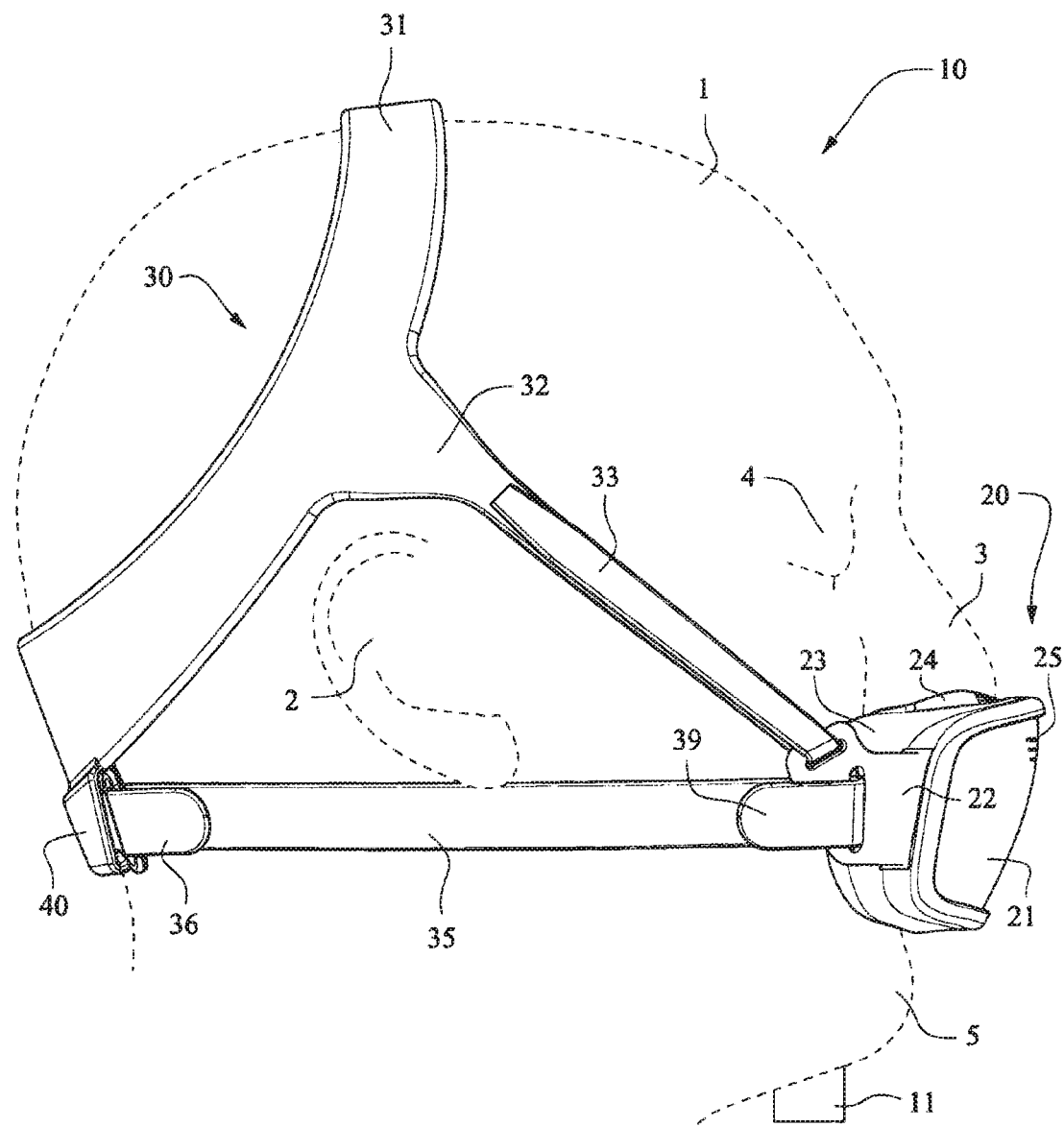
Figure 18:
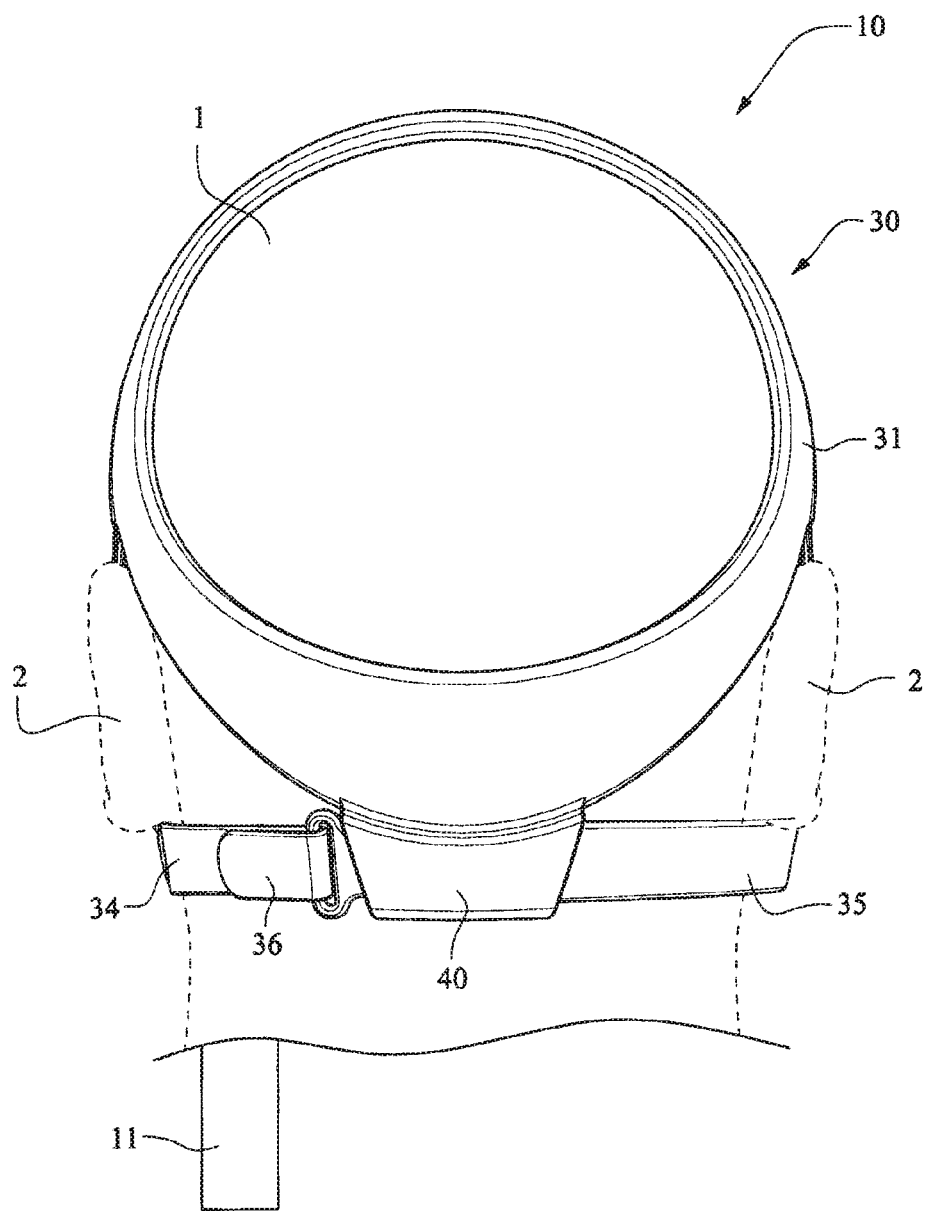
Figure 19:
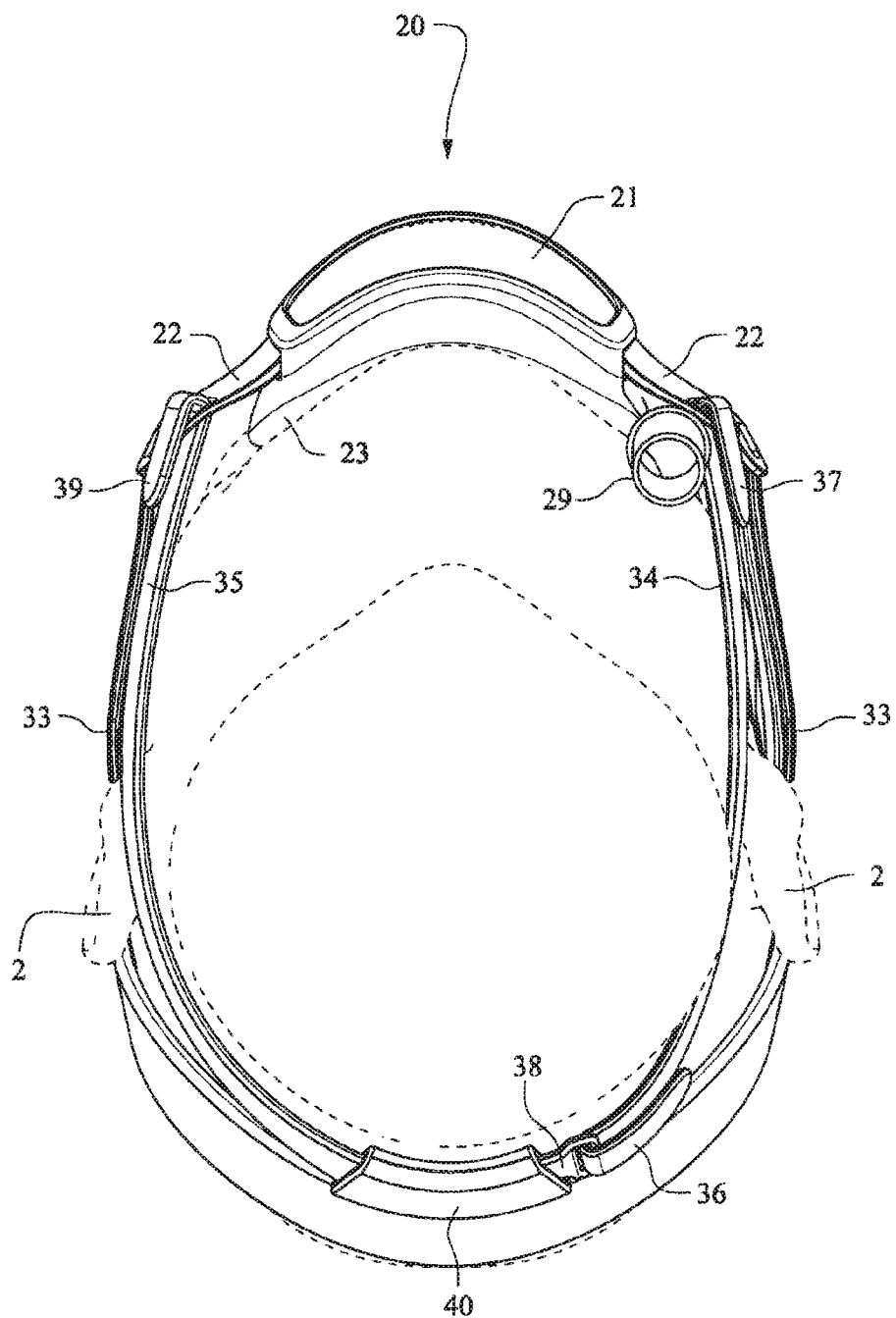
Figure 20:
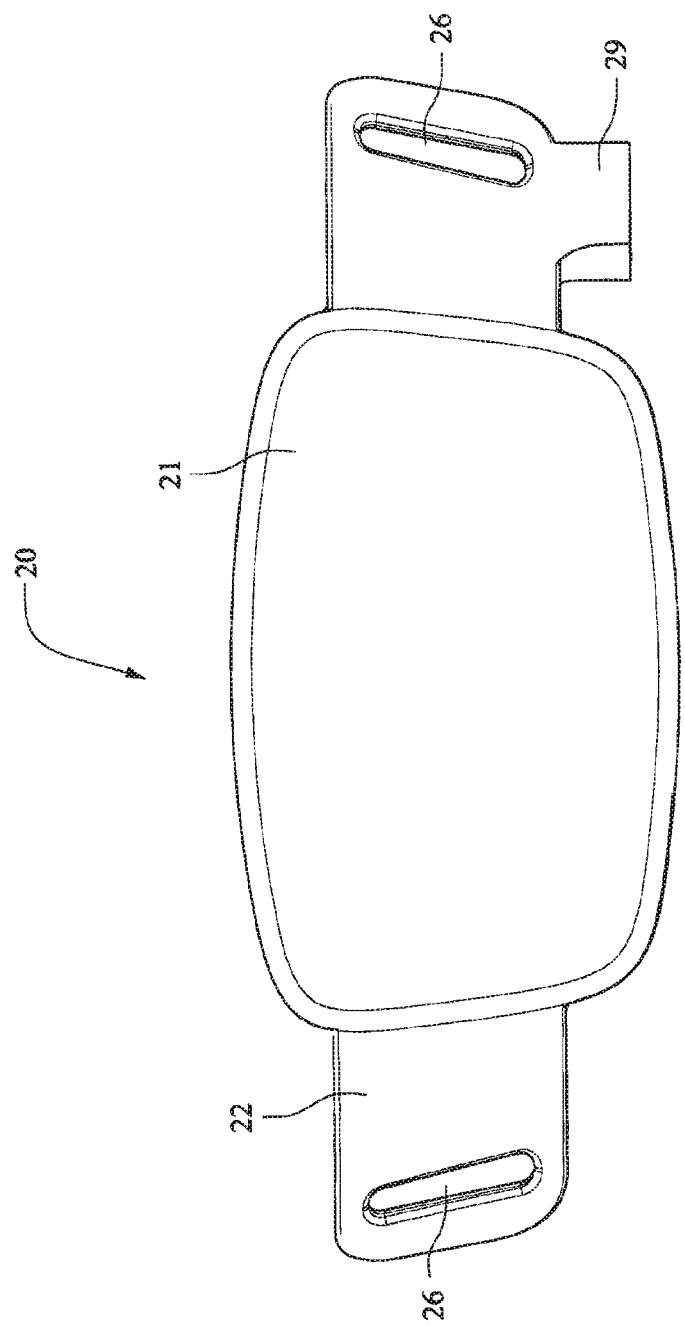
FIGS. 20-25 are front, rear, rear isometric, top, bottom, and left side views, respectively, of a fascia, frame or front plate, of the patient interface system of FIGS. 14-19.
Figure 21:
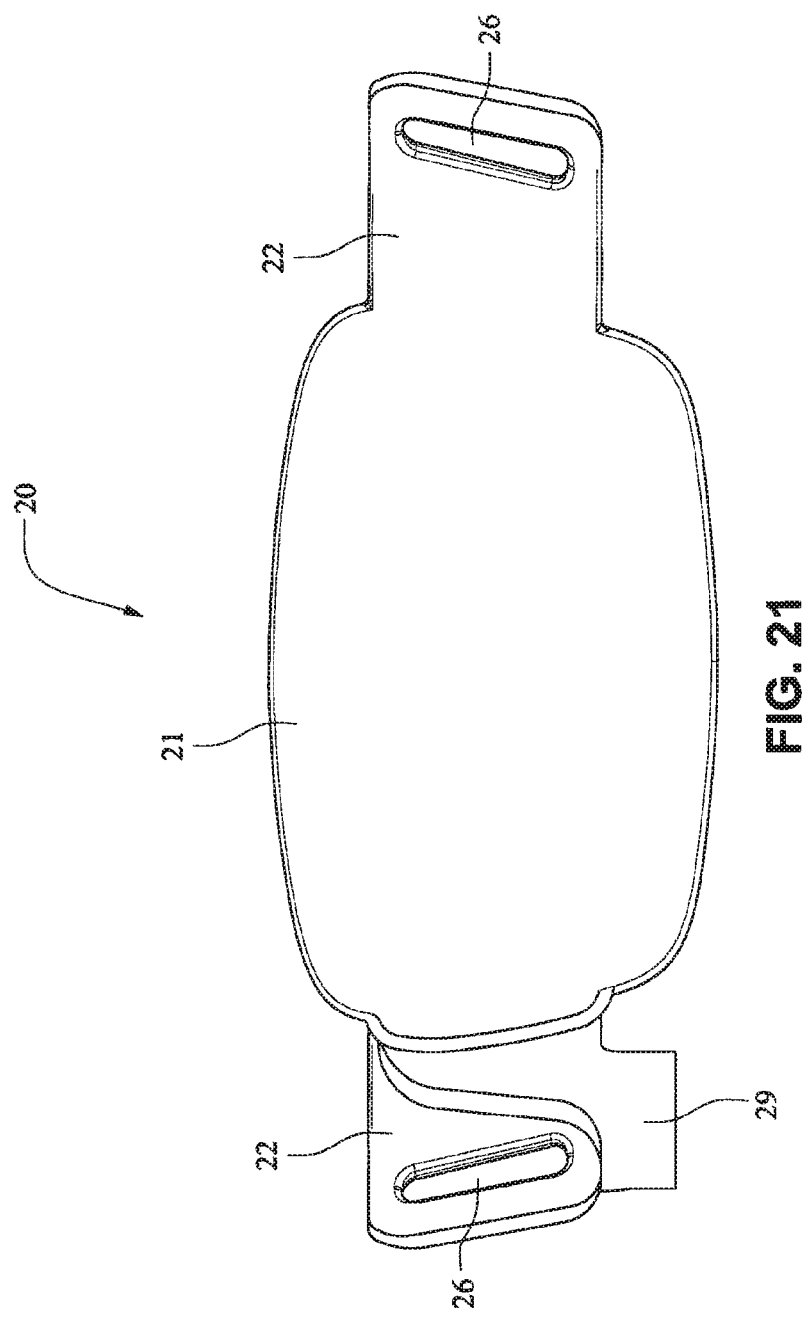
Figure 22:
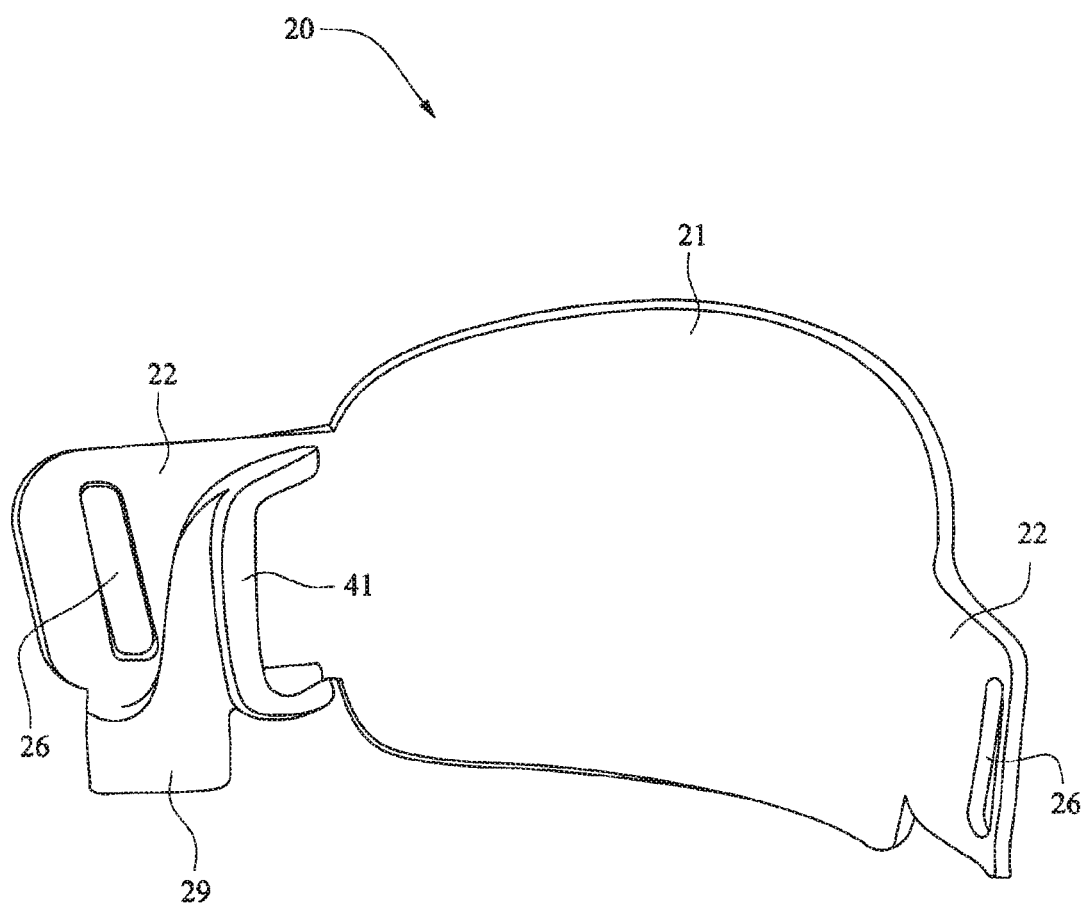
Figure 23:
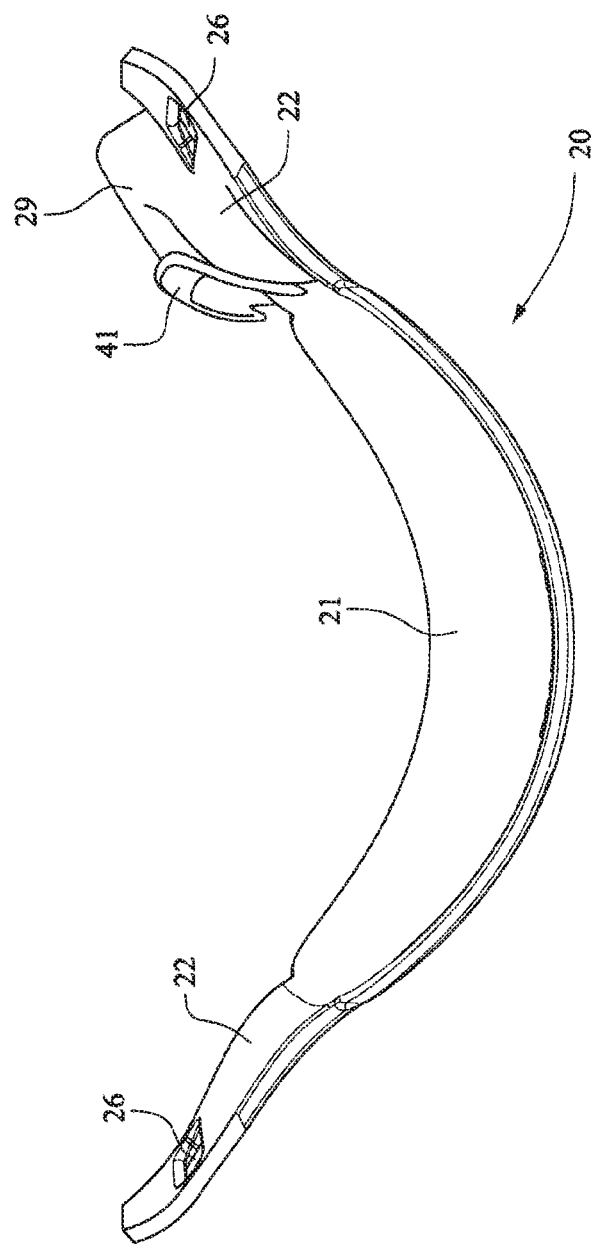
Figure 24:
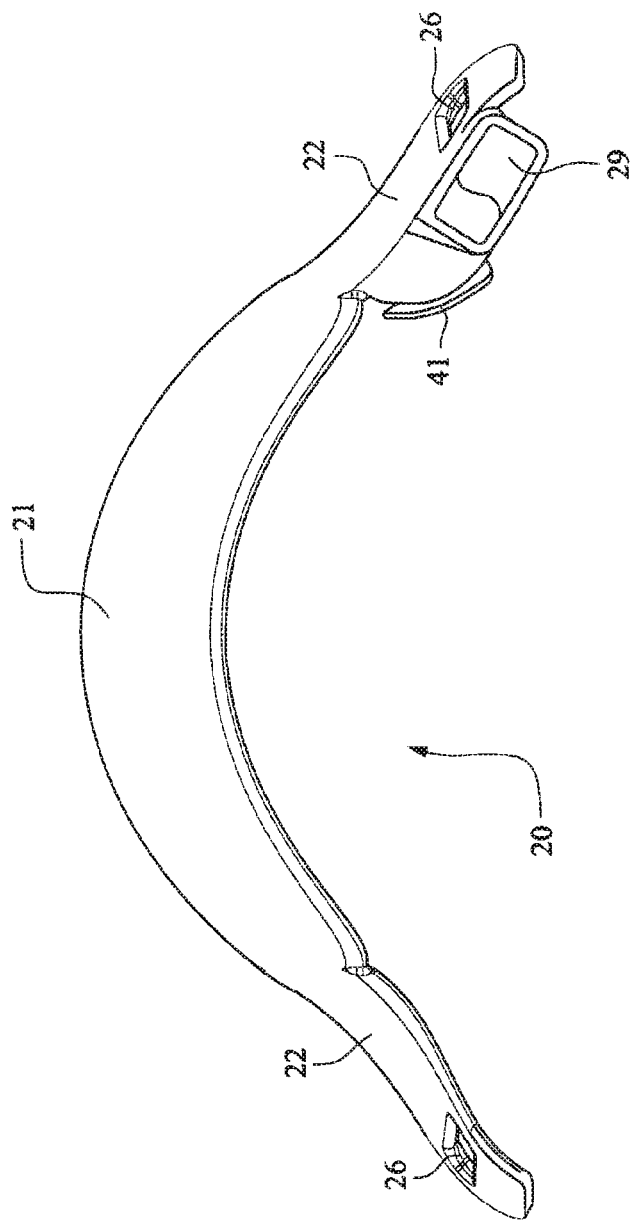
Figure 25:
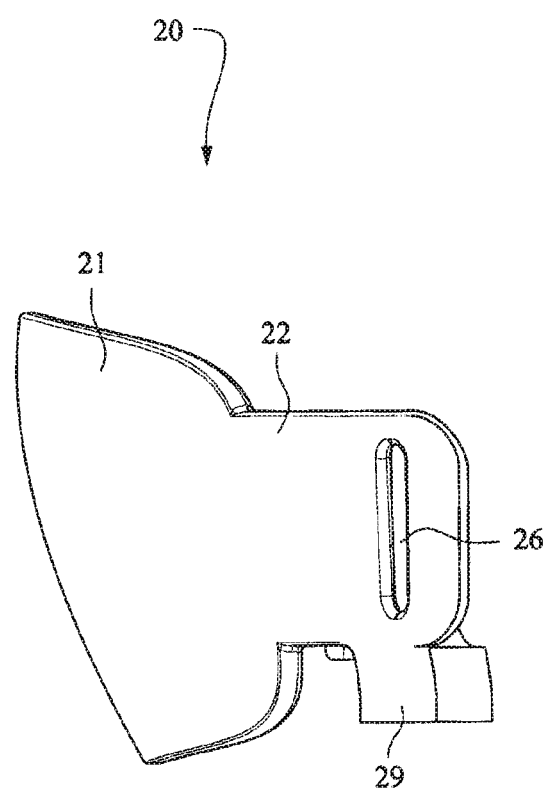
Figure 26:
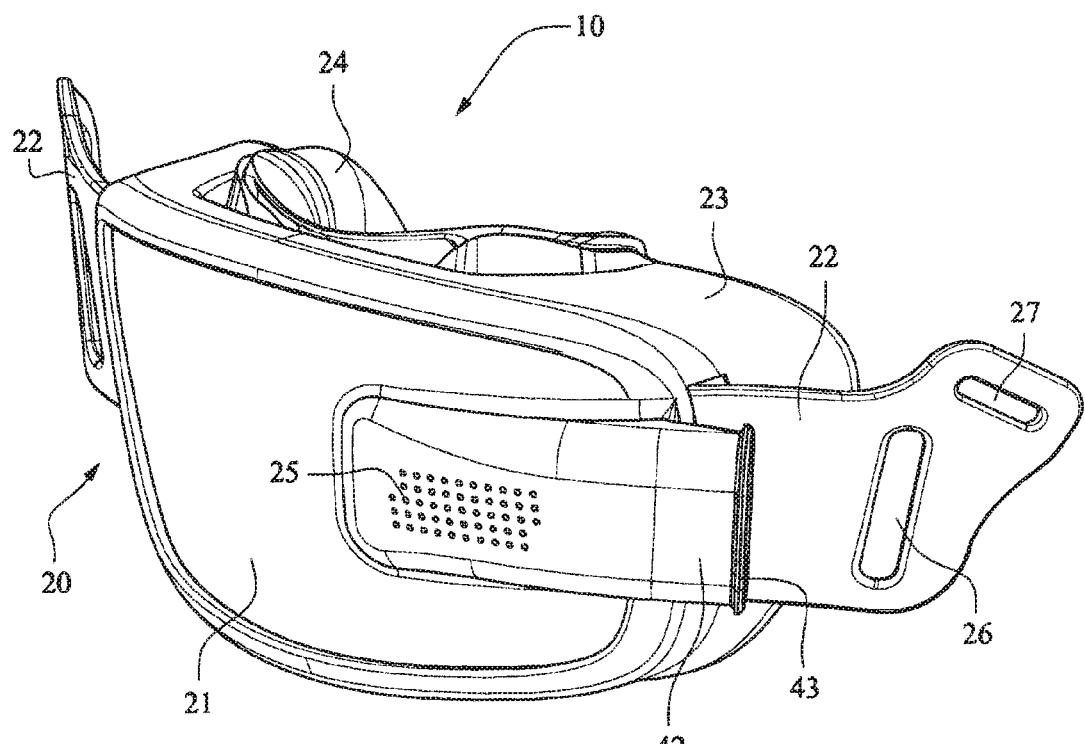
FIG. 26 is a front isometric view of a patient interface according to another example embodiment of the present technology and FIGS. 27-33 are front isometric, front, rear, right side, left side, top, and bottom views, respectively, of a fascia, frame or front plate, of the patient interface system of FIG. 26.
Figure 27:
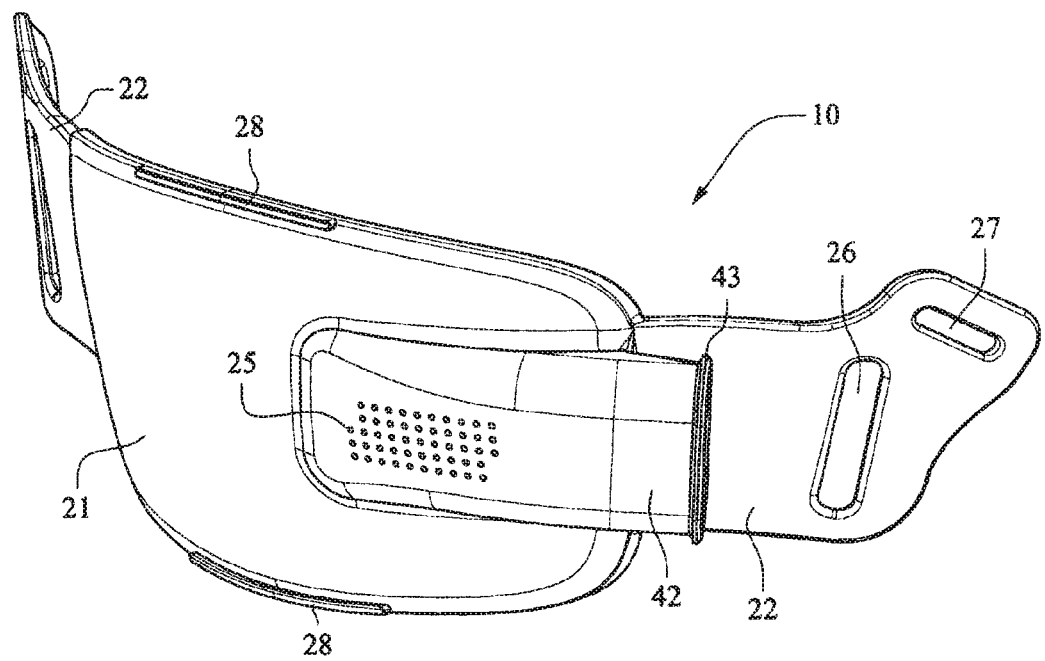
Figure 28:
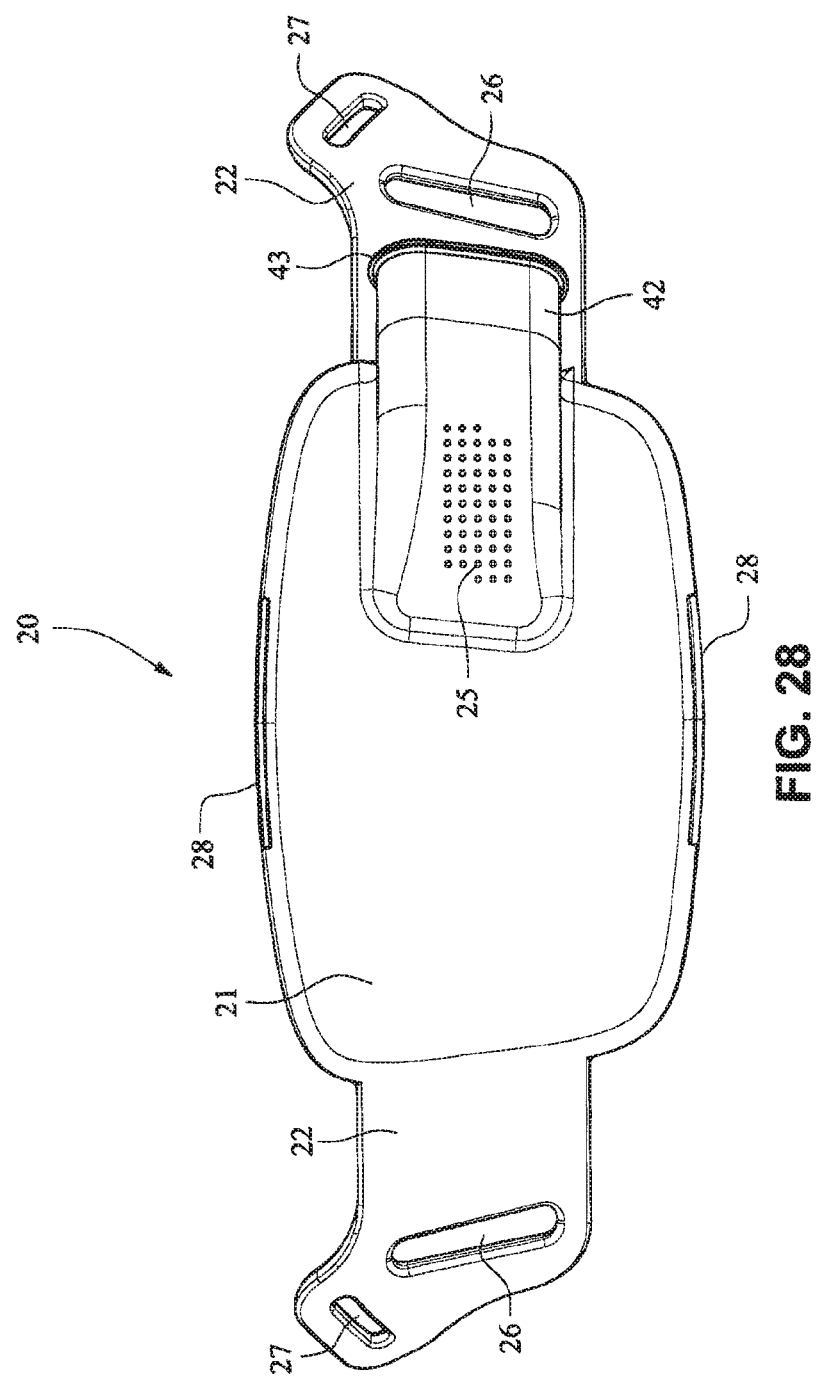
Figure 29:
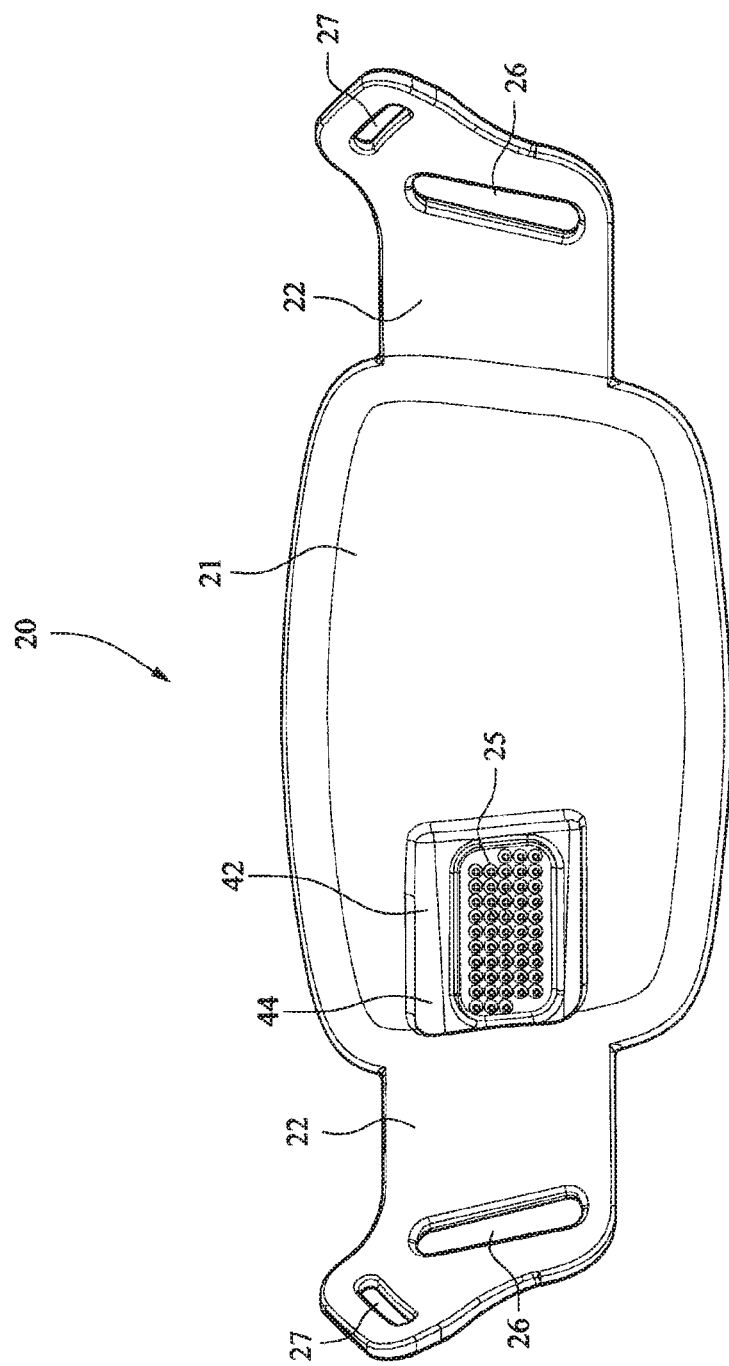
Figure 30:
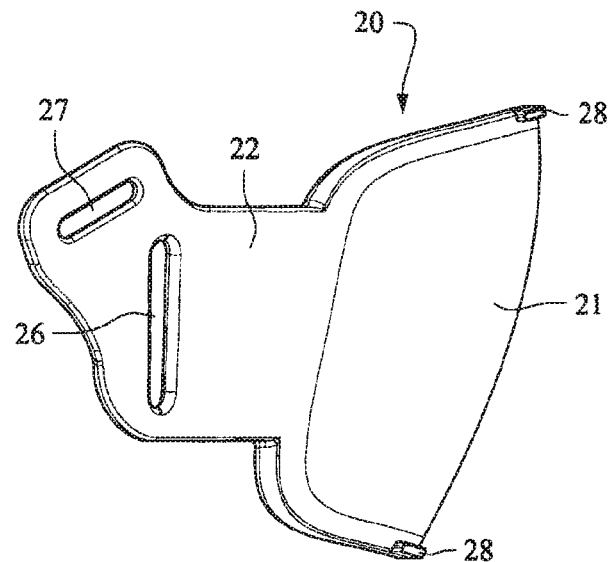
Figure 31:
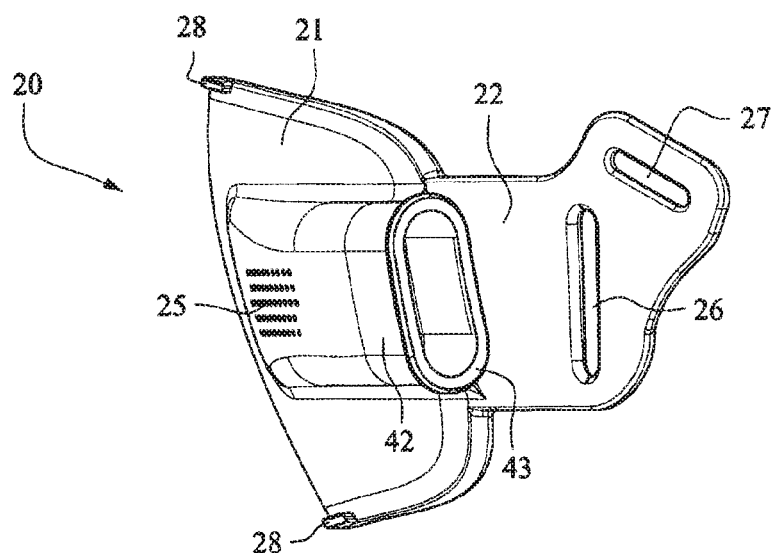
Figure 32:
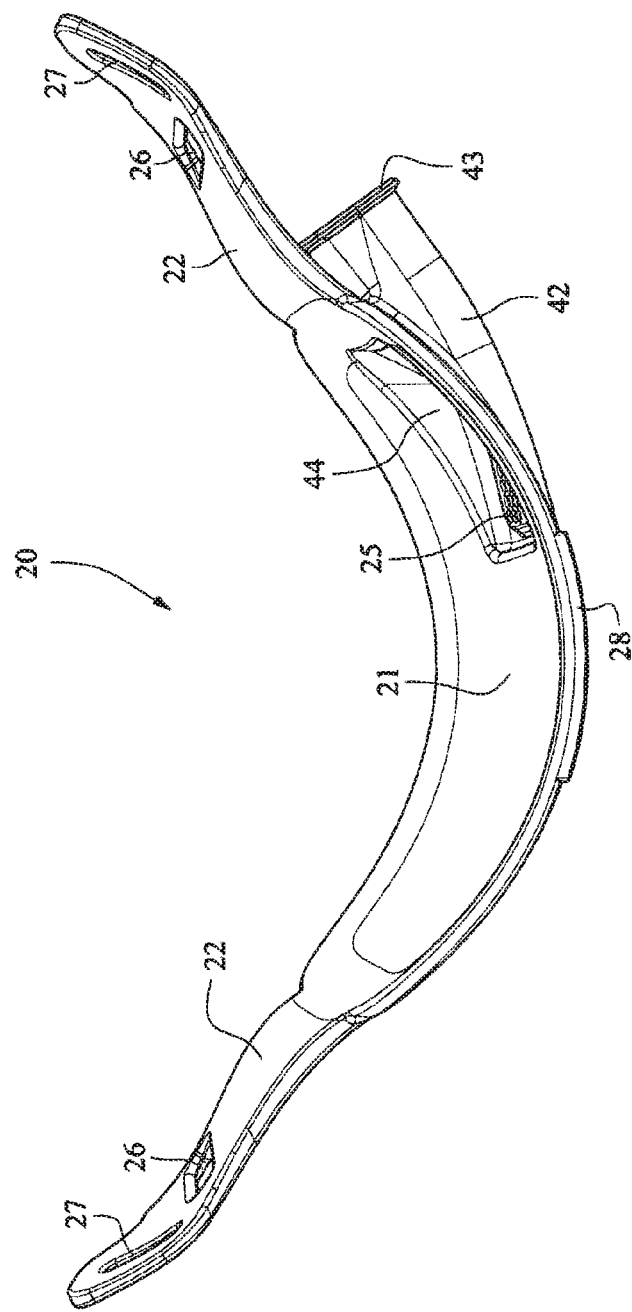
Figure 33:
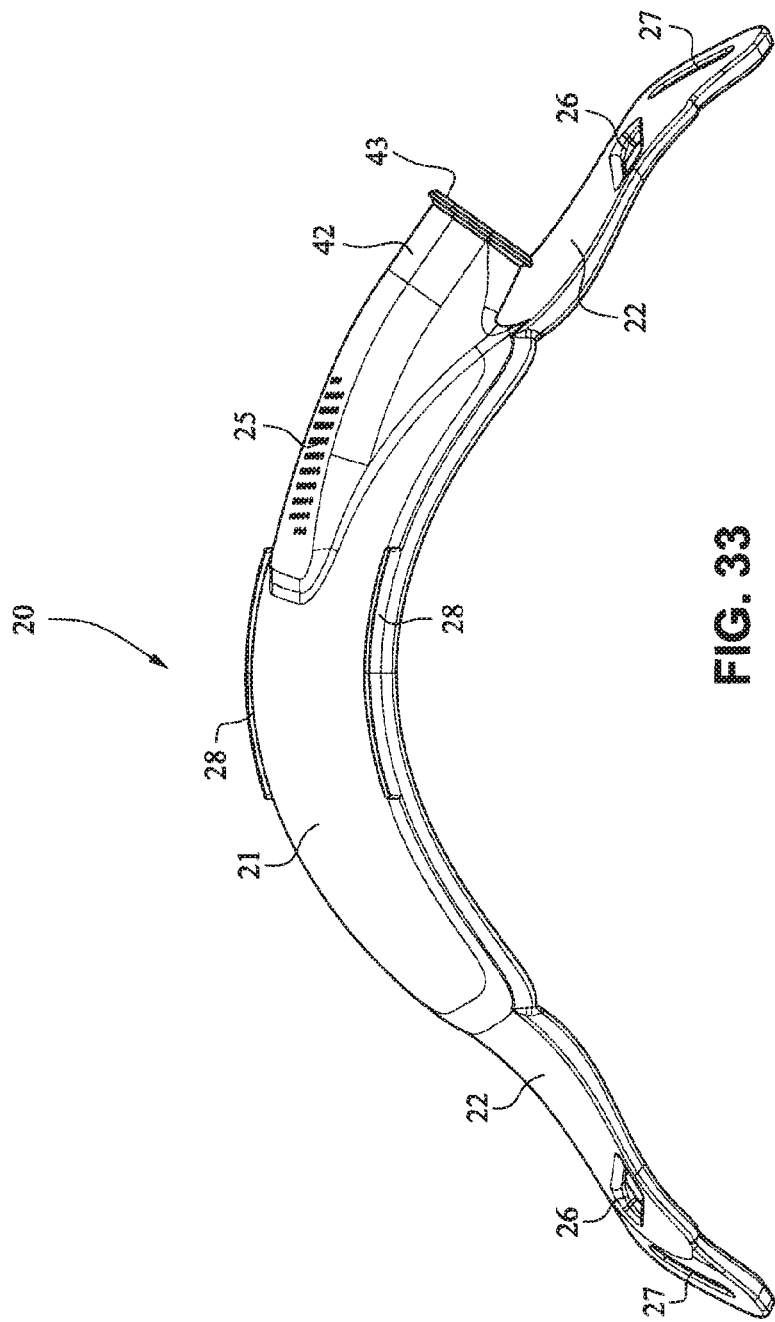
Figure 34:
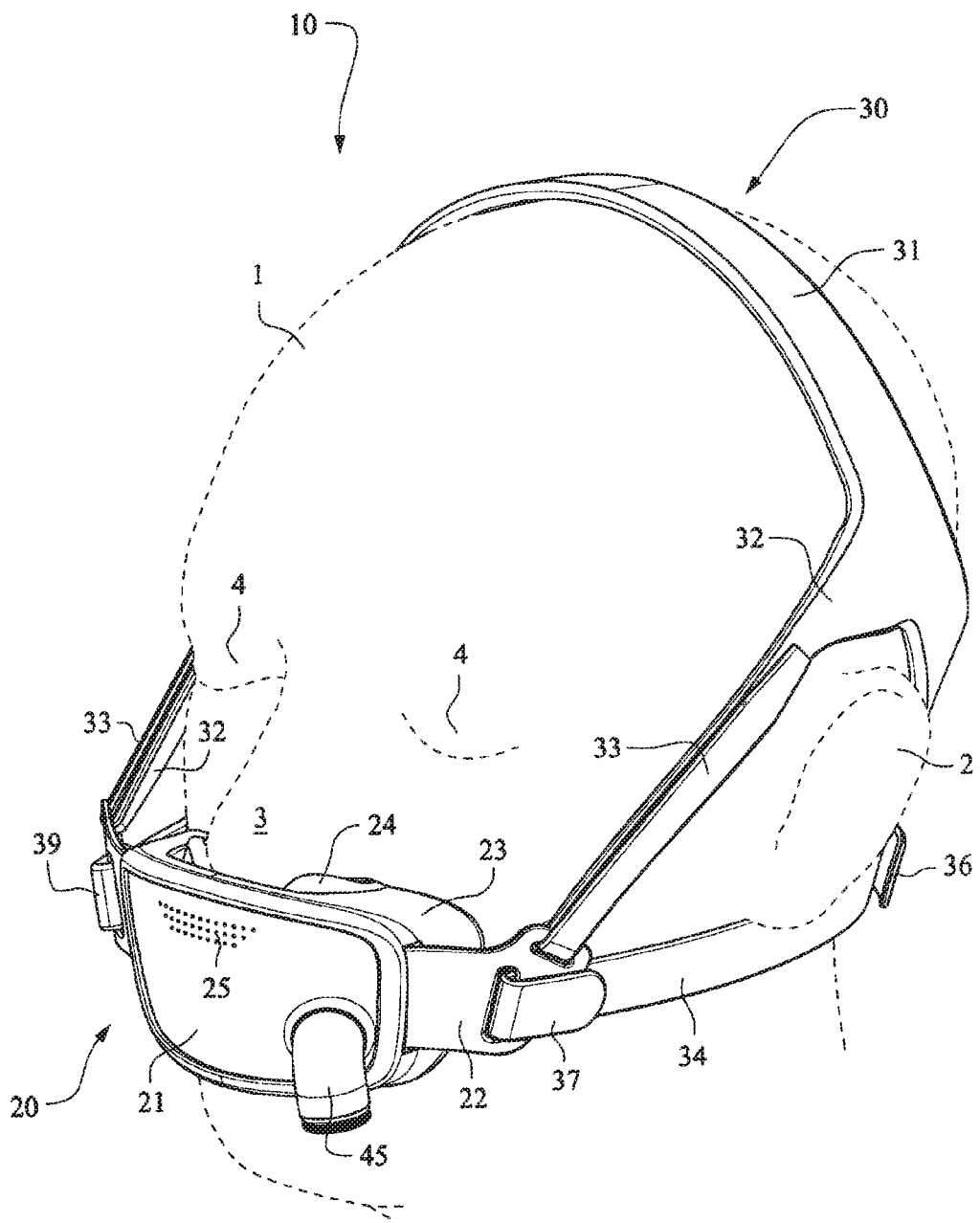
FIGS. 34-40 are front isometric, front, rear, left side, right side, top, and bottom views, respectively, of a patient interface system according to another example embodiment of the present technology.
Figure 35:
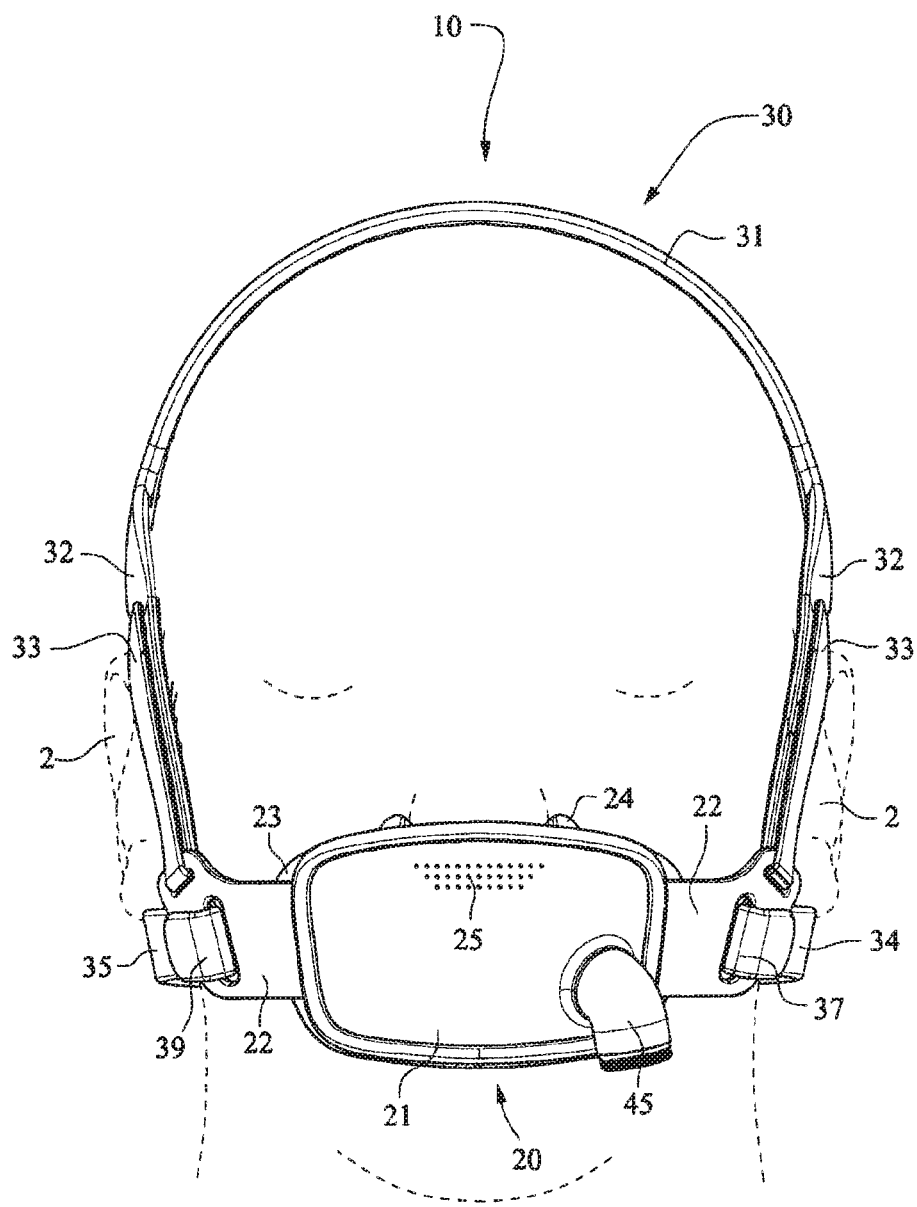
Figure 36:
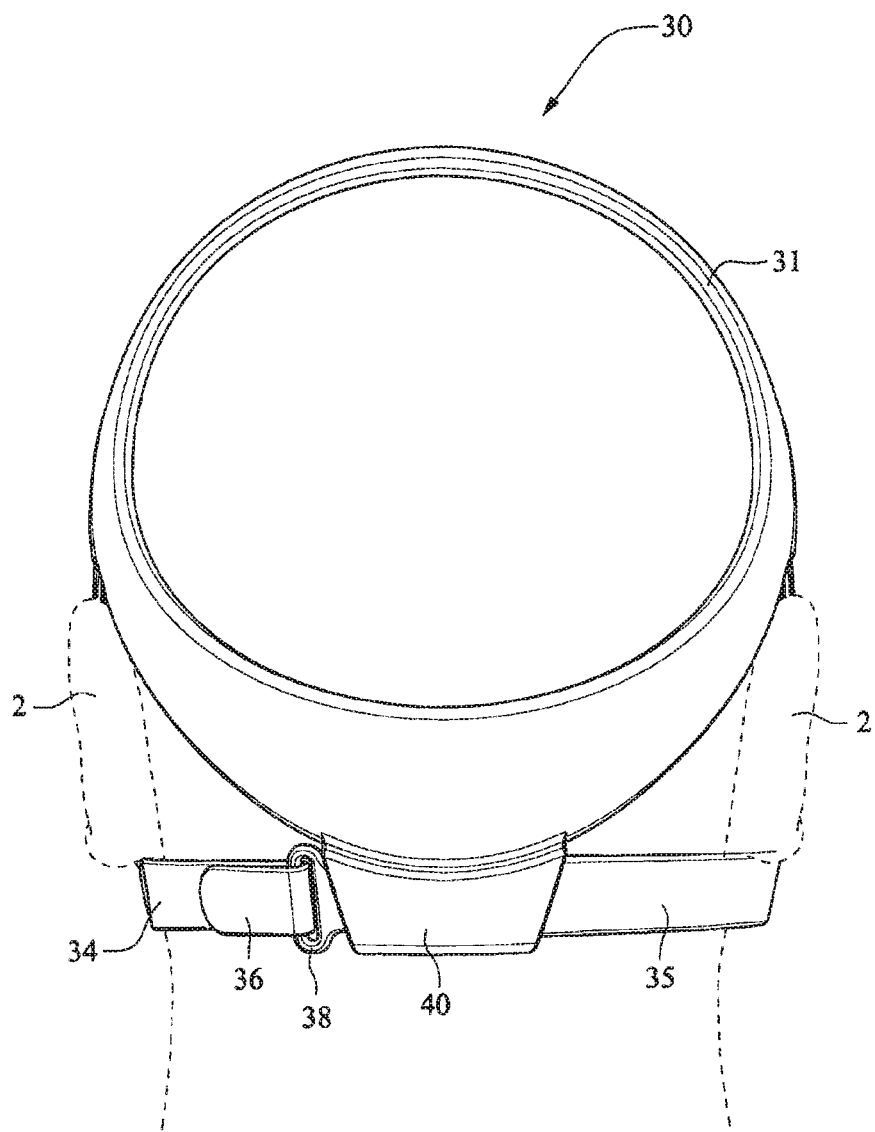
Figure 37:
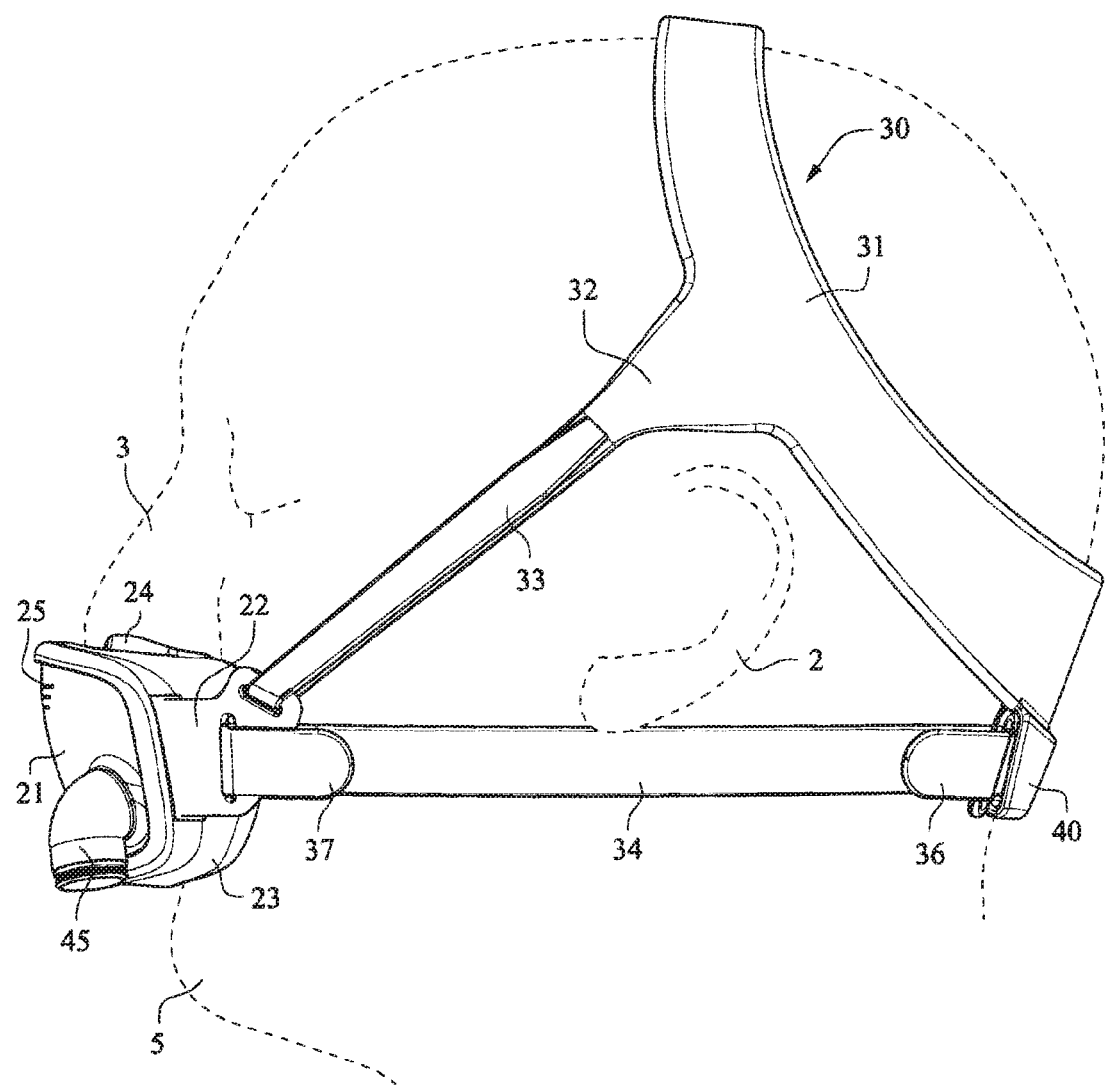
Figure 38:
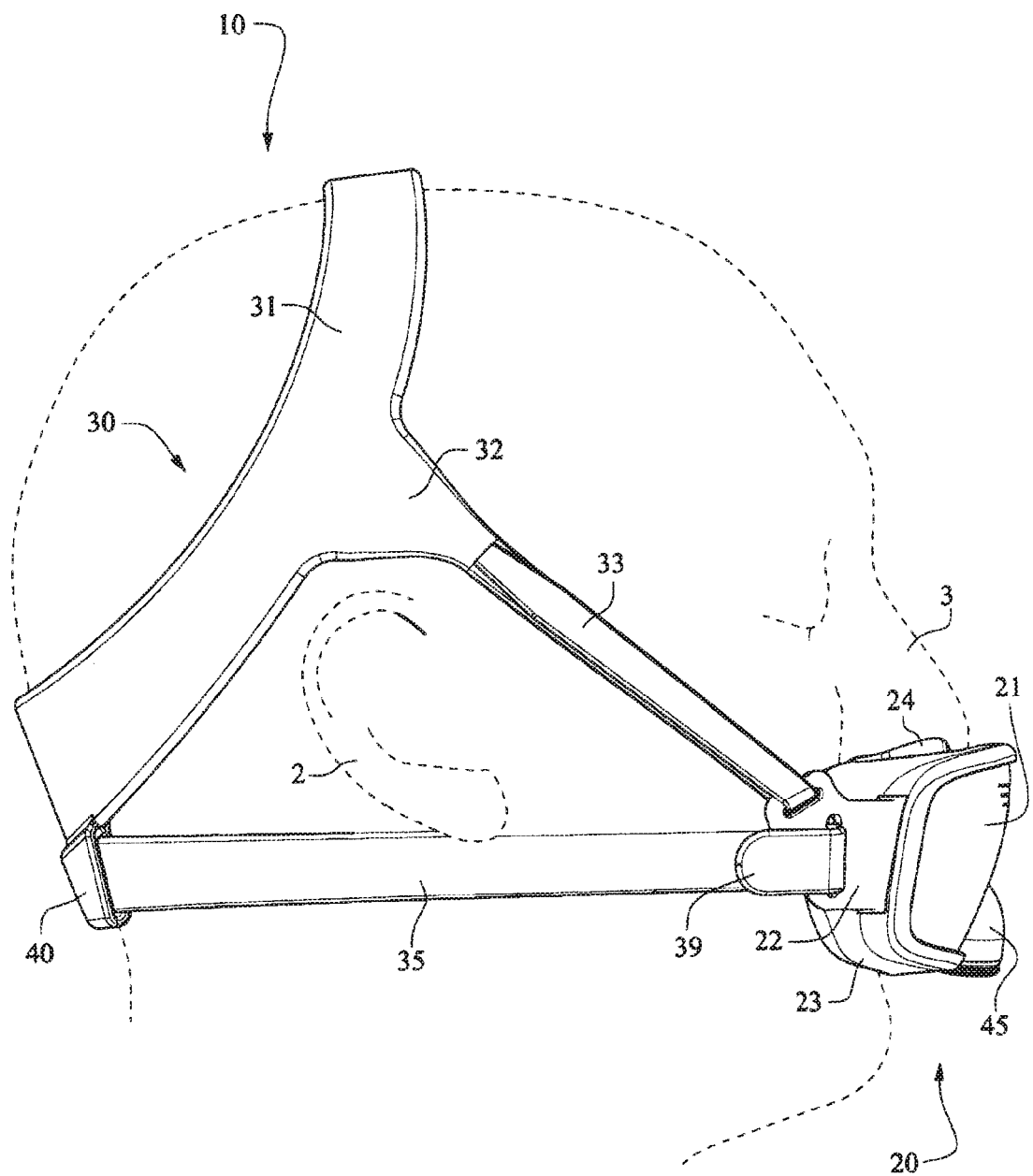
Figure 39:
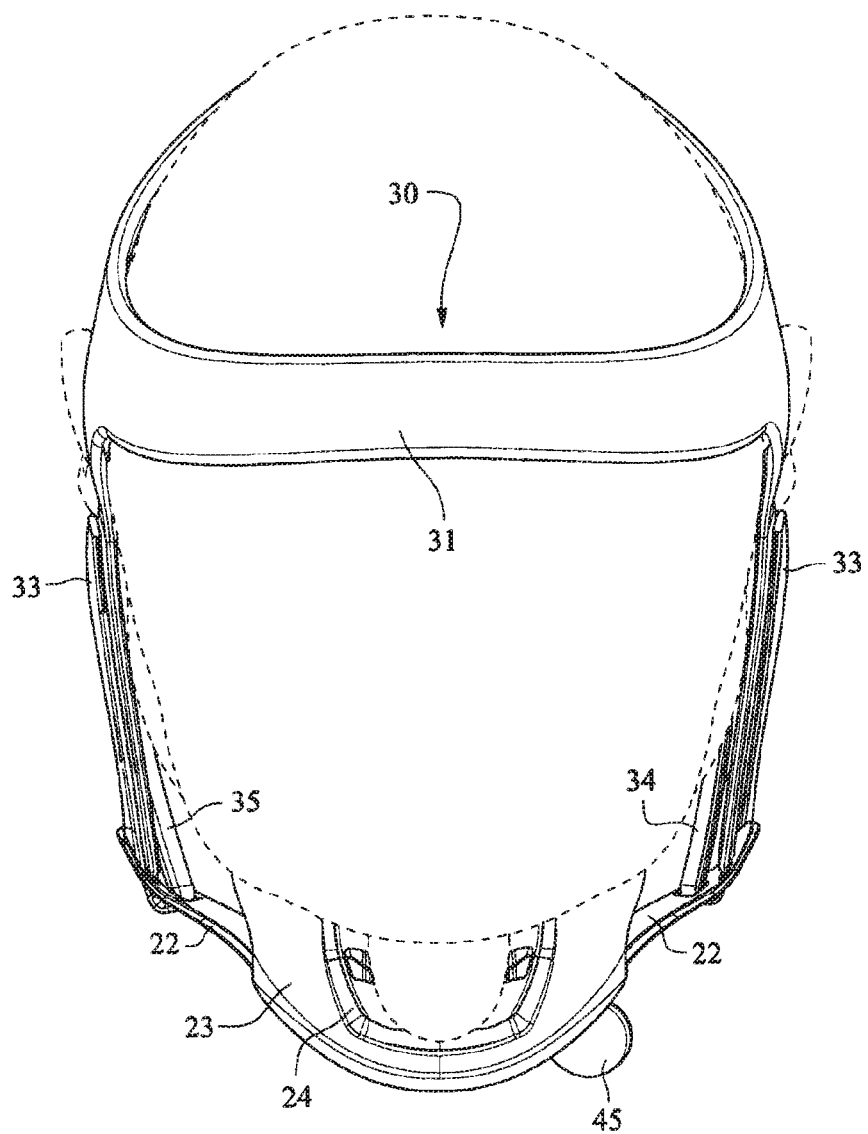
Figure 40:
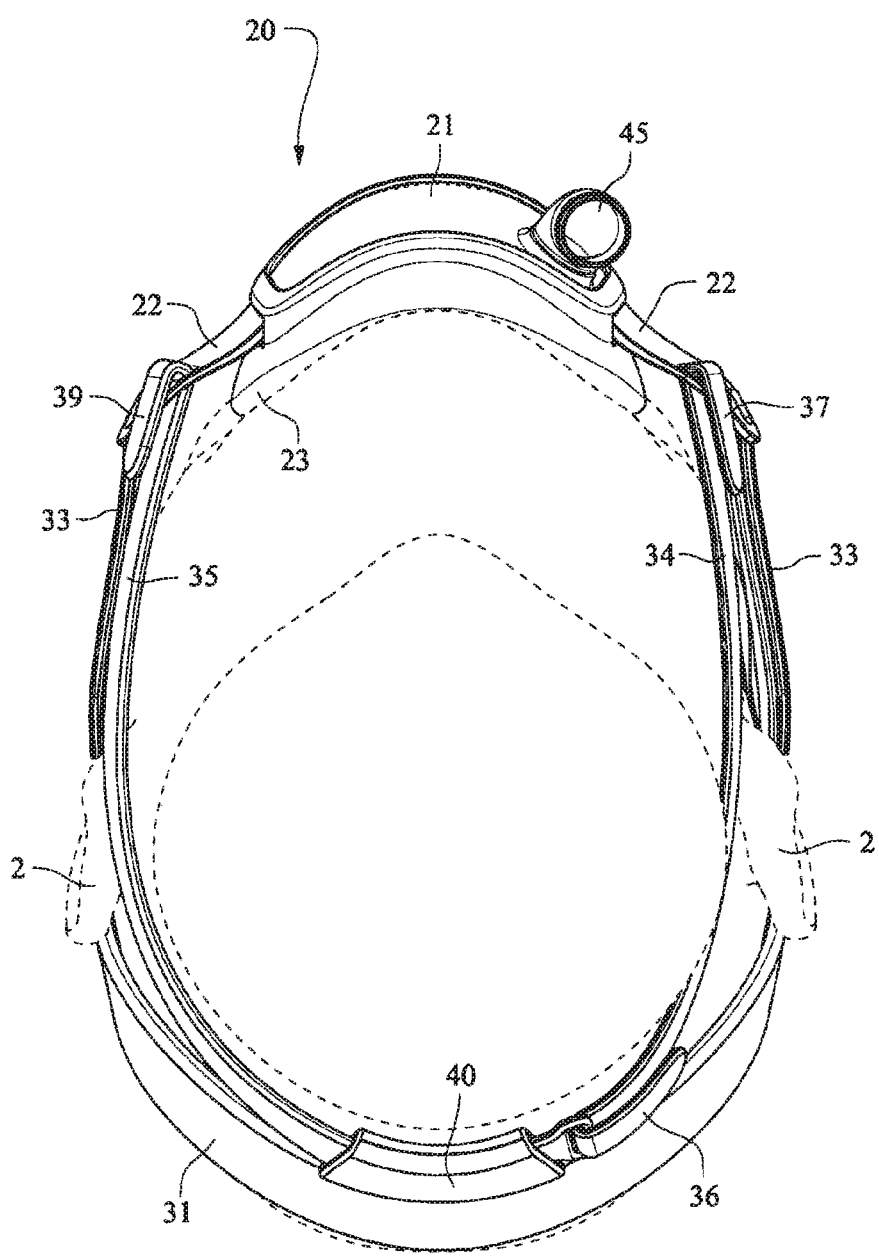
Figure 41:
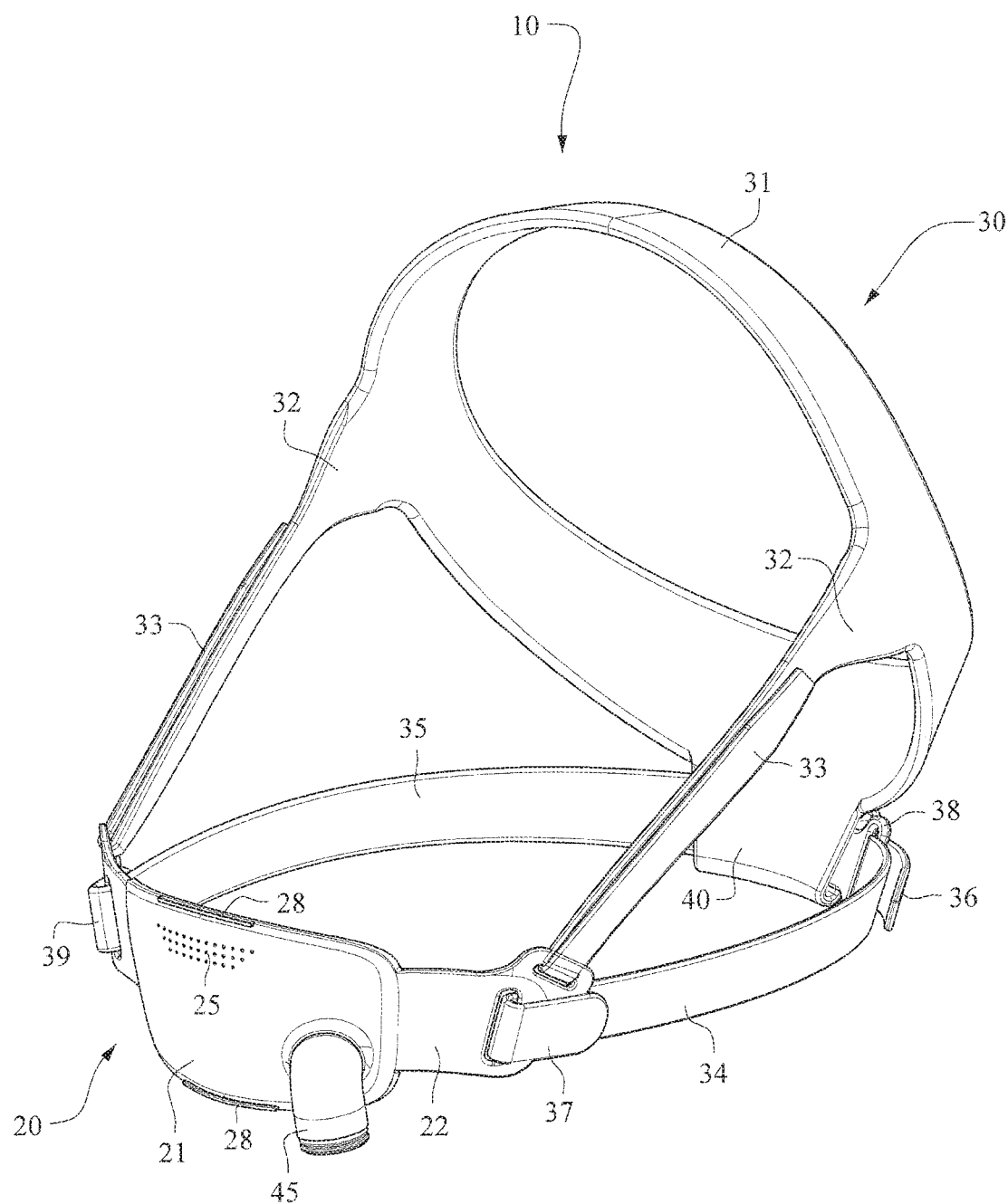
FIGS. 41-47 are front isometric, front, rear, left side, right side, top, and bottom views, respectively, of the fascia, frame or front plate, including an elbow and the patient interface positioning system of the patient interface system of FIGS. 34-40.
Figure 42:
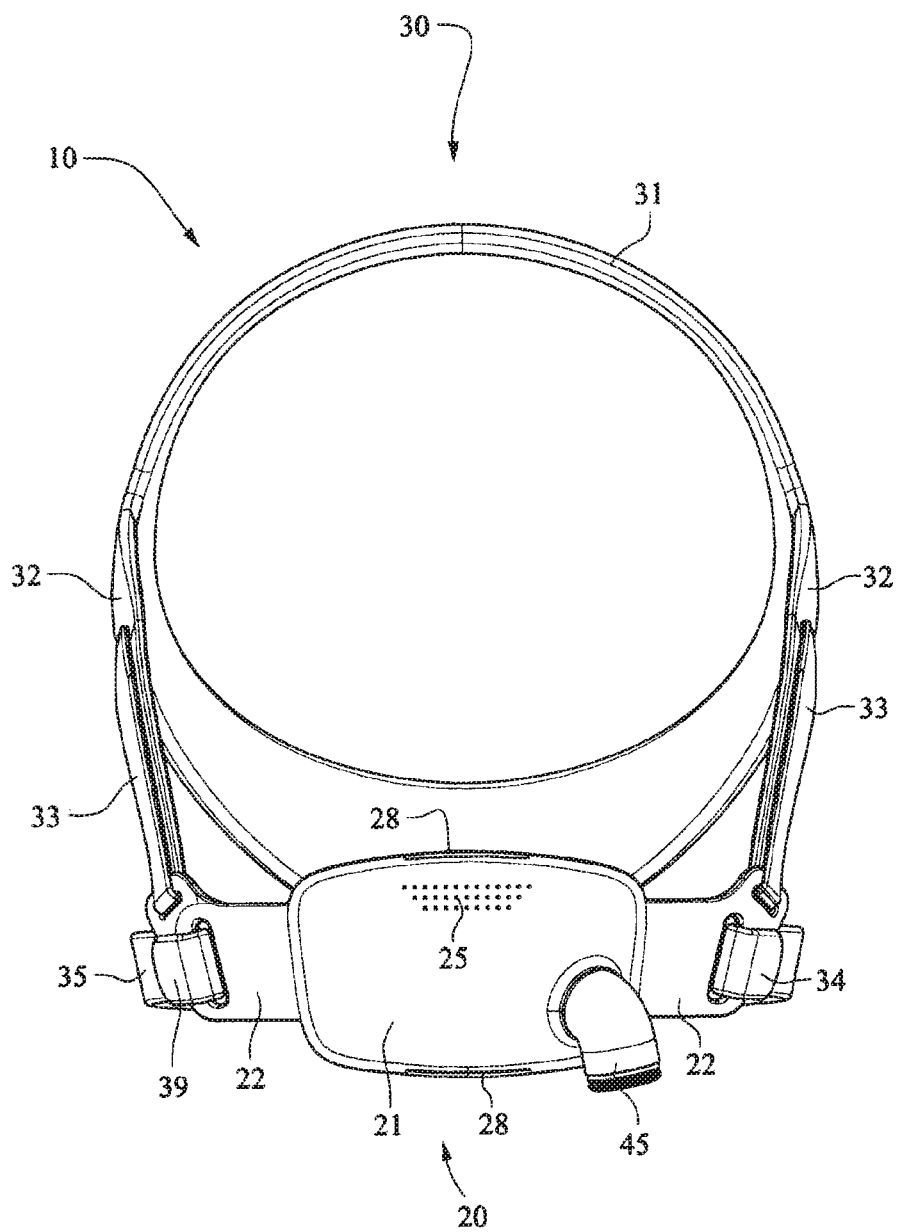
Figure 43:
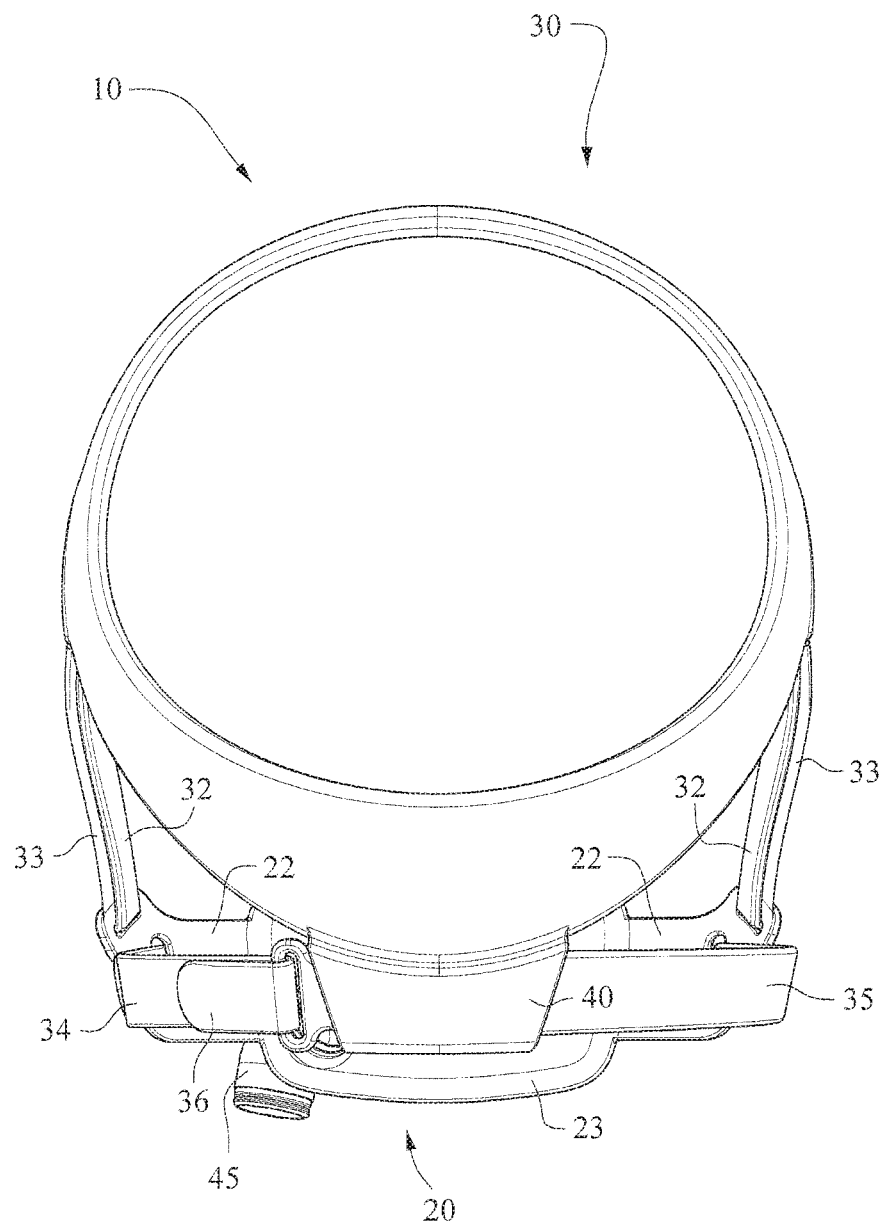
Figure 44:
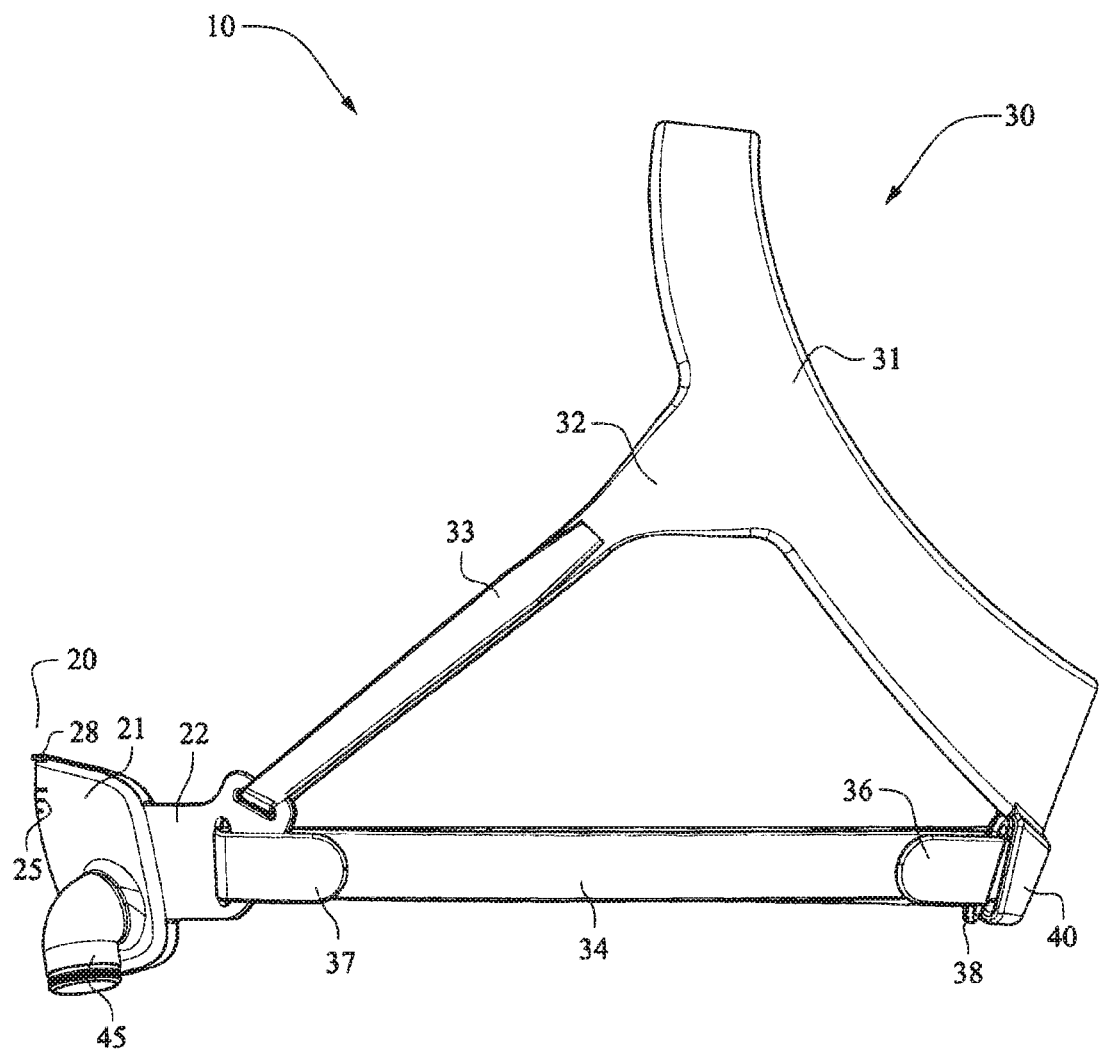
Figure 45:
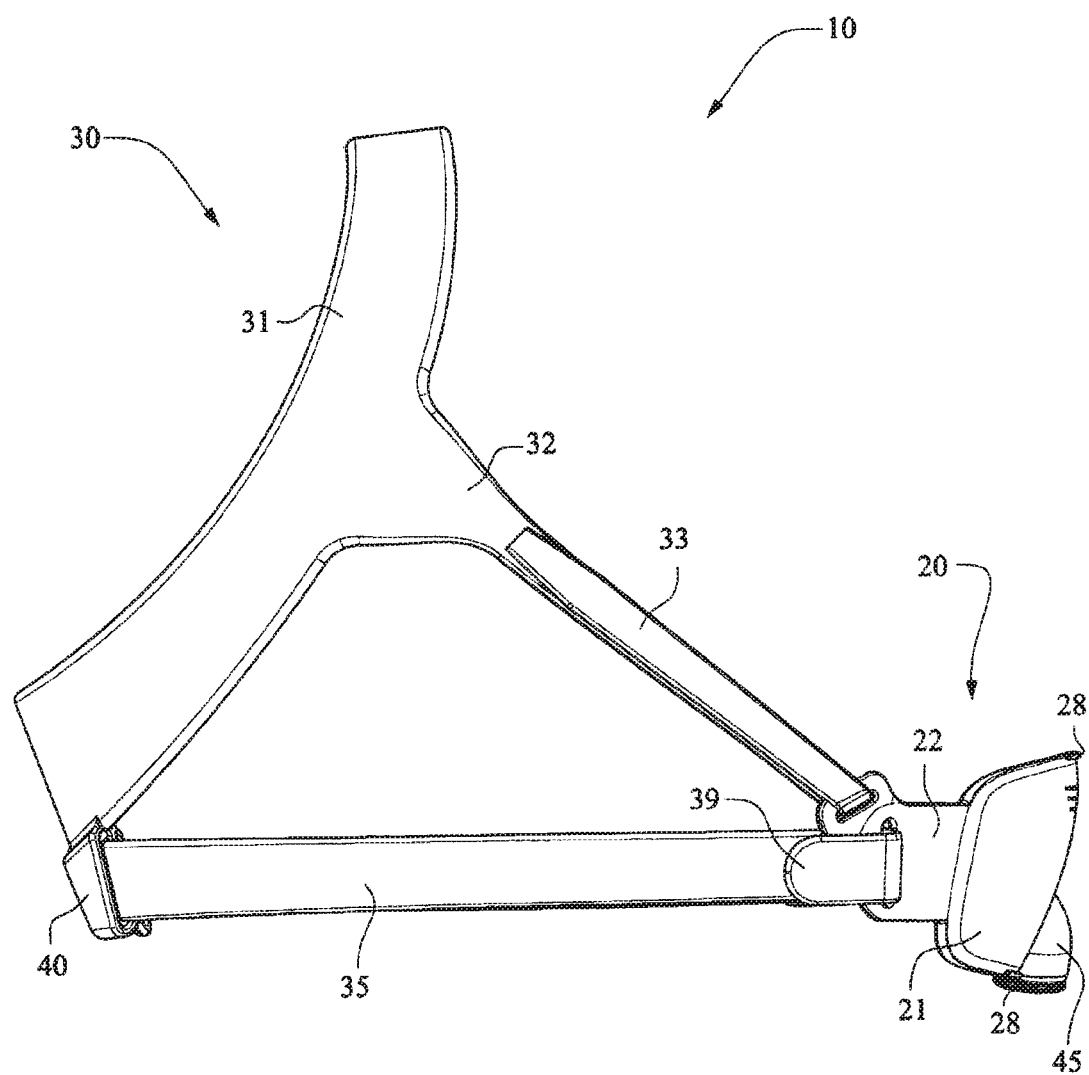
Figure 46:
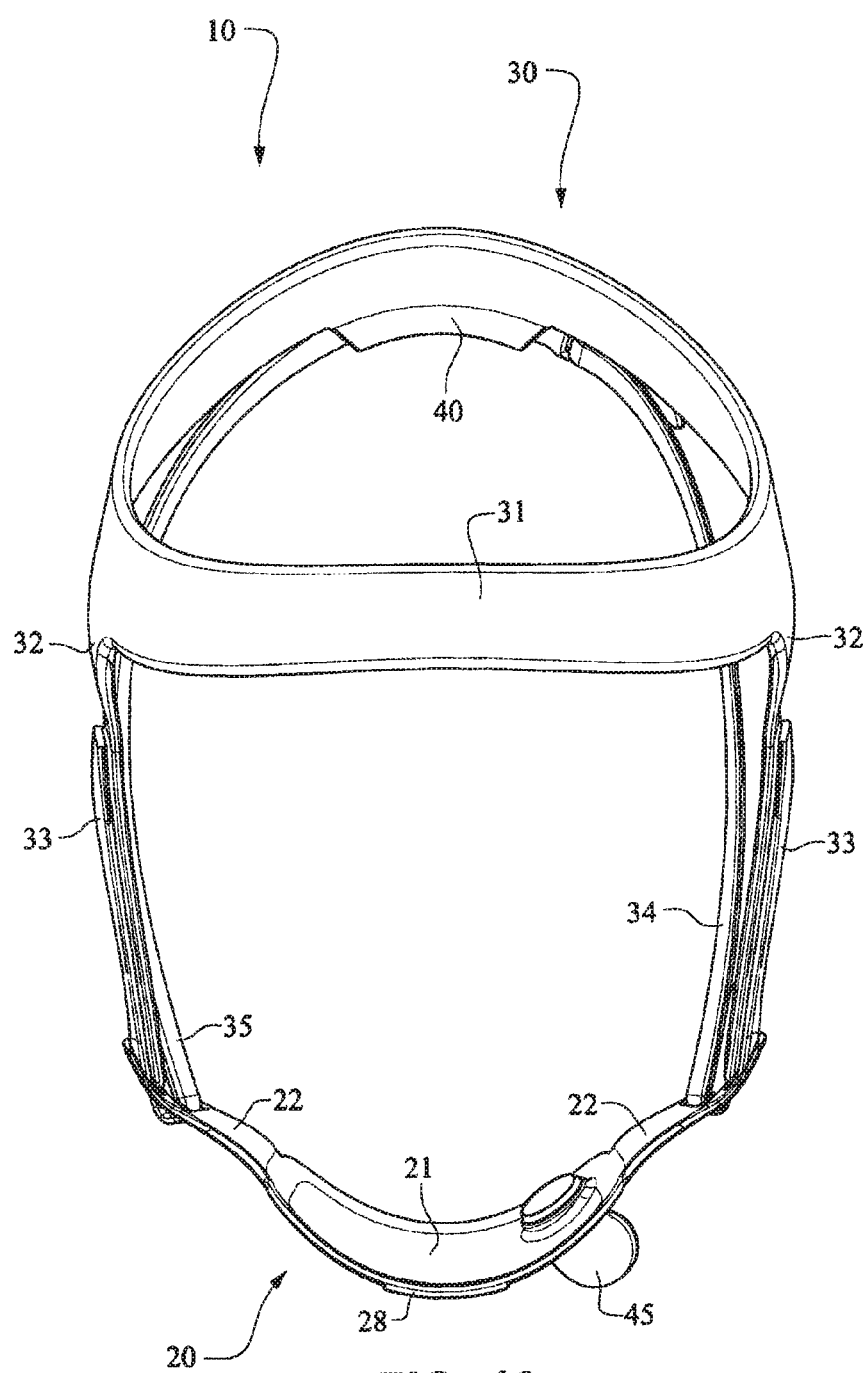
Figure 47:
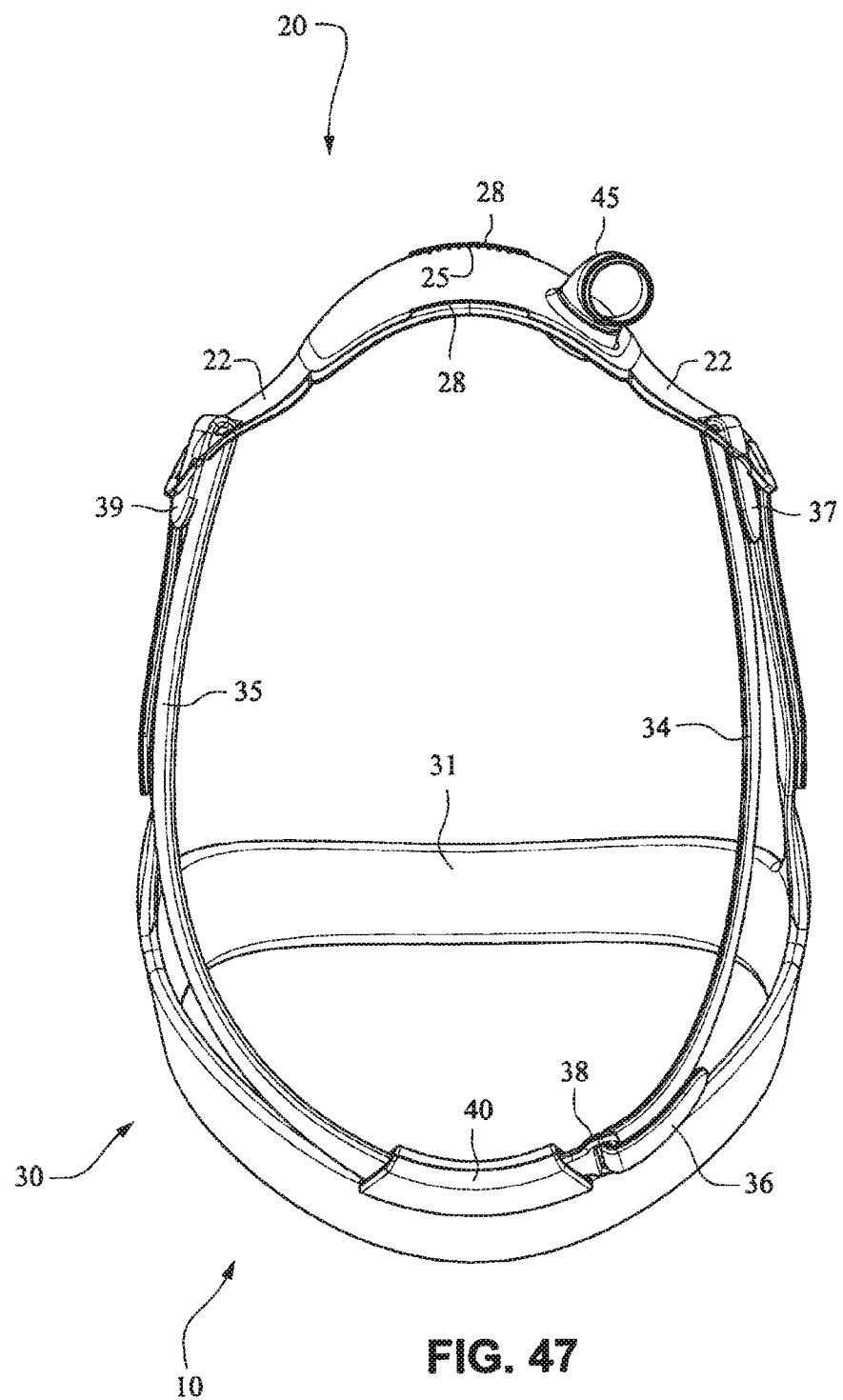
Figure 48:
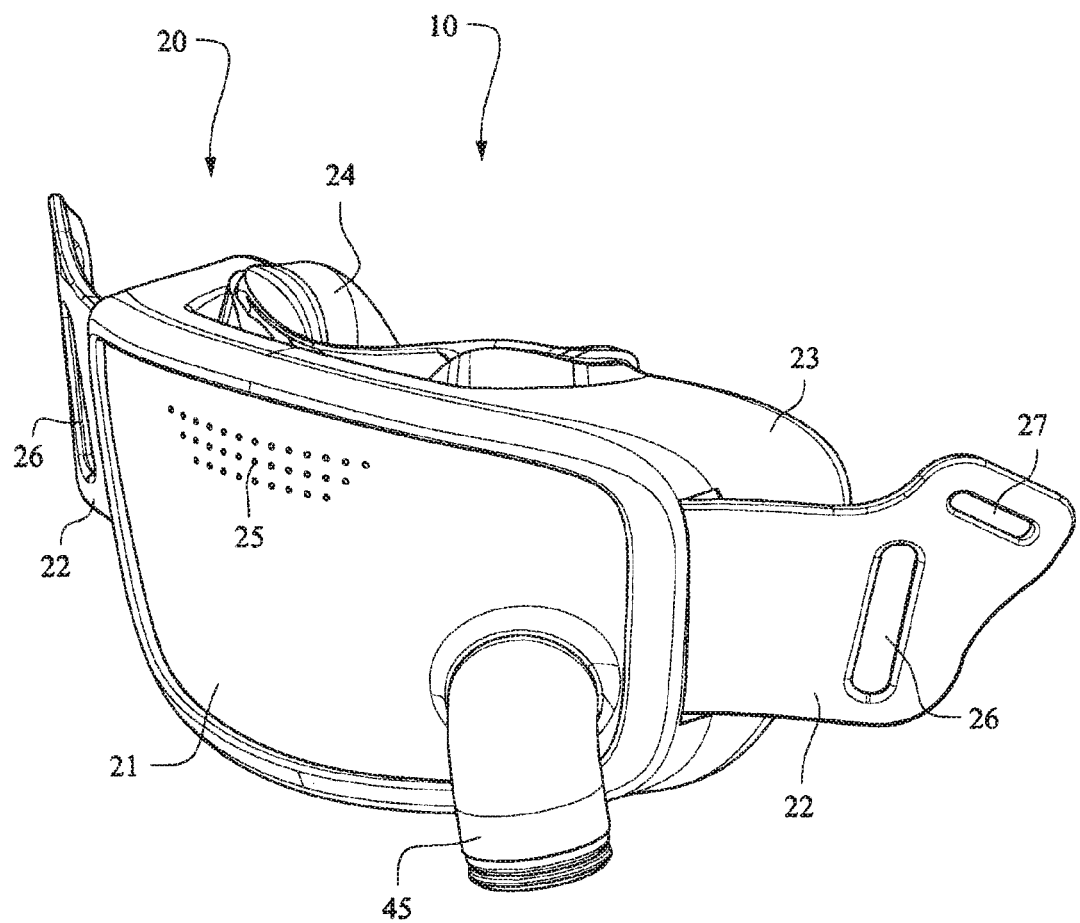
FIG. 48 is a front isometric view of the fascia, or front plate, including the elbow, and the seal (e.g. cushion) of the patient interface system of FIGS. 34-30.
Figure 49:
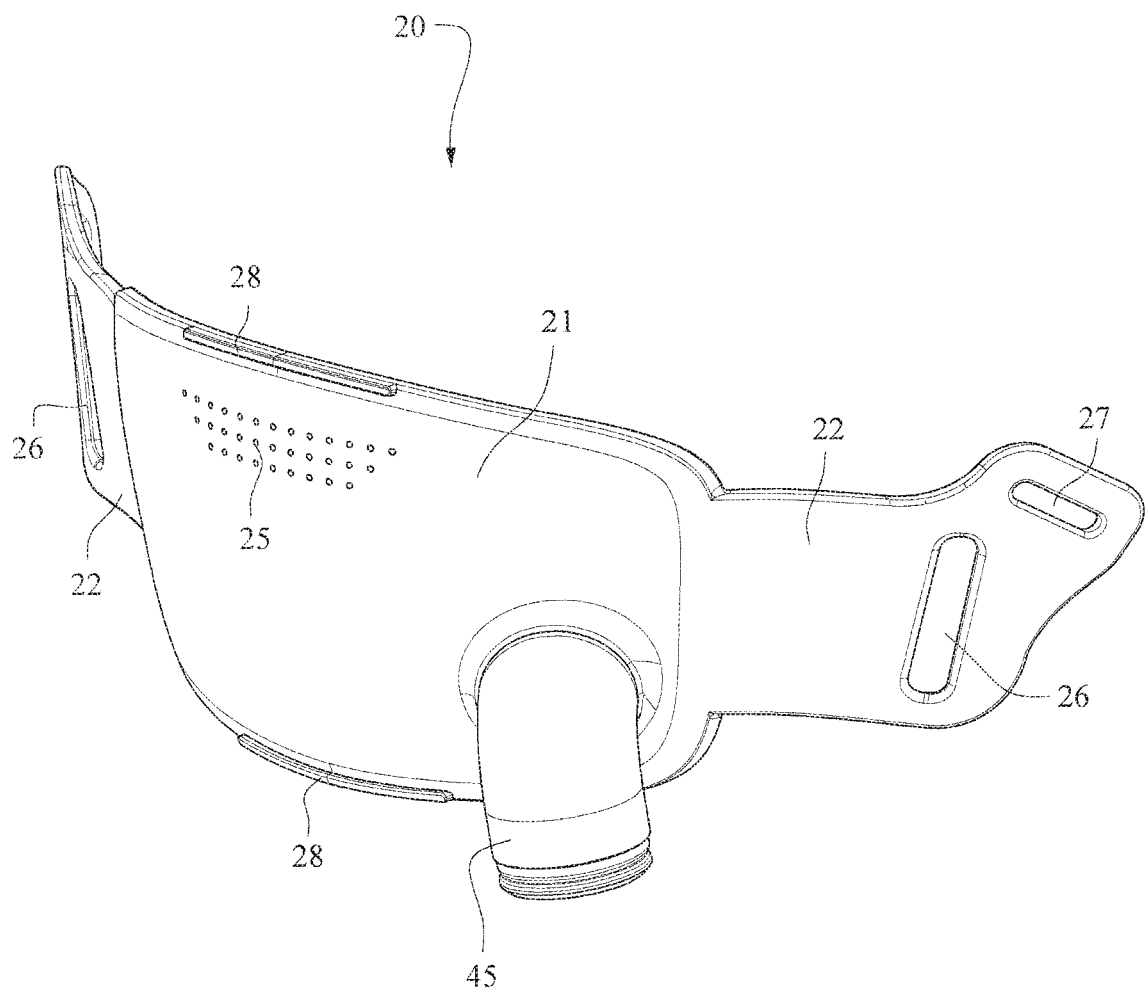
FIGS. 49-55 are front isometric, front, rear, right side, left side, top, and bottom views, respectively, of the fascia, frame or front plate, including the elbow, of the patient interface system of FIGS. 34-40.
Figure 50:
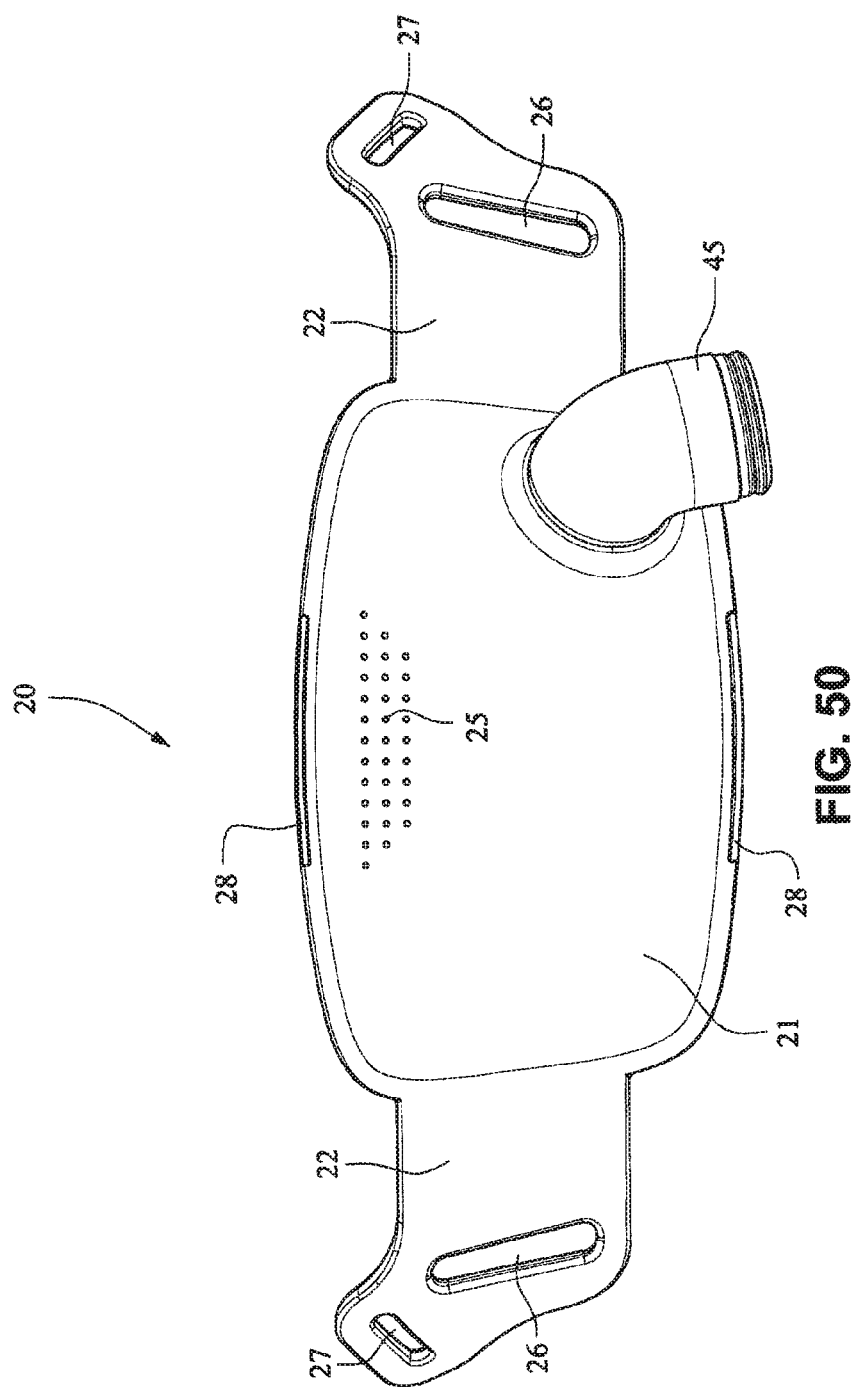
Figure 51:
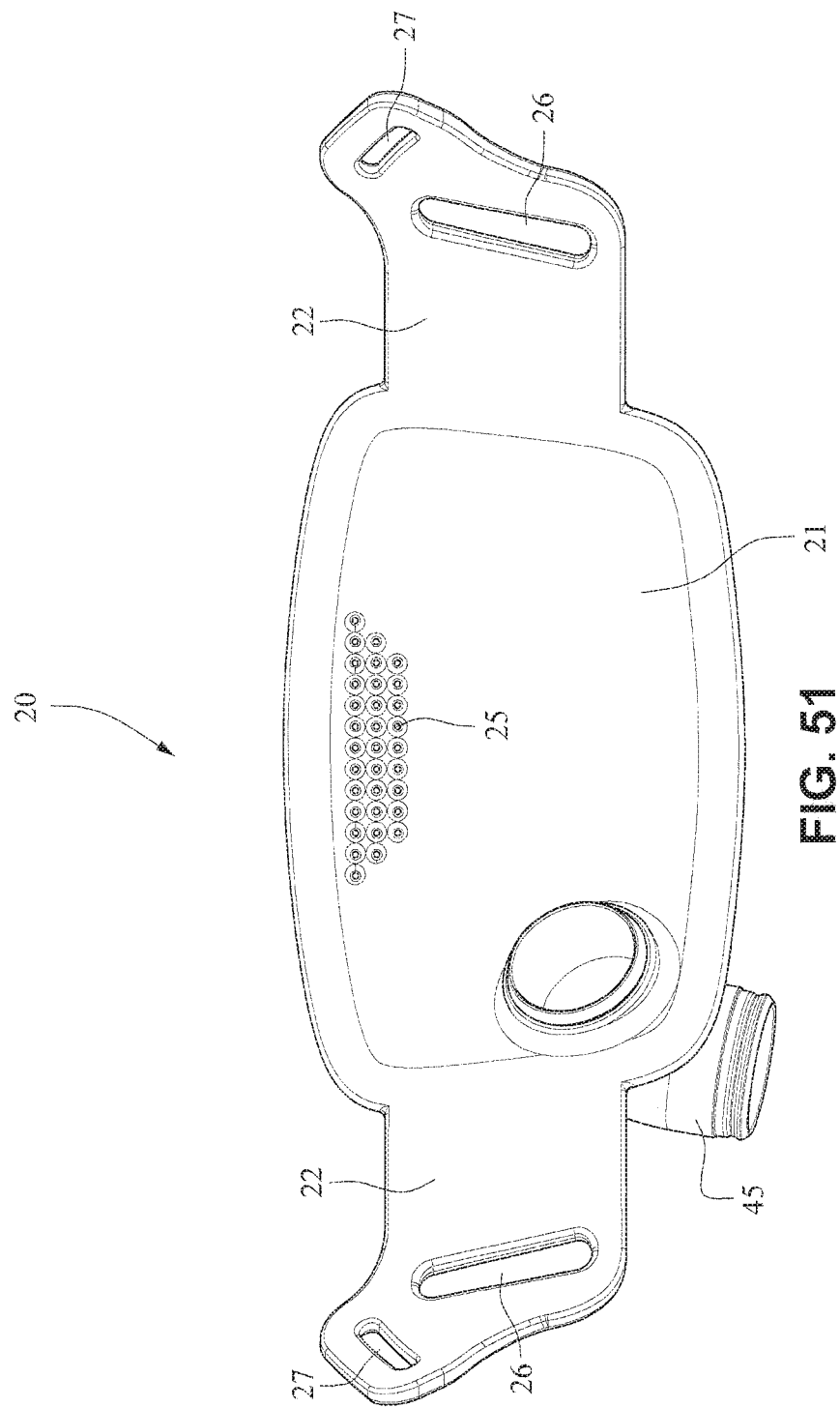
Figure 52:
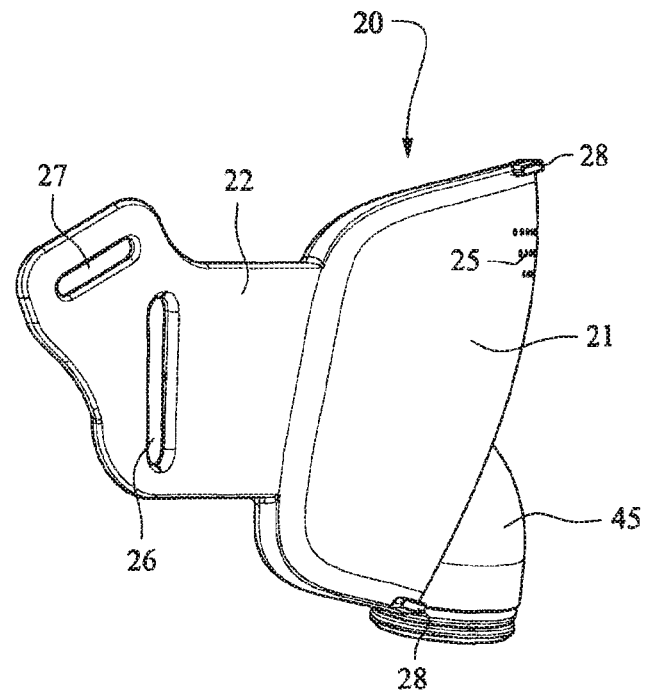
Figure 53:
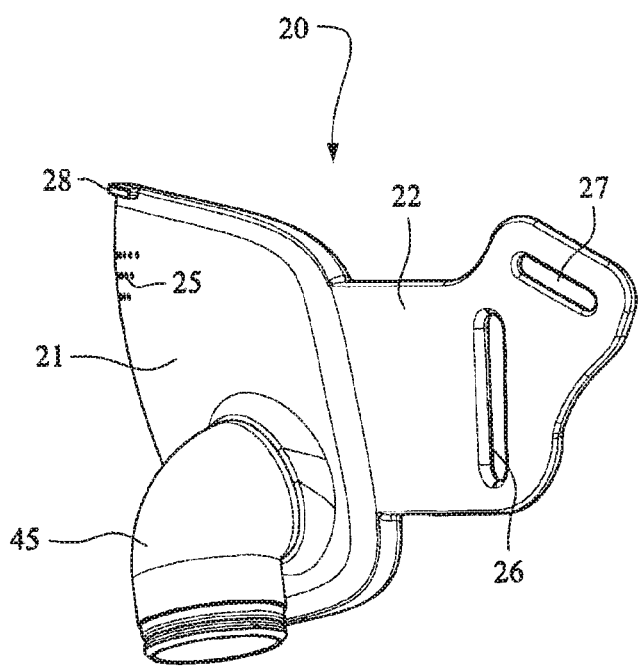
Figure 54:
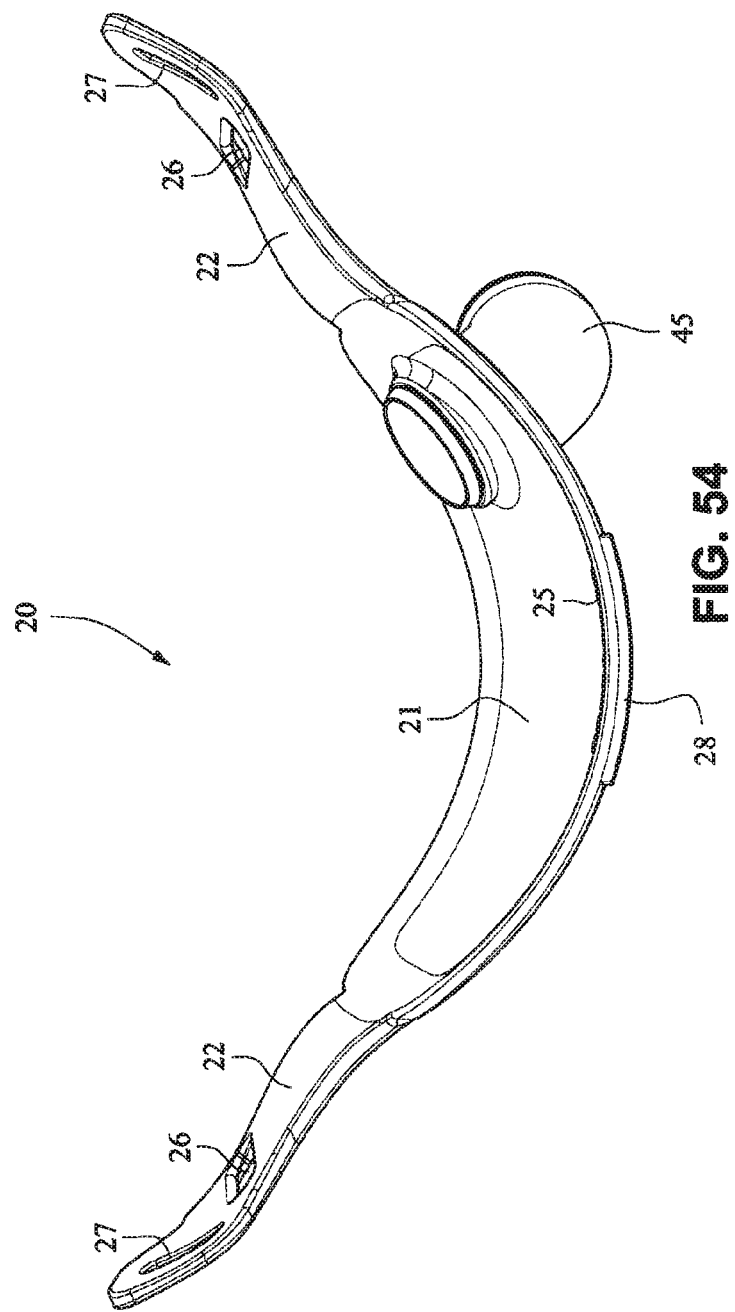
Figure 55:
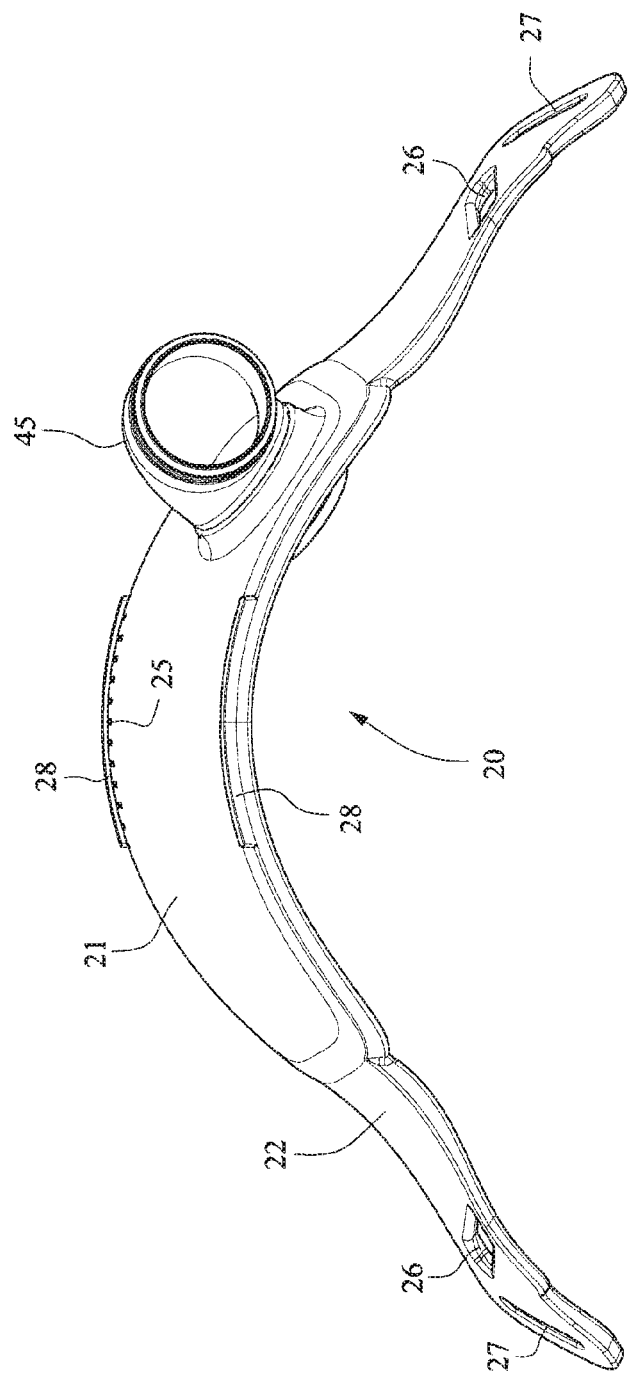
Figure 56:
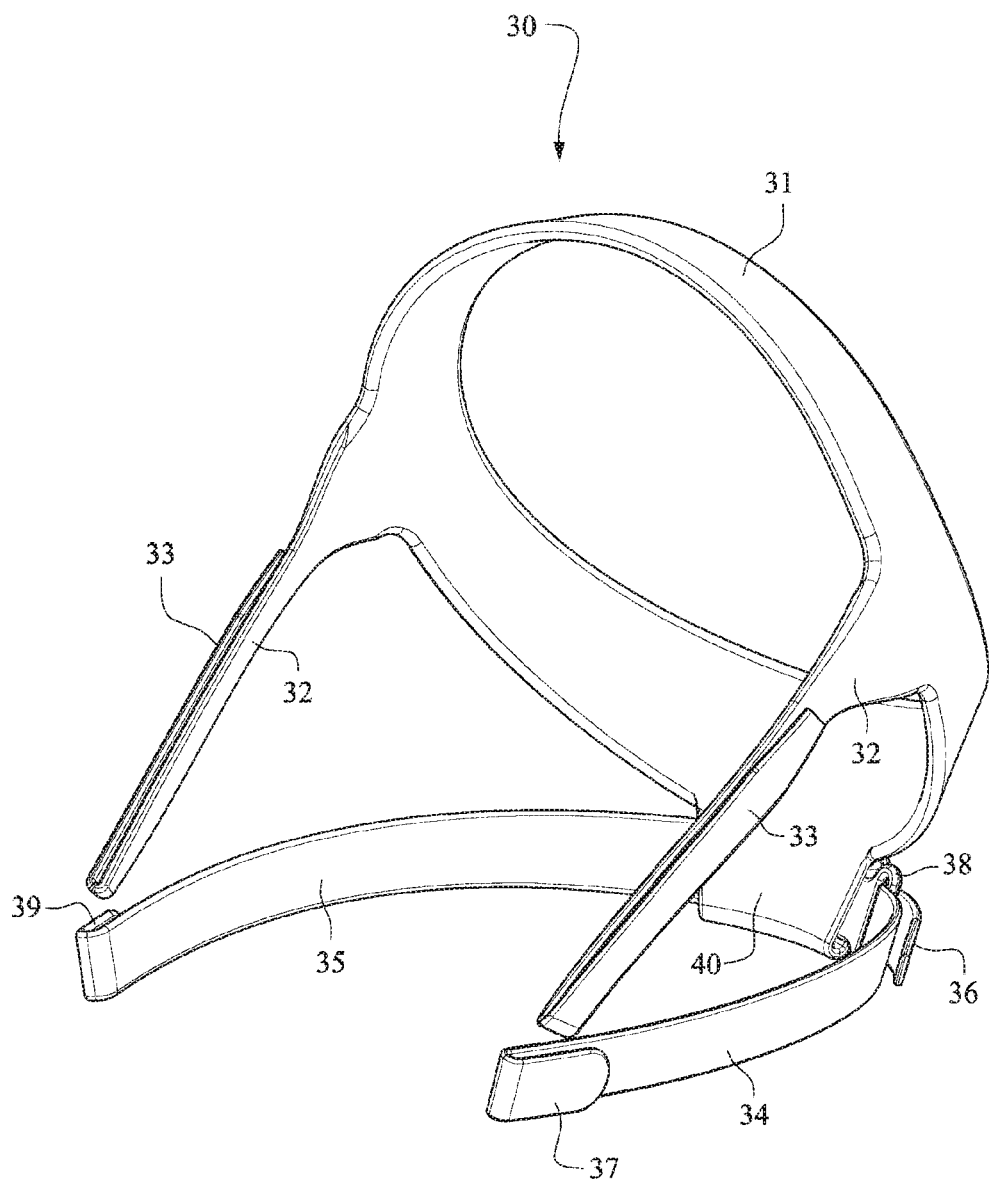
FIGS. 56-62 are front isometric, front, rear, rear isometric, right side, top, and bottom views, respectively, of a patient interface positioning system according to an example embodiment of the present technology.
Figure 57:
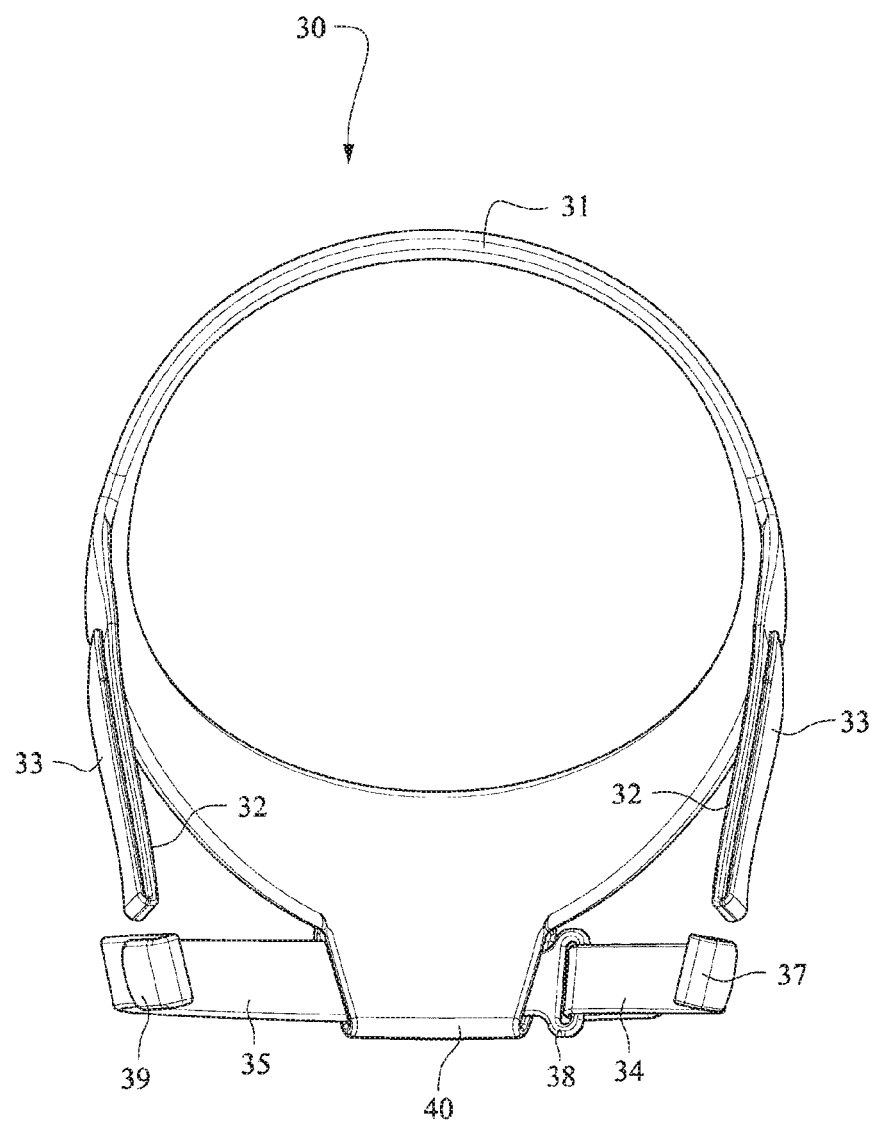
Figure 58:
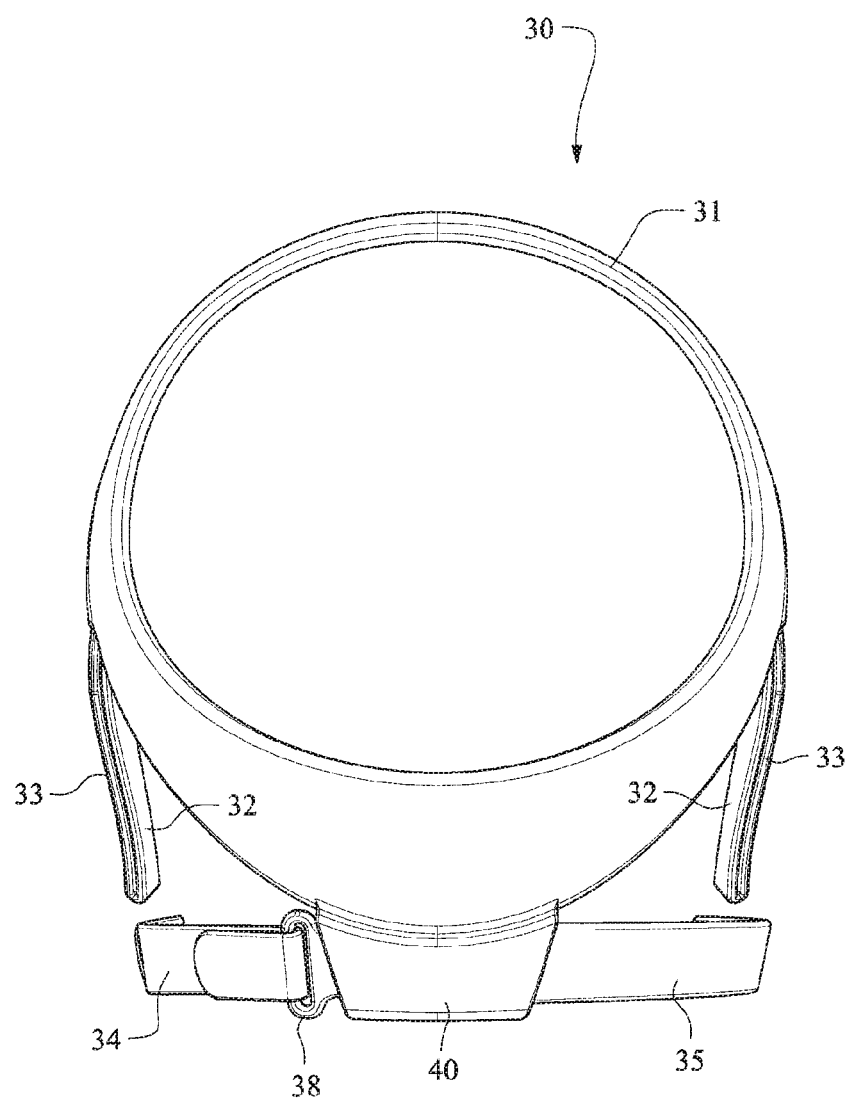
Figure 59:
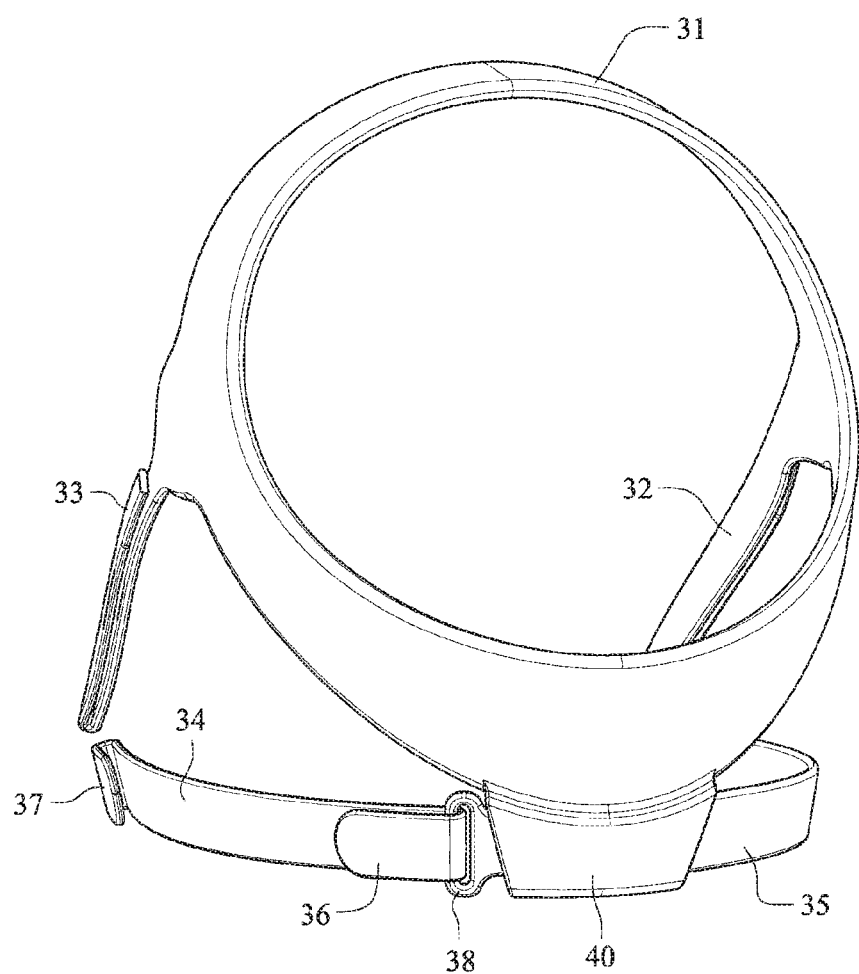
Figure 60:
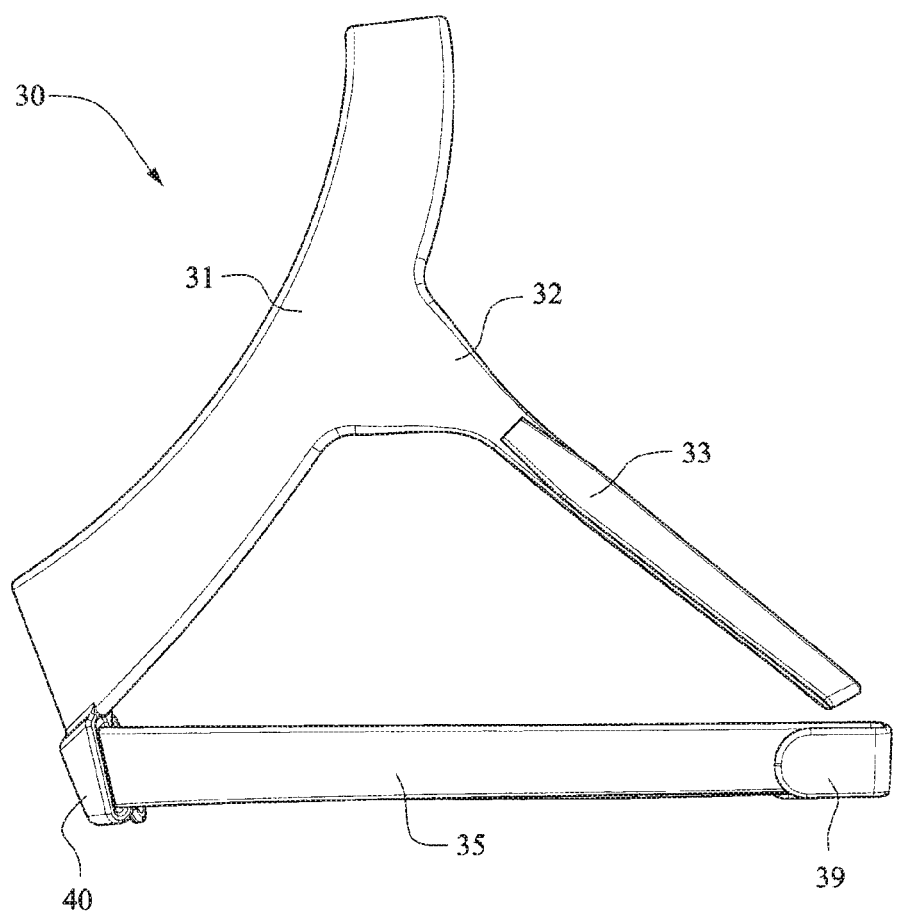
Figure 61:
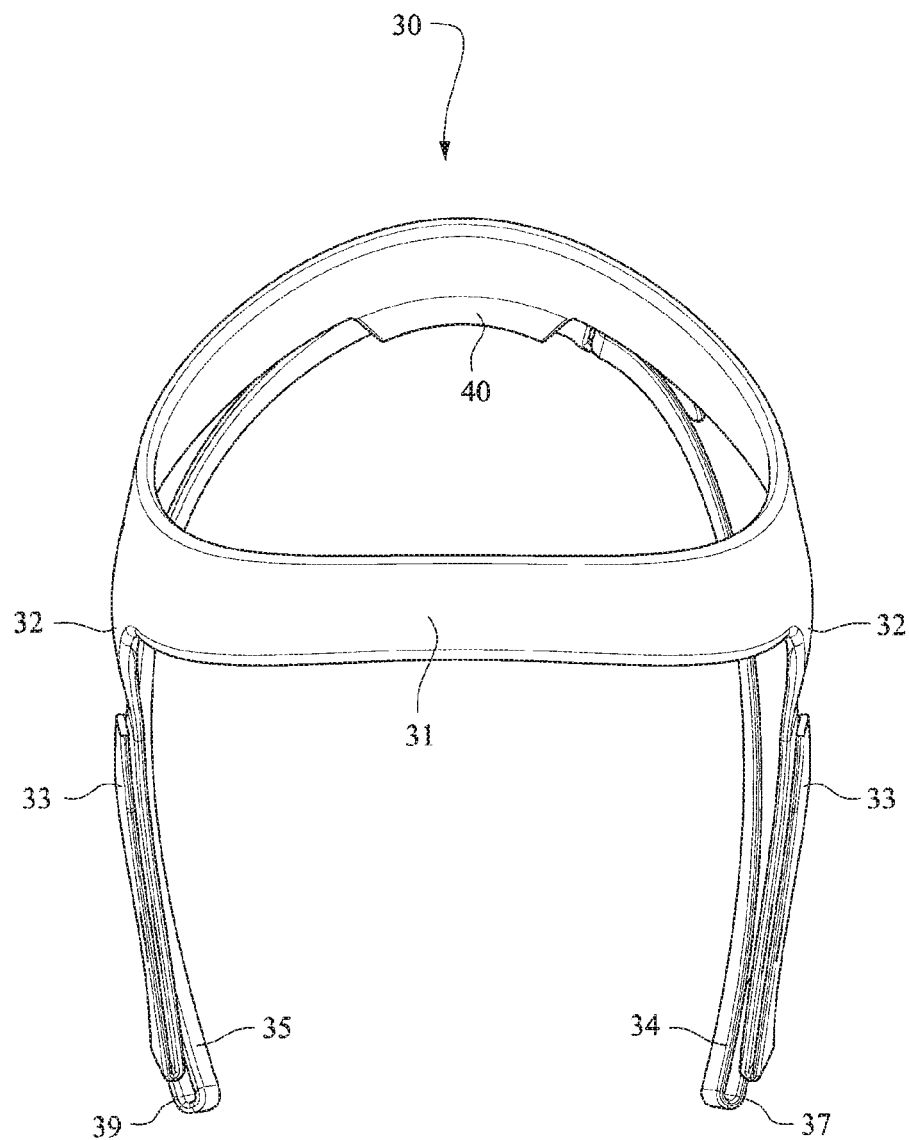
Figure 62:
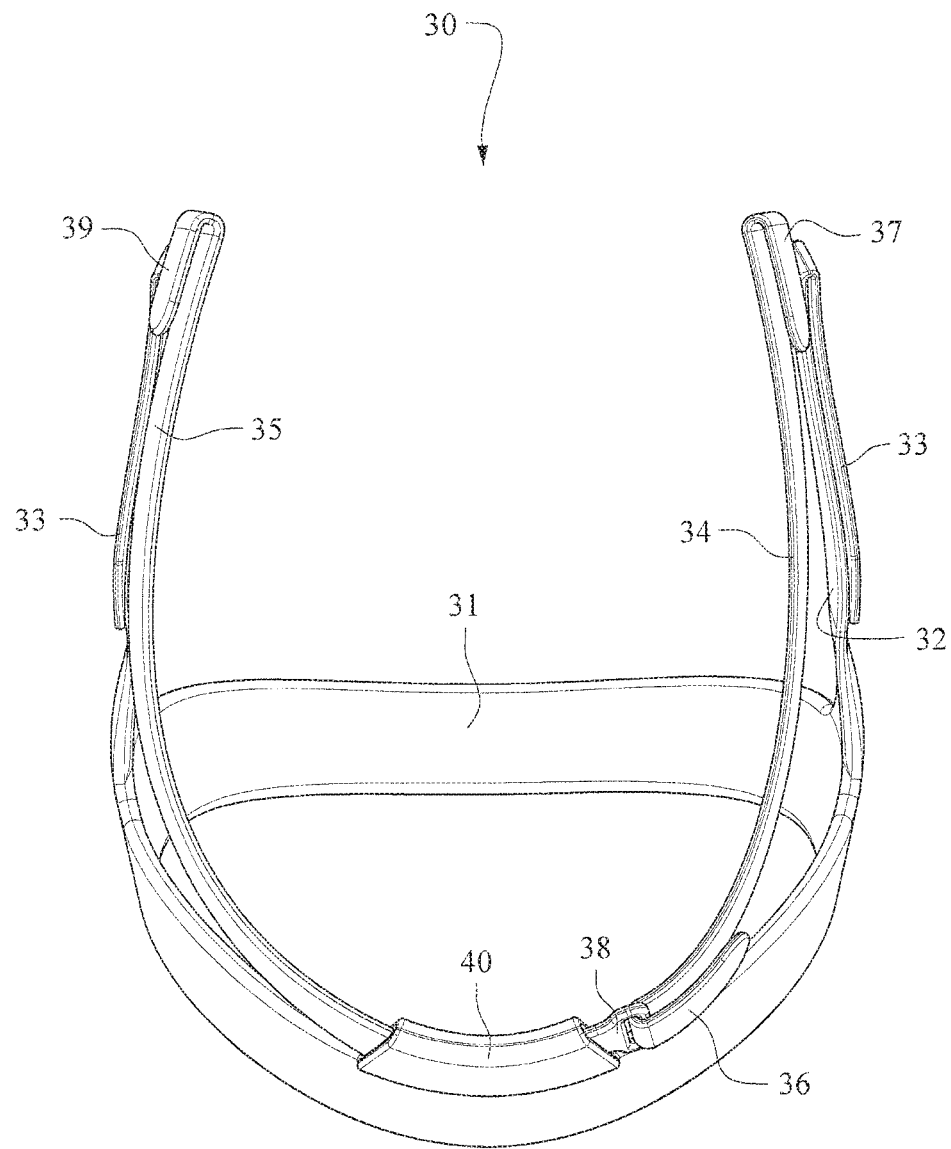
Figure 63:
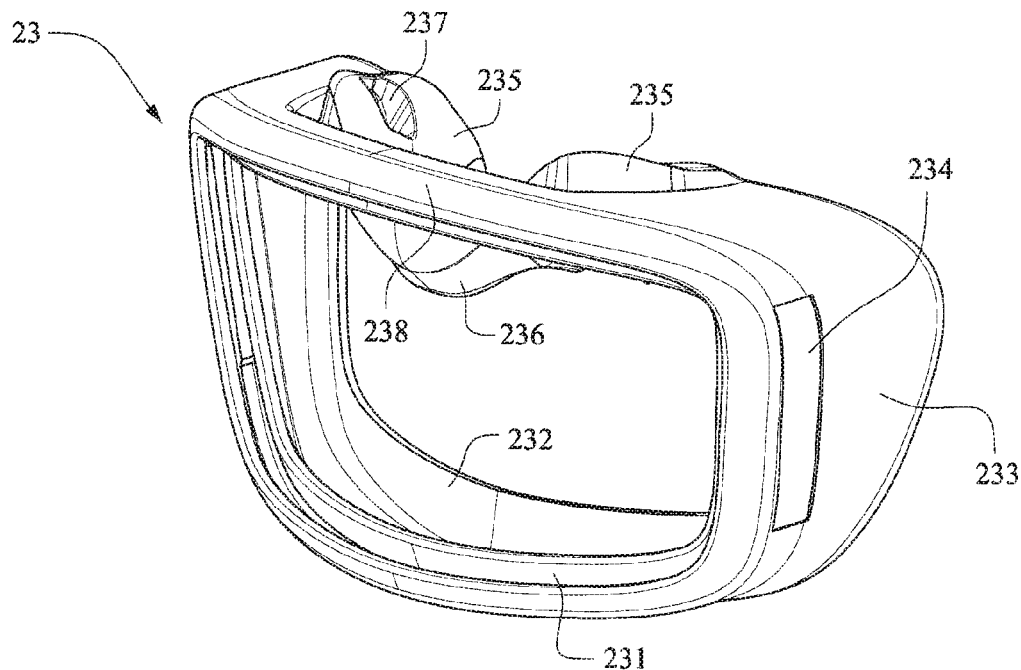
FIGS. 63-69 are front isometric, front, rear, top, bottom, right side, and left side views, respectively, of a mouth seal, or cushion, according to an example embodiment of the present technology.
Figure 64:
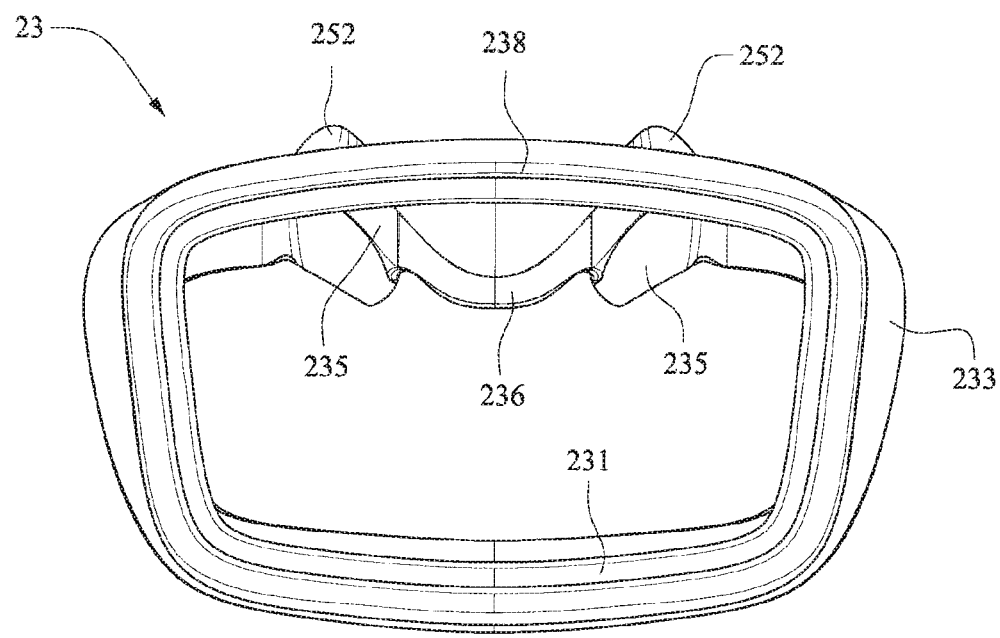
Figure 65:
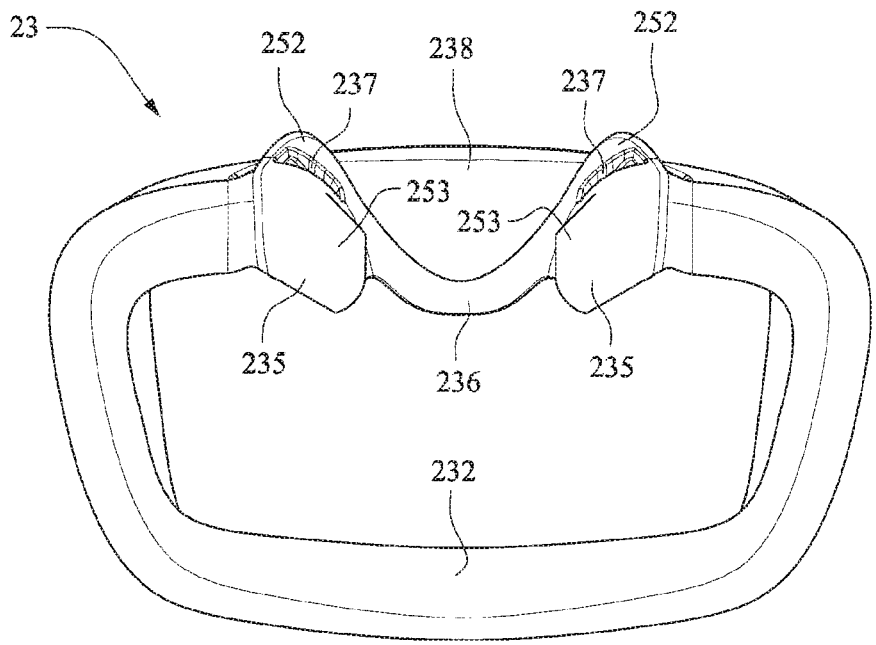
Figure 66:
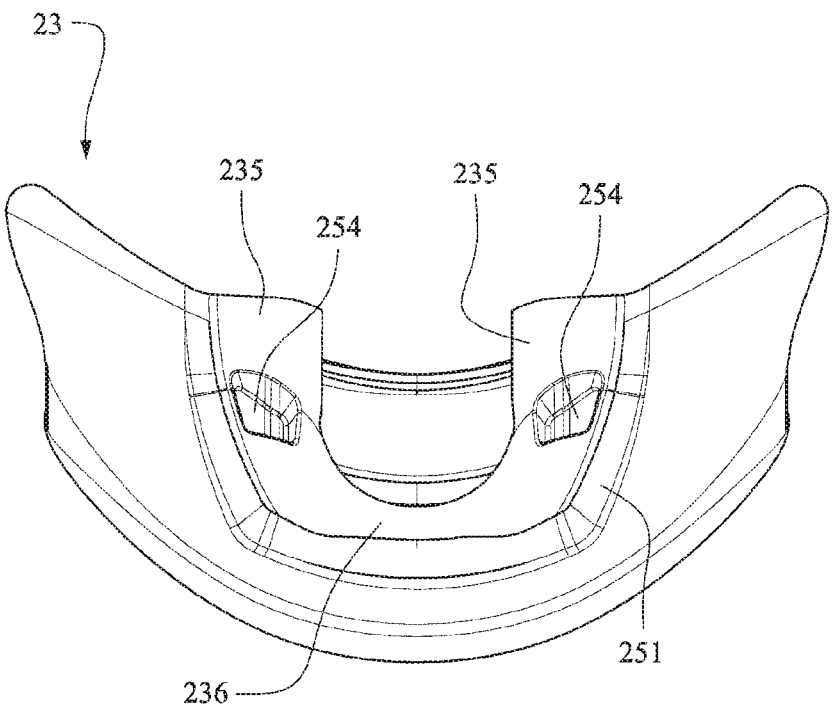
Figure 67:
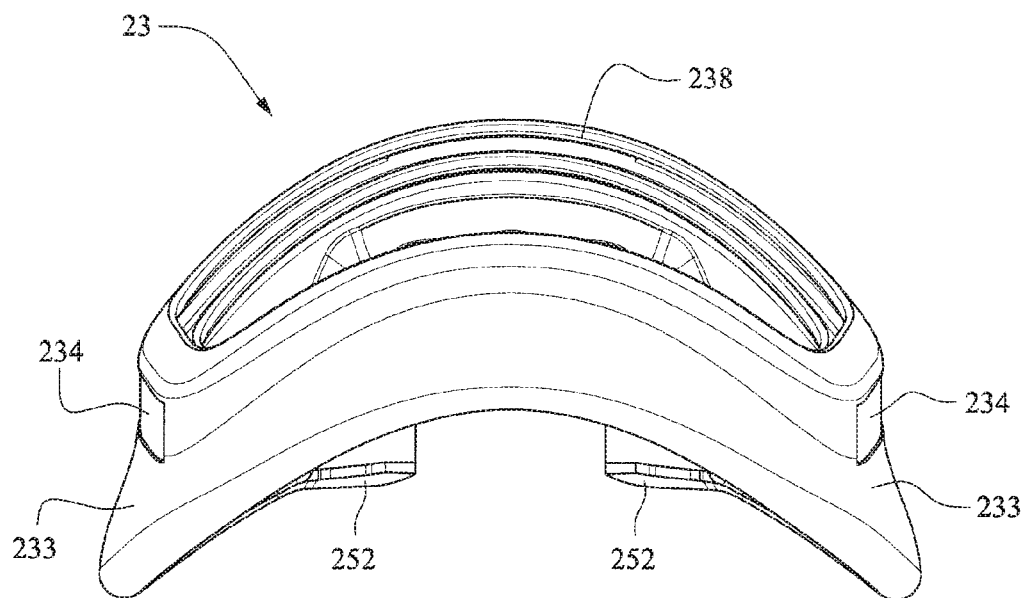
Figure 68:
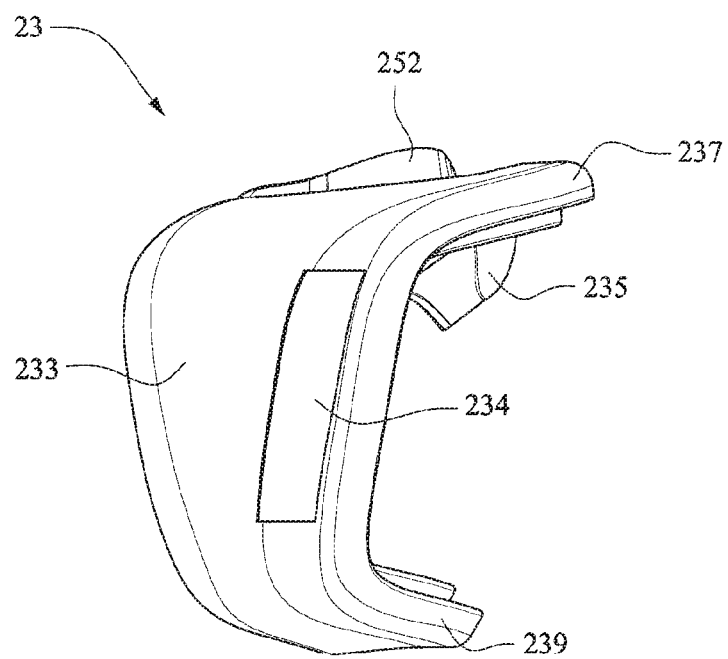
Figure 69:
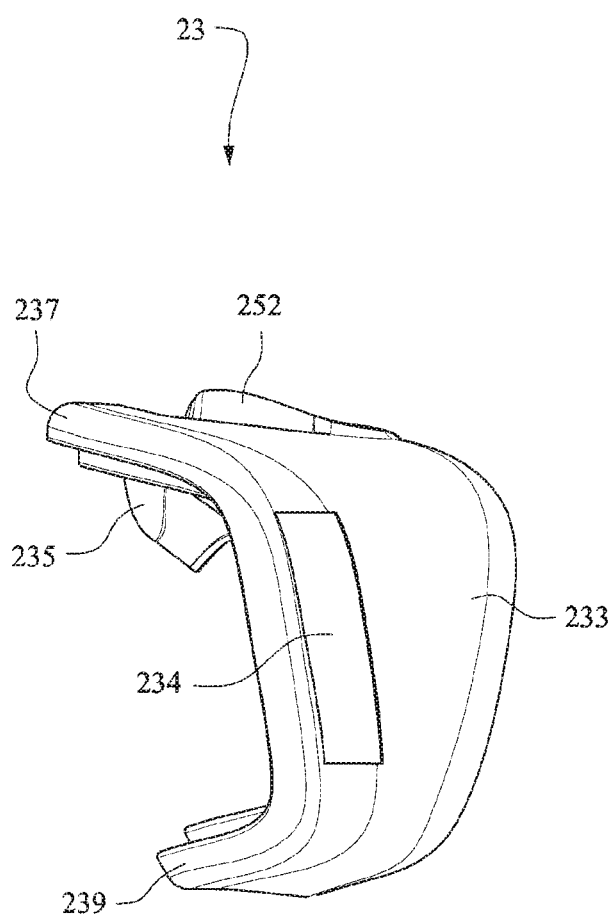
Figure 70:
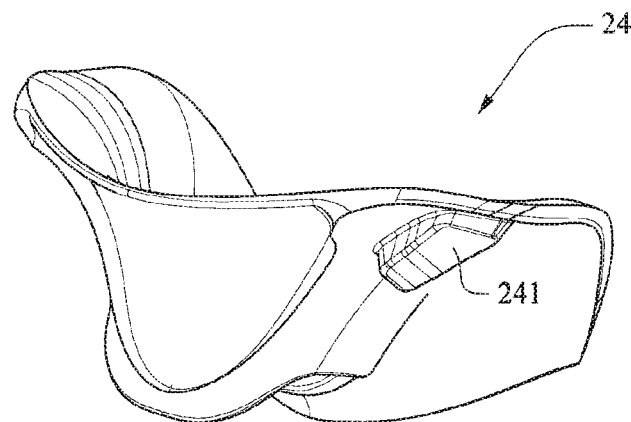
FIGS. 70-76 are front/bottom isometric, front, rear, top, bottom, side, and front/top isometric views, respectively, of a nasal seal, or cushion, according to an example embodiment of the present technology.
Figure 71:
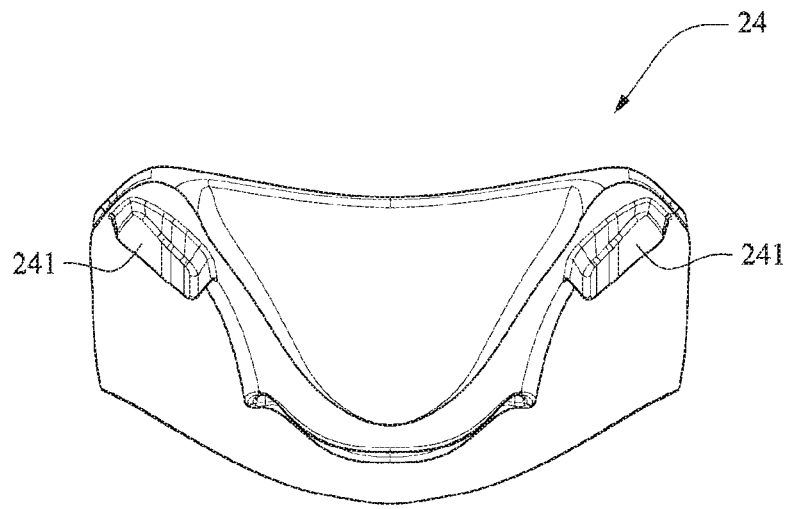
Figure 72:
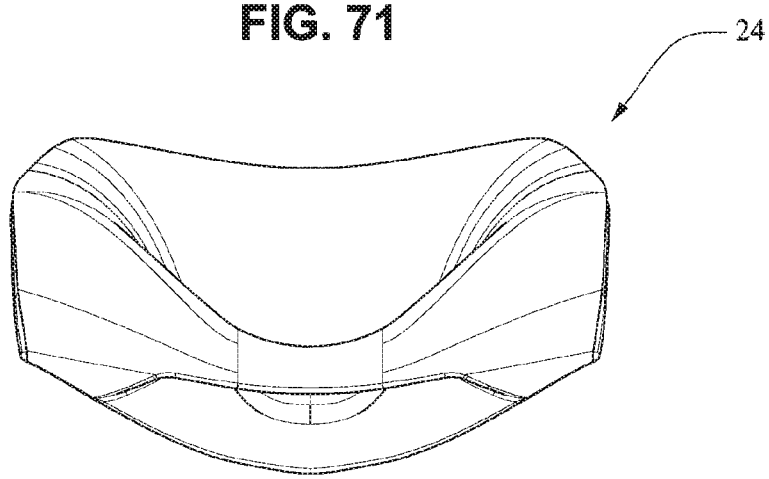
Figure 73:
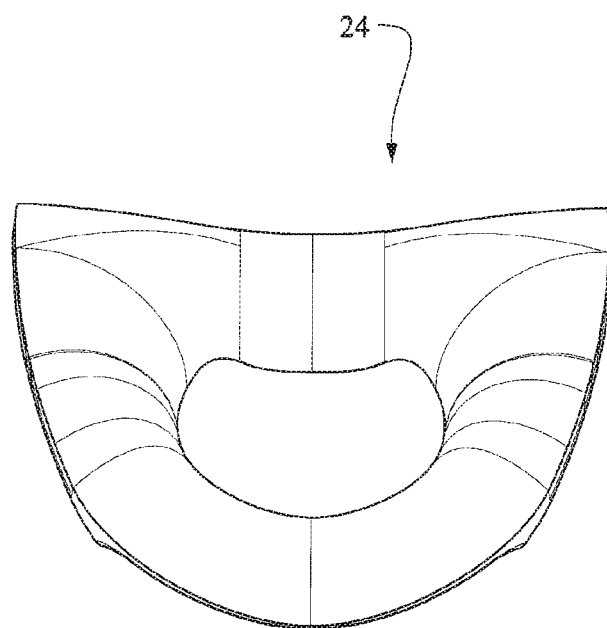
Figure 74:
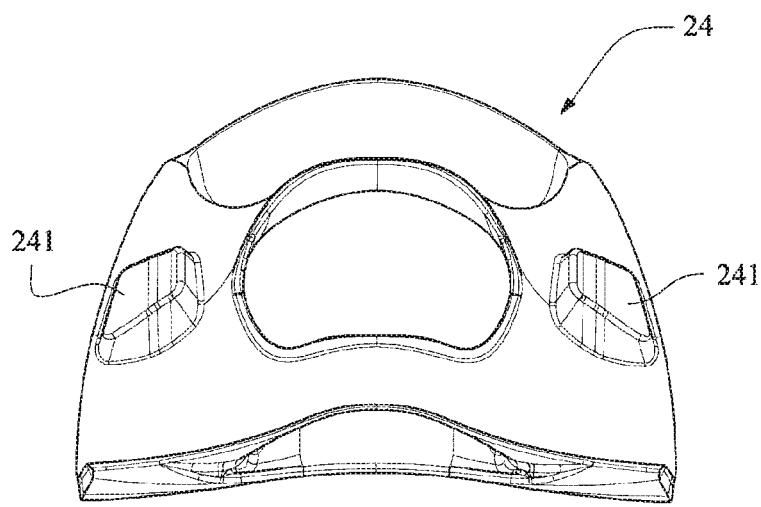
Figure 75:
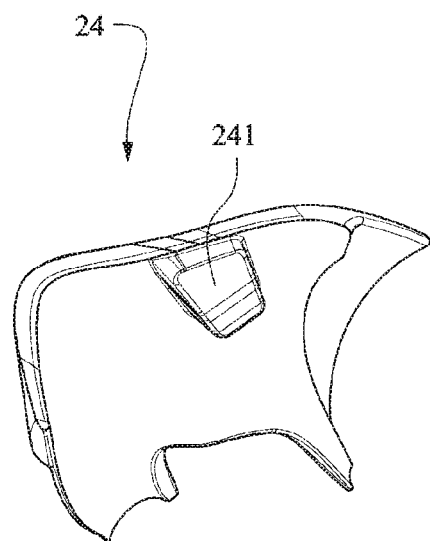
Figure 76:
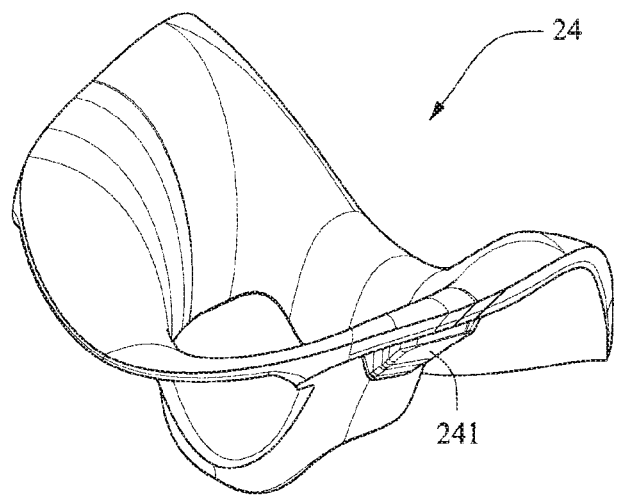
Figure 77:
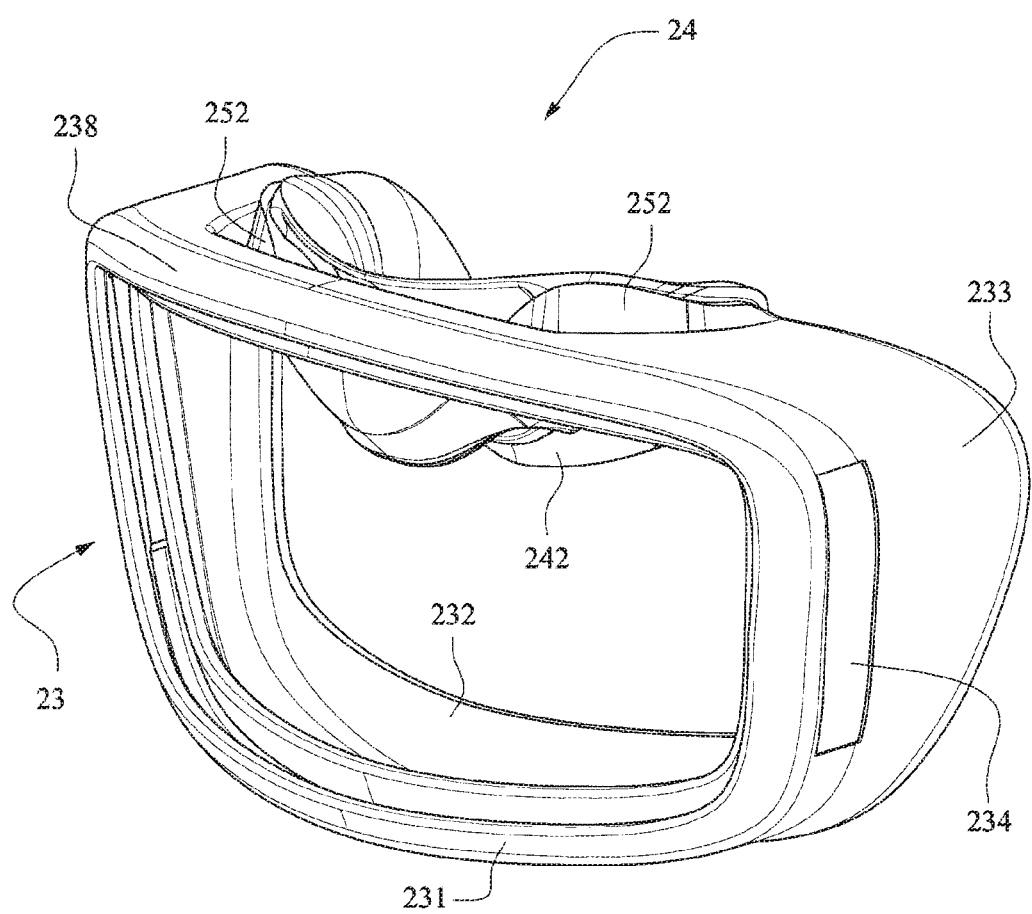
FIGS. 77-83 are front isometric, front, rear isometric, rear, right side, top, and bottom views, respectively, of a seal, or cushion, including the mouth and nasal seals, or cushions, of FIGS. 63-69 and 70-76, respectively, according to an example embodiment of the present technology.

As shown on FIGS. 14 and 15, the patient interface structure 20 may be generally rectangularly or trapezoidally shaped and comprise the front plate 21 that wraps across the face of the patient 1, and the cushion 23, 24 attached to the front plate 21. The cushion 23 may comprise the integrated mouth seal or cushion 23 and the nasal seal or cushion 24. The front plate 21 may be generally convex when viewed from the non-patient contacting side, curved or rounded shaped and adapted to follow the contour of the patient's face. The bottom side strap connector slots 26 and the top side strap connector slots 27 of the connectors 22 on either side of the front plate 21 may receive the headgear straps 32, 34, 35 and the tension or force from the headgear straps 32, 34, 35 may bend or flex the front plate 21 to conform to the shape of the patient's face. The top side strap connector slots 27 are directed generally upwards and are adapted to aid sealing of the nasal cushion 24 and direct the headgear away from the patient's eyes 4, and the bottom side strap connector slots 26 are adapted to aid sealing of the mouth cushion 23 and direct the headgear straps 34, 35 under the ears 2 of the patient 1.

The fascia or lens or front plate 21 is positioned in front of the patient's mouth, and is adapted to provide support to the other components of the patient interface system 10 and aid in positioning these other components, for example the front plate has headgear connectors 22 and a cushion connection portion adapted to receive the patient interface positioning system 30 and a cushion 23 and position these components relative to one another. The front plate 21 also provides some structure to the patient interface system 10 due to the comparatively greater rigidity of the front plate 21 when compared to the cushion 23.

The front plate 21 may take the form of a lens made from a clear material such as nylon, polycarbonate or nearly clear material such as polypropylene. The lens may be shaded, selectively shaded (e.g. gradient, patterned, random assortment of shapes), printed on or otherwise coloured. The lens may also have colour changing properties e.g. it may be clear when the light is on, and may be opaque when the light it off. The lens may also be customizable. The lens may be provided with a skin or adhesive layer that may customize or otherwise alter the lens. The lens may be surface treated e.g. frosted. The lens may be die cut, drape formed, vacuum formed, molded, cast, ultrasonically cut or formed in any other method to create the desired shape. The lens may also be formed with vent holes. The vent holes may be molded in, laser cut or otherwise formed with the lens. The lens may be flexible or capable of being shaped to fit the patient's face.

Cushion/Seal

Referring to FIGS. 63-83, the cushion or seal of the patient interface system may comprise two components the mouth cushion or seal 23 and the nasal cushion or seal 24. The cushions 23, 24 may be molded together or otherwise permanently attached (e.g. glue, weld). The mouth cushion 23 provides the mouth sealing portion and also the support for the nasal cushion 24. The mouth cushion 23 also connects to the front plate 21. The nasal cushion 24 is a nares sealing portion that may be molded from the same or alternative material to mouth cushion 23. Separating the cushion into two components allows use of a lower durometer (i.e. lower hardness) material for the nasal seal or cushion 24, and the tooling required to mold the nasal seal or cushion 24 with the mouth seal or cushion 24 is difficult, so molding them in two steps rather than one facilitates manufacturing.

The cushions 23, 24 may be made from a single material such as silicone, TPE, TPU. However, combinations of materials and/or hardnesses of materials may be used. For example, the mouth seal or cushion 23 may have a TPE or silicone body, with a seal portion or flap adapted to interface with the patient. The nasal seal 24 may comprise a seal portion formed of an alternative material, for example a lower hardness silicone, TPU, fabric, etc.

Referring to FIGS. 63-69, the mouth cushion 23 comprises a groove or channel 231 around a front portion 238 that is adapted to receive the front plate 21. The channel 231 may have a flap (e.g., a sealing wall such as a single wall seal or multiple wall seal) 232 around the inner side of the channel that is adapted to seal against the face of the patient around the patient's mouth. The flap 232 may comprise a single wall seal, although it should be appreciated that the flap 232 may comprise more than one wall, for example two or three walls. The mouth cushion 23 may be constructed from a deformable material such as TPE, TPU, silicone, foam (skinned or unskinned), or gel.

It should be appreciated that the mouth cushion 23 may be insert, over, or co-moulded to the front plate 21. It should be further appreciated that a cushion clip may be provided to the cushion to clip to the front plate 21. The clip may be insert, over, or co-moulded into the cushion 23 as one part. The cushion clip may add stiffness and rigidity to the cushion 23 where required, provide patient interaction points, and allow for a locating and attaching method of the cushion 23 to the front plate 21, e.g. the cushion clip may snap onto the front plate 21. The cushion clip may simplify the process of attaching the cushion 23 to the front plate 21 by reducing stretching and warping of the cushion 23 during assembly.

Slots 234 are provided in side walls 233 of the cushion 23 and are adapted to receive the connectors 22 of the front plate 21. Slots 234 may be generally rectangular, however any other shape may be possible, such that slots 234 may be complimentary to the shape of connectors 22. Connectors 22 may sealingly engage with side walls 233, for example side walls 233 may comprise a lip seal or other arrangement adapted to seal against connectors 22.

The upper portion 237 of the mouth seal or cushion 23 has a greater depth when compared with the lower portion 239 of the mouth seal or cushion 23, i.e. the distance of the seal portion to the clip portion of the upper portion may be longer than the distance from the seal portion to the clip portion of the lower portion, to tilt the cushion 23 when in use to reduce the profile of the mask 20 when in use. The upper portion 237 of the mouth seal or cushion 23 may also have a greater depth than the lower portion 239 to accommodate nasal seal or cushion 24 and patients with long noses.

Flaps 252 are provided on nares support portions 235 to assist in positioning and stabilizing the nasal seal or cushion 24 to engage with the sides of the patient's nose or the patient's top lip. Raised portions 253 on the nares support portion 235 aid in positioning the nasal seal 24 against the flares of the patient's nostrils. Indents or apertures 254 are formed in the nasal support portions 235 and are adapted to receive lugs 241 on nasal seal or cushion 24 to aid in alignment.

A channel 251 may be provided around the nares support portions 235 to form a flexible region (e.g. could be localized thinning of material) adapted to permit movement of the nasal seal or cushion 24 to accommodate varying anthropometrics.

The side walls 233 of the mouth seal or cushion 23 may have a "question mark" cross section, i.e. the mouth seal portion does not have a straight wall section but rather has a gusseted side wall that acts as a built-in spring so that the mouth seal portion can flex to fit varying patient anthropometrics. Such a side wall cross section is disclosed in, for example, U.S. Patent Application Publication 2008/0110464 A1, the entire contents of which are incorporated herein by reference.

The front portion 238, the side walls 233 and the flap 232 of the mouth cushion 23 may have different hardnesses. For example, the front portion 238 may have a Shore A durometer of about 30-50, for example about 40. The side walls 233 and/or the flap 232 may have a Shore A durometer of 5-10, for example about 7.

Figure 104:
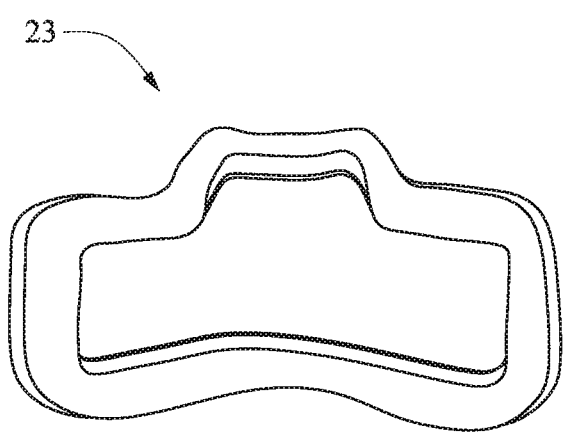
FIG. 104 is a rear view of a mouth seal, or cushion, according to an example embodiment of the present technology.
Figure 105:
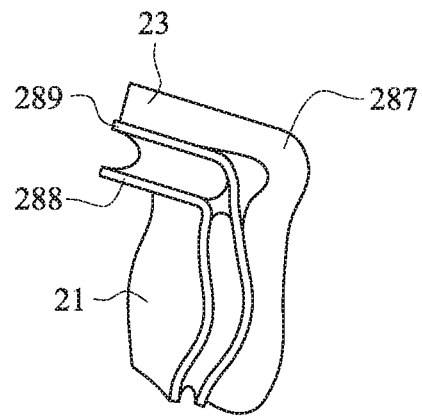
FIG. 105 is a left side view of the mouth seal, or cushion, of FIG. 104.

Referring to FIGS. 104 and 105, the cushion or seal may be formed of a foam, gel, or low durometer material to seal with the patient. Two gusset or spring portions 288, 289 may be formed behind the seal portion to aid in adjustment of the positioned of the seal portion. The corner 287 of the nose region may be raised to ensure the seal abuts the patient's face and seals in this region.

Figure 108:
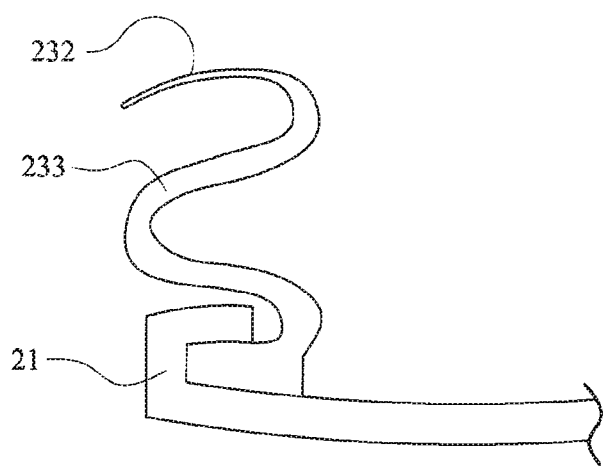
FIG. 108 is a schematic illustration of a fascia, or front plate, and a seal, or cushion, including a gusseted side wall according to an example embodiment of the present technology.
Figure 109:
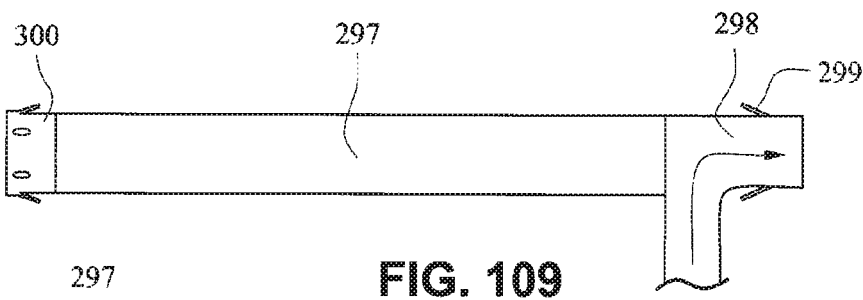
FIG. 109 is a schematic illustration of a strap, for example a rear strap, of a patient interface positioning system (e.g. headgear) according to an example embodiment of the present technology.
Figure 110:
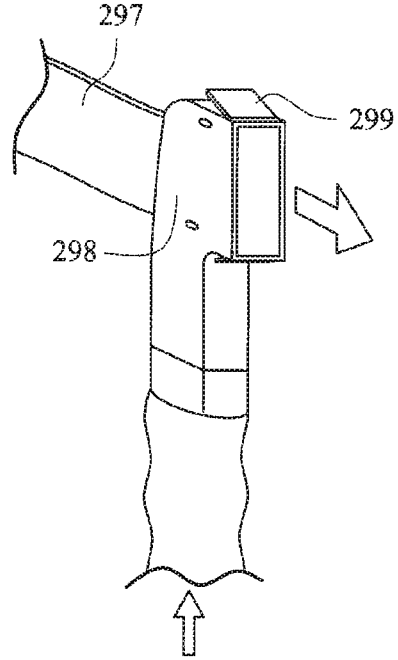
FIG. 110 is schematic illustration of the strap of FIG. 109 connected to a delivery tube or conduit or hose.

Referring to FIG. 108, a gusset type arrangement may be provided to permit flexibility of the cushion and aid sealing under air pressure, with the flap 232 turning outwards. This arrangement may increase the fit range.

Referring to FIGS. 70-76, the nasal seal or cushion 24 may comprise lugs 241 adapted to be received in indents 254 of the nare support portions 235 of the mouth seal or cushion 23. The nasal seal or cushion 24 may have a geometry the same as or similar to that disclosed in, for example, WO 2010/139014 A1, the entire contents of which are incorporated herein by reference. The nare support portions 235 and the cradle wall 236 form a trampoline type join with the nasal seal or cushion 24. The nasal seal or cushion 24 may have a Shore A durometer of about 30-50, for example about 40. The nasal seal or cushion 24 may have a Shore A durometer of about 5-10, for example about 7.

Figure 78:
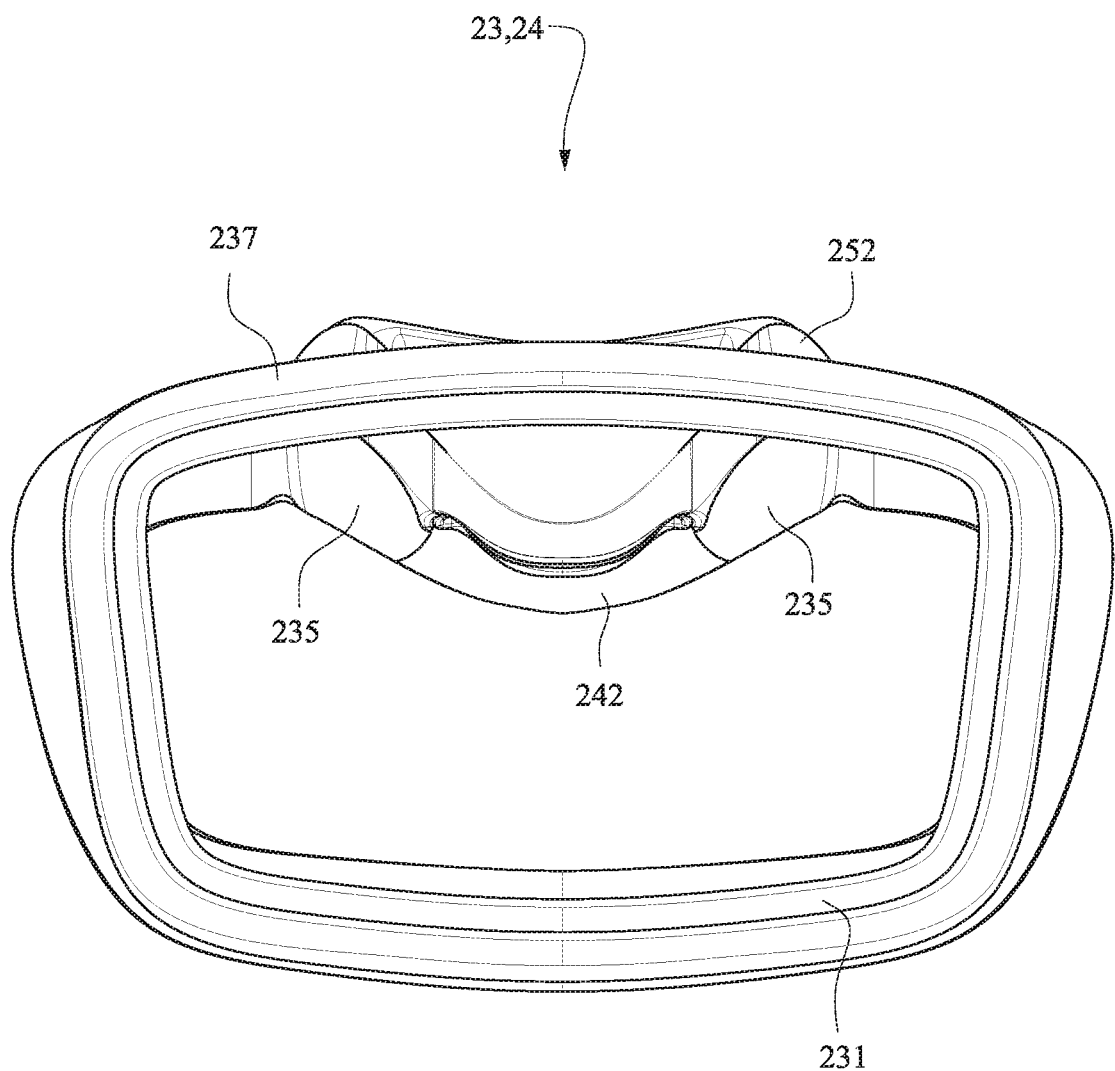
Figure 79:
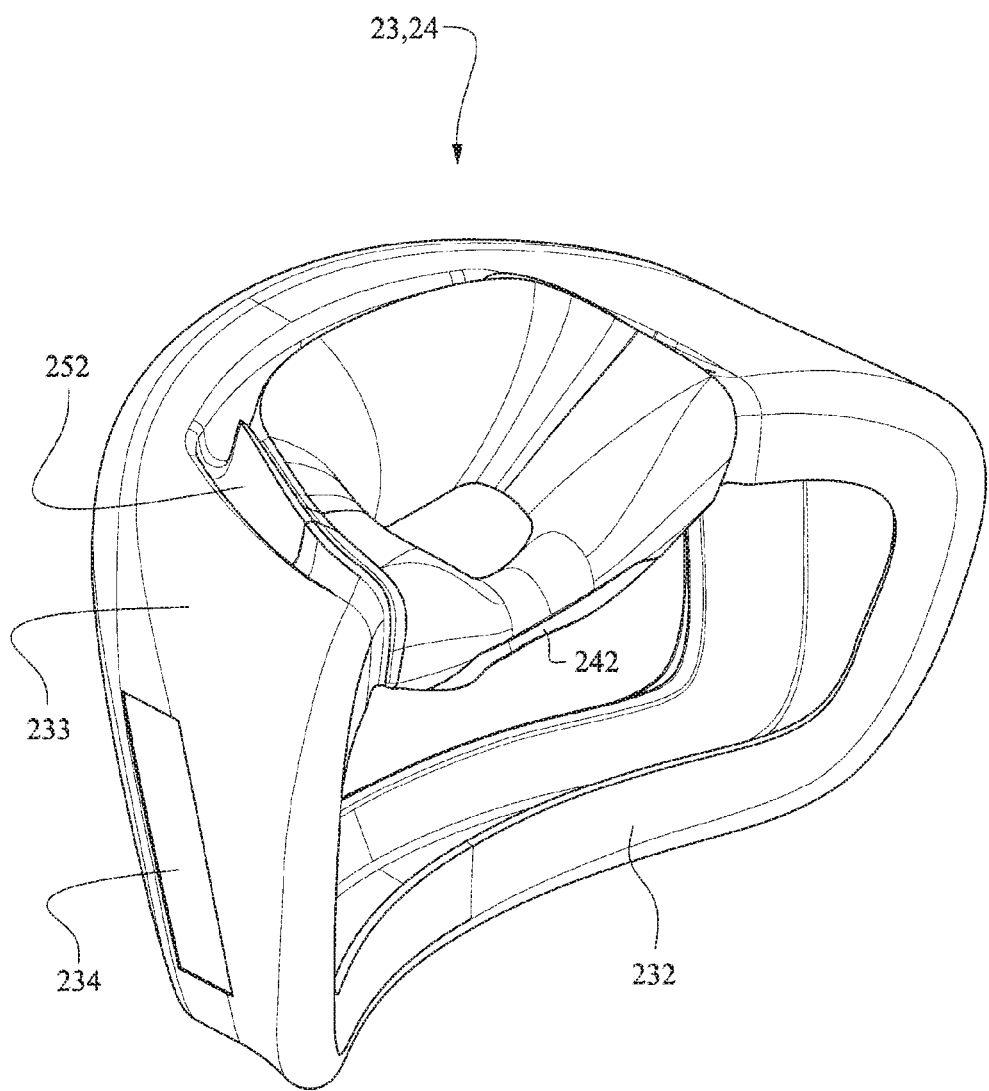
Figure 80:
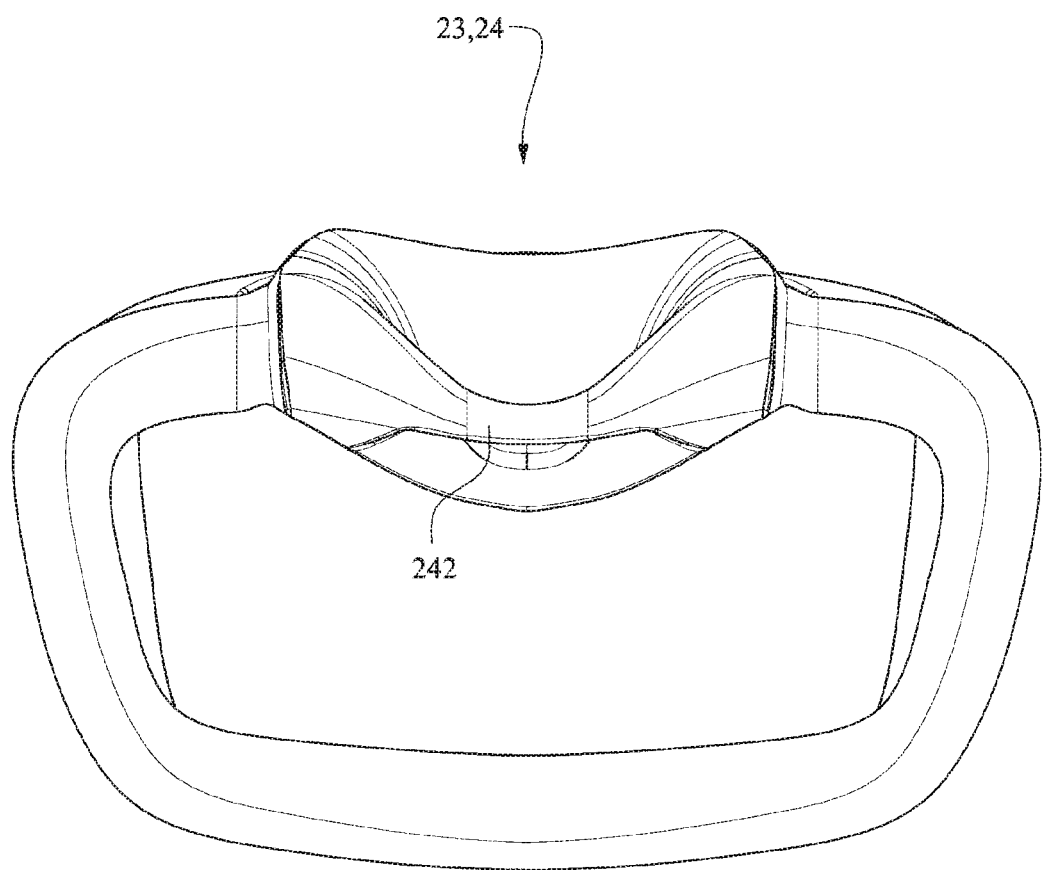
Figure 81:
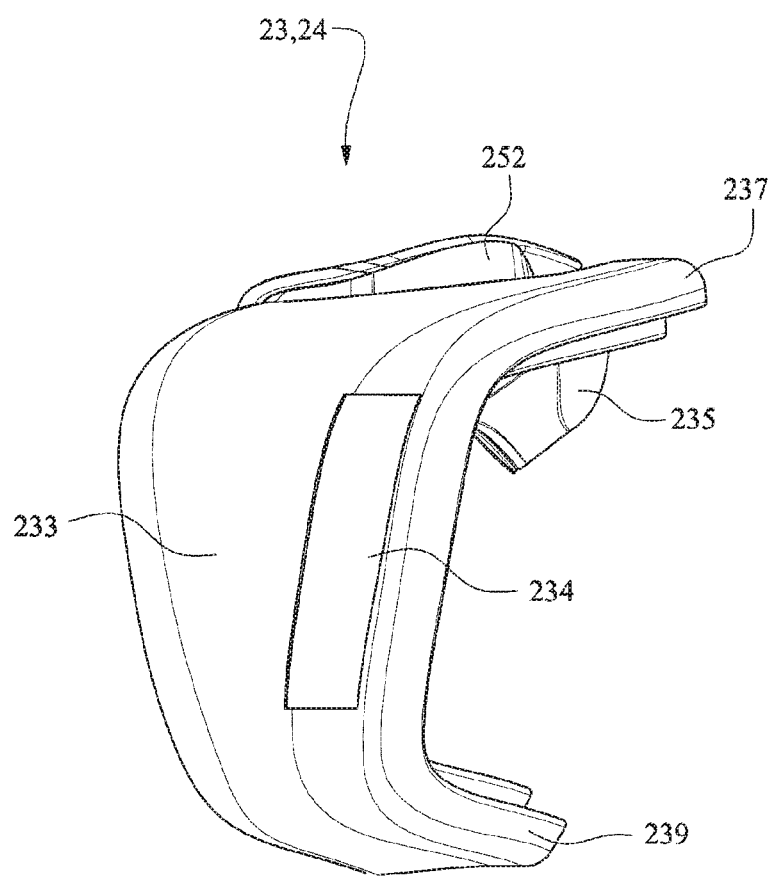
Figure 82:
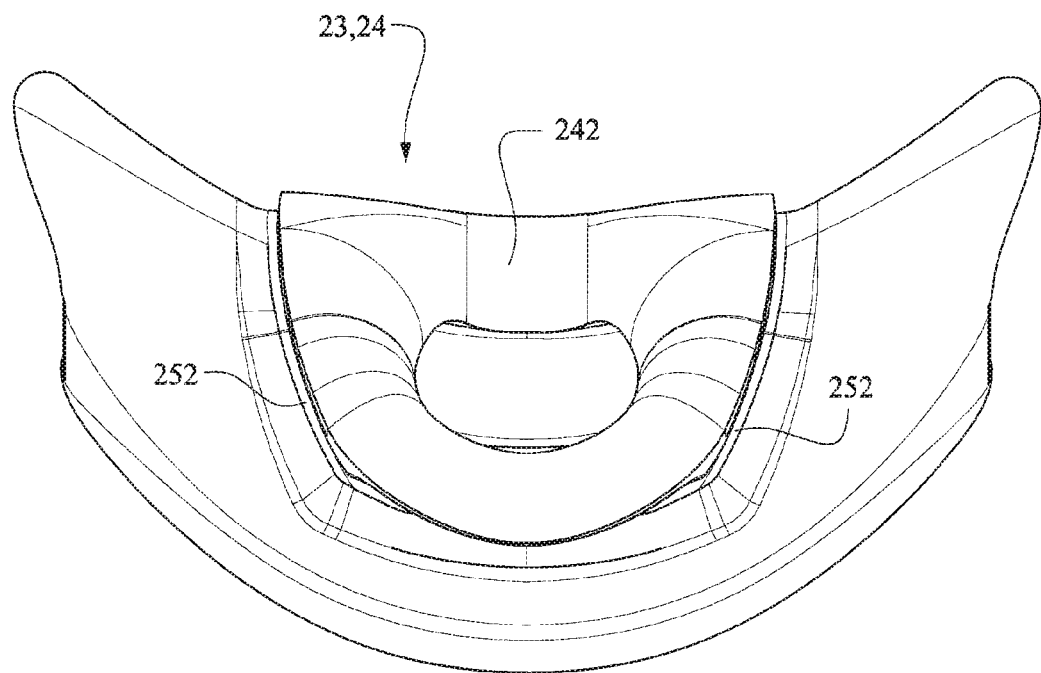
Figure 83:
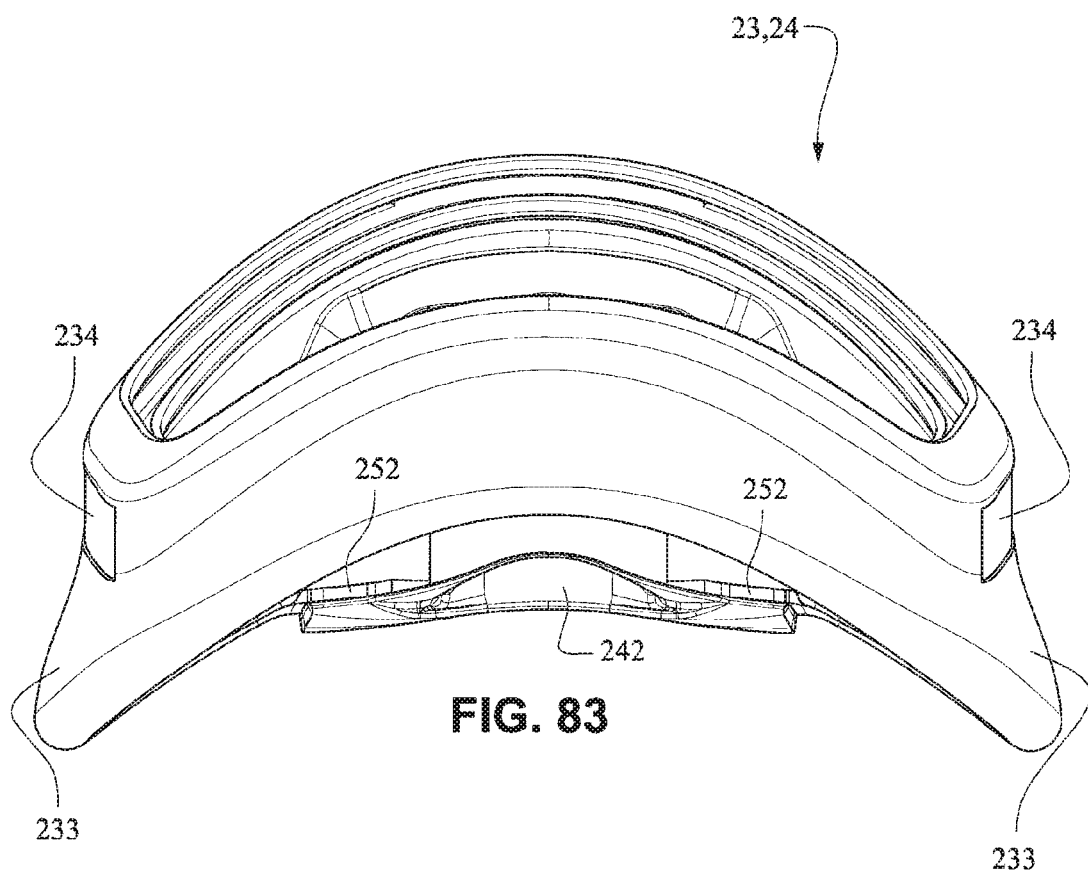

Referring to FIGS. 77-83, in the assembled condition, the flaps 252 of the nares support portions 235 of the mouth seal or cushion 23 attach to the respective sides of the nasal seal or cushion 24. A central portion 242 of the nasal seal or cushion 24 is left unsupported by the nares support portions 235 to allow the flexibility of the central portion 242 accommodate varying shaped lip regions of patients. As shown in FIG. 78, the upper portion 237 of the mouth seal or cushion 23 is generally in line with or vertically aligned to the nasal seal or cushion 24 so the patient's nose is likely to rest inside the cushion. The nasal seal or cushion 24 is positioned to reside within the mouth cushion 23 which reduces visual bulk and streamlines the outer edge of the mask. As shown in FIG. 79, the slots 234 for the connectors 22 of the front plate 21 are positioned below the nasal seal 24 so as to direct the headgear straps 34, 35 along or below the patient's cheeks. It should be appreciated that the patient interface system may comprise a number of nasal seals or cushions 24. For example, a single mouth cushion 23 may be provided to fit a large percentage of the patient population and two or more nasal seals or cushions 24 may be provided to provide a more custom fit for individual patients nose sizes.

Figure 96:
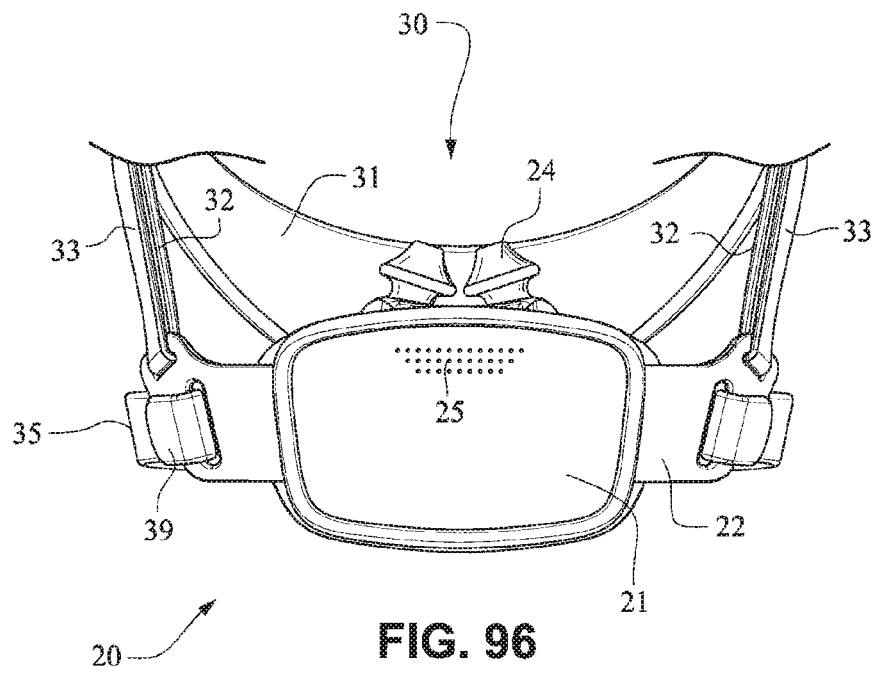
FIG. 96 is a front view of a patient interface system according to another example embodiment of the present technology.

Referring to FIG. 96, it should be appreciated that a nasal seal or cushion comprising nasal pillows may be provided to the mouth cushion. It should be appreciated that a plurality of nasal seals or cushions having different size nasal pillows may be provided to the patient interface system.

Figure 97:
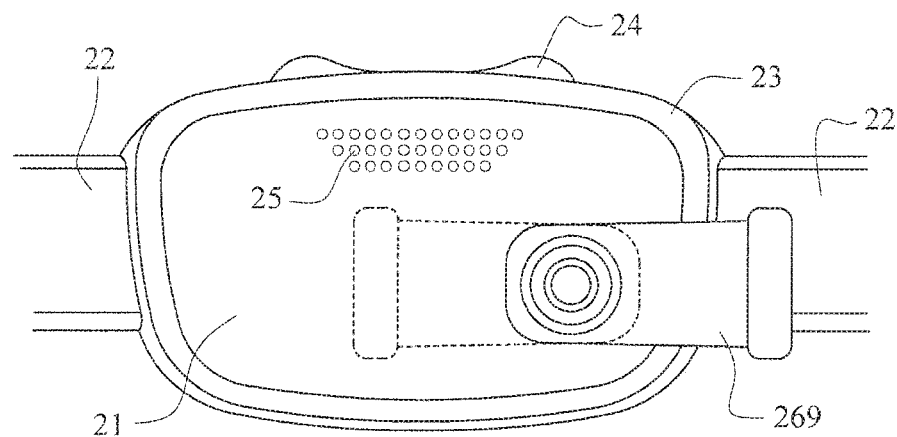
FIG. 97 is a front view of a patient interface system according to another example embodiment of the present technology.

Referring to FIG. 97, the tube connector may comprise an elbow 269 that is rotatably connected to the front plate 21. Elbow 269 may be lockable in the two positions as show, i.e. left and right horizontal orientations.

Figure 98:
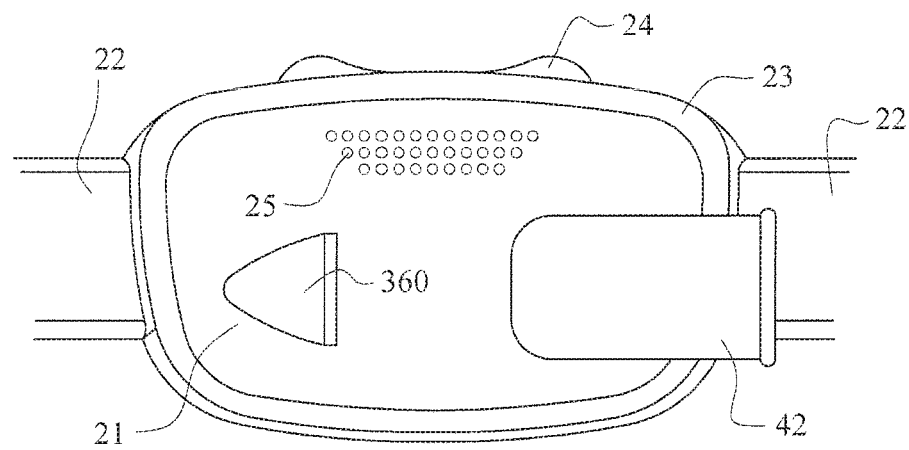
FIG. 98 is a front view of a patient interface system according to another example embodiment of the present technology.

Referring to FIG. 98, the patient interface structure 20 may include an anti-asphyxia valve 360 provided in the front plate 21.

Figure 99:
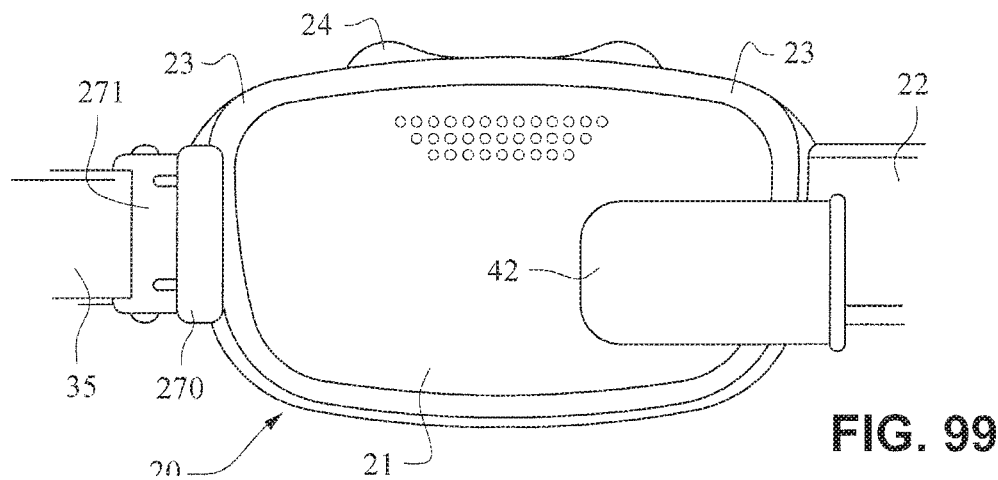
FIG. 99 is a front view of a patient interface system according to another example embodiment of the present technology.
Figure 100:
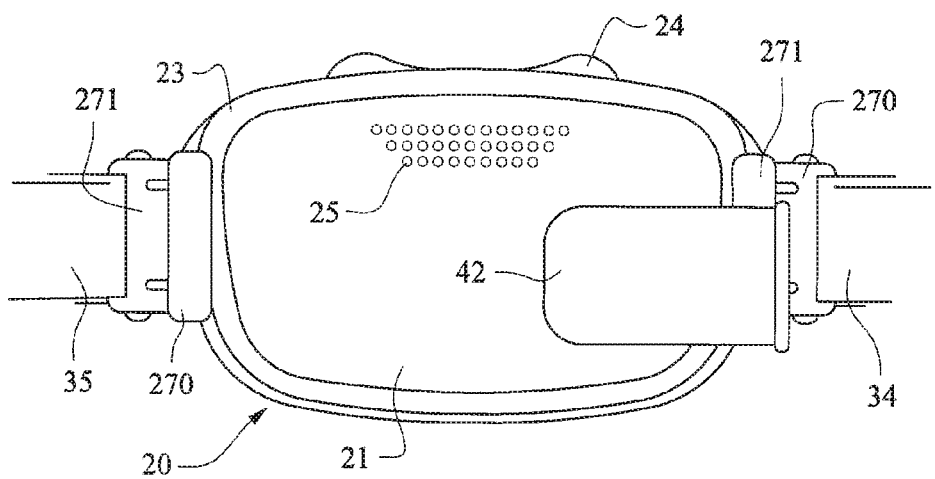
FIG. 100 is a front view of a patient interface system according to another example embodiment of the present technology.

Referring to FIG. 99, the front plate 21 may include a receptacle 270 configured to receive a clip 271 provided on a strap 35 of the patient interface positioning system. As shown in FIG. 100, the front plate 21 may include receptacles 270 on opposing sides, each configured to receive a clip 271 attached to a strap 34, 35. The clips and receptacles may also be magnetic.

Cushion/Seal—Cushion Clip

Figure 128:
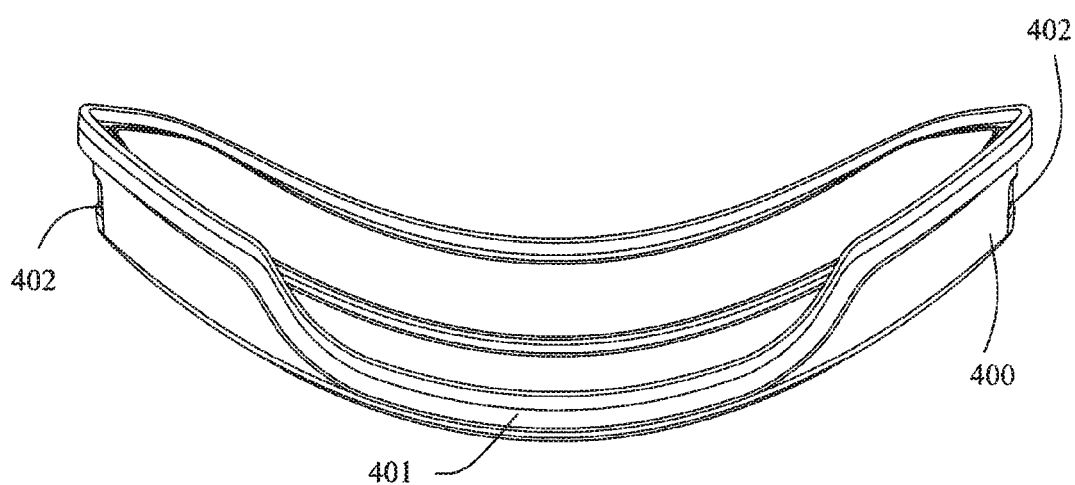
FIG. 128 is a top view of the cushion clip.

Referring to FIGS. 115-128, 135 and 136, a seal or cushion assembly includes a mouth seal or cushion 23 and a nasal seal or cushion 24. The cushion assembly may be similar to that disclosed with respect to FIGS. 63-83 except as otherwise described herein. The cushion assembly may comprise a cushion clip 400 attached to the cushion assembly and configured to attach the cushion assembly to a fascia or front plate or lens as described herein. The cushion clip 400 may comprise detents 402 on opposite sides to retain the cushion assembly on the fascia. As shown in, for example, FIG. 128, the cushion clip 400 may have a curved portion 401 that curves away from the cushion assembly to allow the nasal seal 24 to have a greater depth than a top surface of the mouth cushion 23. This may allow the nasal seal 24 to accommodate long noses. As shown in FIG. 116, the central portion 242 of the mouth cushion 23 may dip or curve downwards towards the patient's lip to avoid contacting the patient's septum. As shown on FIG. 115, nasal seal 24 may comprise raised upper corner regions, these raised upper corner regions adapted to engage a patient's nostrils or nasal flares, thereby reducing the force on the patient's nose tip.

Figure 115:
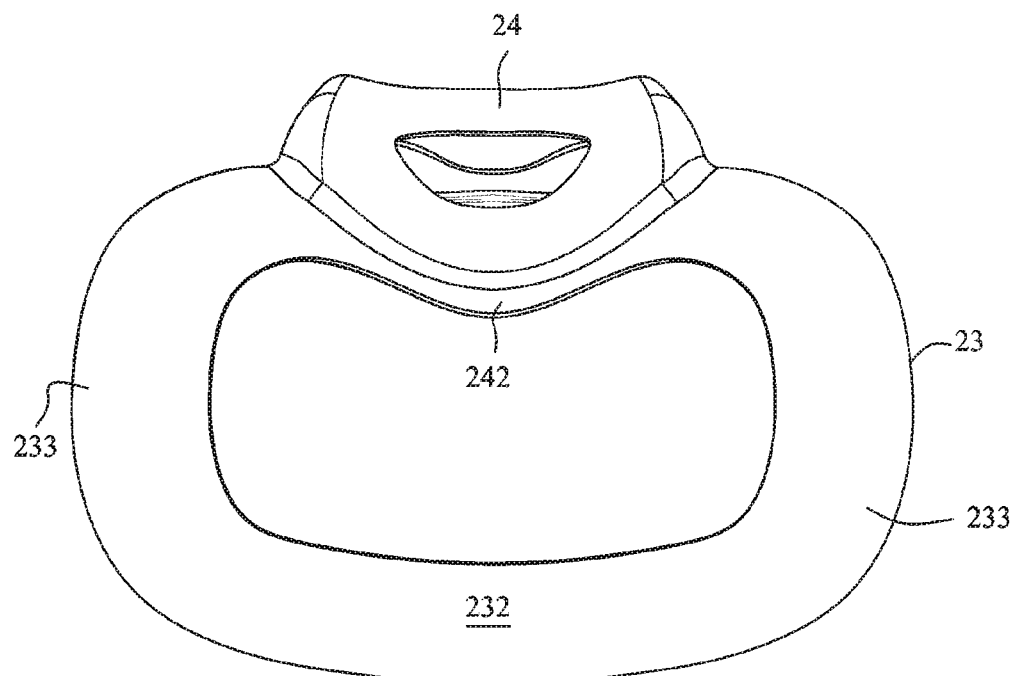
FIG. 115 is a rear view of a cushion assembly, including a mouth seal or cushion and a nasal seal or cushion.
Figure 116:
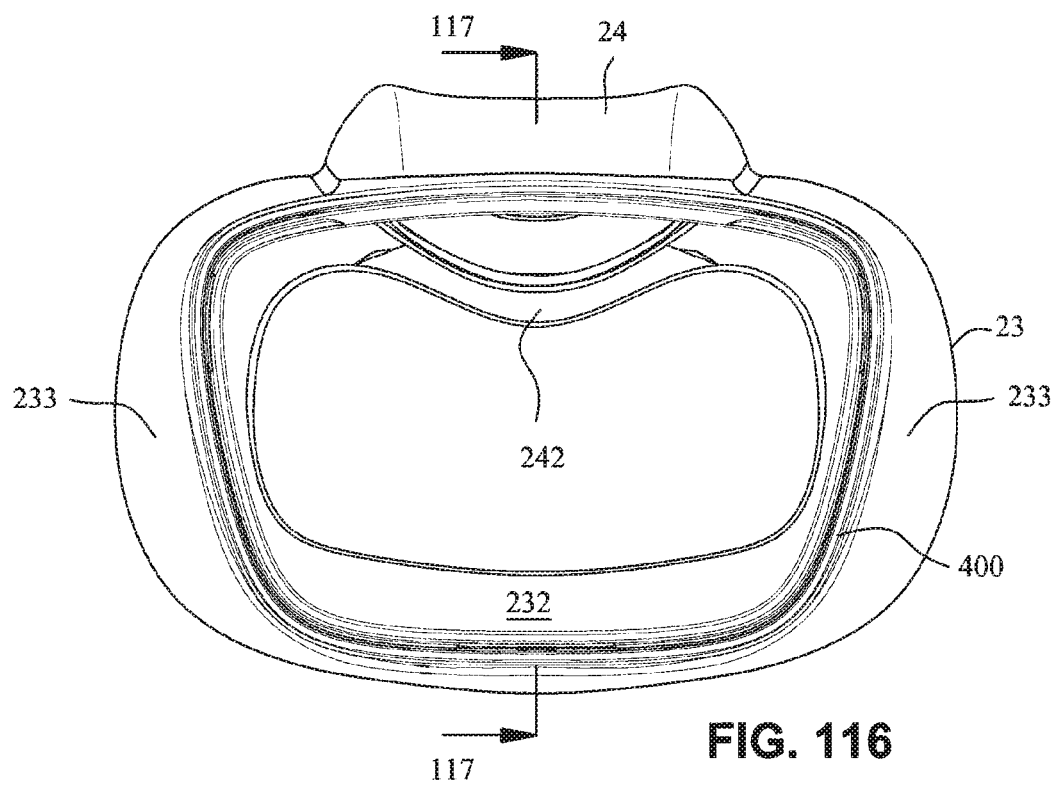
FIG. 116 is a front view of the cushion assembly of FIG. 115 including a cushion clip.

Referring to FIG. 115, the height of the aperture in the mouth cushion may be about 25-35 mm. Preferably, the height of the aperture on the mouth cushion may be about 25-30 mm. The height is measured from the lowest portion of the opening at the chin region to the dip or curve of the opening at the top lip region. The height of the aperture may increase towards the cheek or left and ride side regions.

Figure 122:
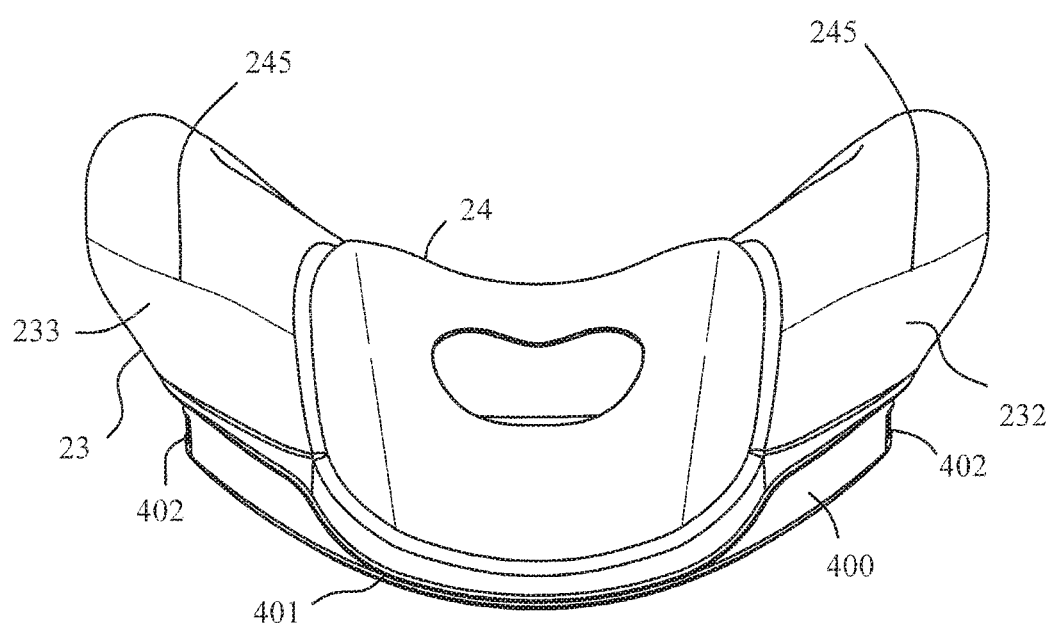
FIG. 122 is a top view of the cushion assembly and cushion clip.
Figure 123:
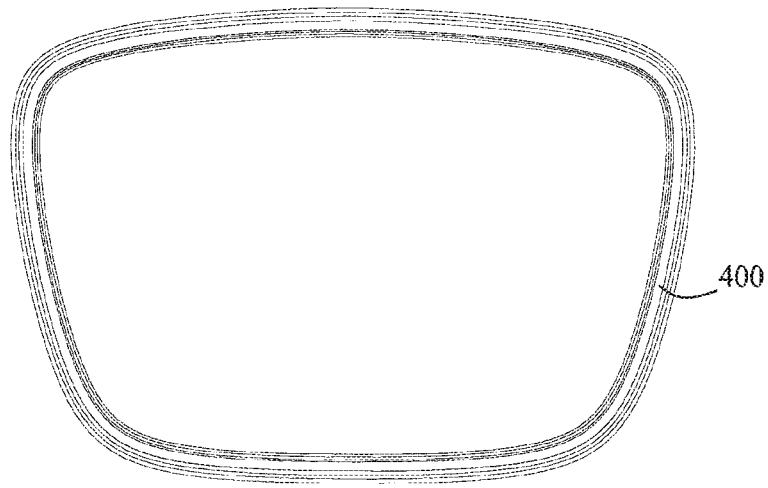
FIG. 123 is a rear view of the cushion clip.

Referring to FIG. 122, the height of the aperture in the nose cushion may be about 5-15 mm. Preferably, the height of the aperture in the nose cushion may be about 7-12 mm. The height of the aperture in the nose cushion may be less in the central region of the aperture compared to the height of the aperture at the side regions. That is, the nose cushion aperture may have a dip or curved portion at the central region. Such an arrangement may aid in alignment of the cushion, avoid placing excess pressure on the patient's septum and/or ensure that the lower portion of the nasal cushion is not under tension and therefore may not exert pressure on the patient's top lip.

Referring to FIG. 115, the width of the aperture in the mouth cushion may be about 60-70 mm. Preferably the width of the aperture in the mouth cushion may be about 63-68 mm. Such a width may accommodate varying mouth widths of patient's.

Referring to FIG. 122, the total width of the nose and mouth cushion may be about 90-105 mm. Preferably, the total width of the nose and mouth cushion may be about 95-100 mm. Such a width may accommodate varying patient anthropometrics.

Referring to FIG. 115, the total height of the nose and mouth cushion may be about 60-75 mm. Preferably, the total height of the nose and mouth cushion may be about 65-75 mm. Such a height may accommodate varying patient anthropometrics.

The patient contacting portion of the nose and/or mouth cushions may be about 0.3-1.5 mm thick. Preferably, patient contacting portion of the nose and/or mouth cushions may be about 0.3-0.7 mm thick. Such a thickness may ensure conformability of the cushion and comfort for the patient.

Referring to FIG. 116, the height of the clip may be about 40-55 mm. Preferably, the height of the clip may be about 45-55 mm. The height of the clip may be greater than the height of the mouth cushion aperture. Such an arrangement may be simpler to engage the clip with a fascia (for example) and may increase the structural integrity of the cushion.

Referring to FIG. 116, the width of the clip may be about 70-85 mm. Preferably, the width of the clip may be about 75-80 mm. The width of the clip may be greater than the width of the mouth cushion aperture. Such an arrangement may be simpler to engage the clip with a fascia (for example) and may increase the structural integrity of the cushion.

Figure 124:
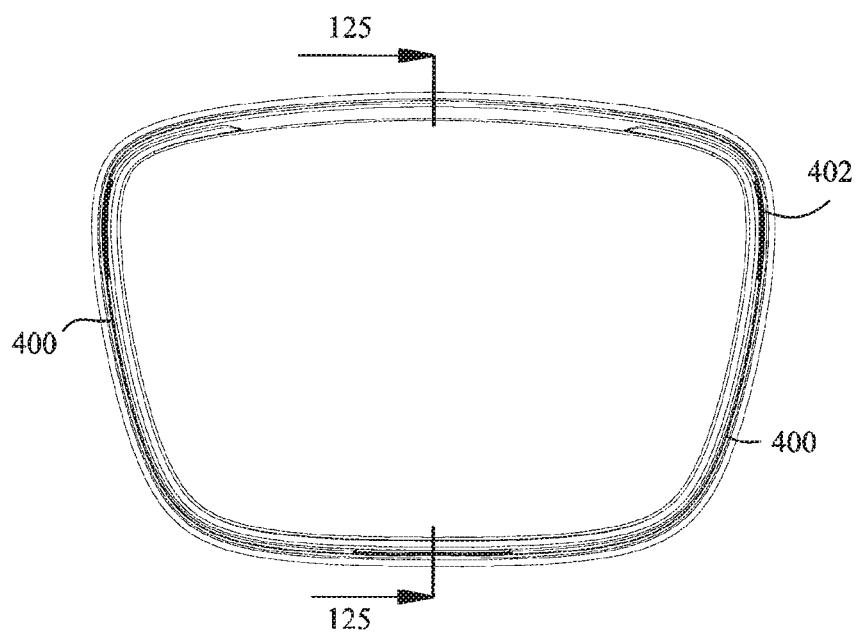
FIG. 124 is a front view of the cushion clip.

As shown in, for example, FIG. 124, the cushion clip may be generally trapezoidal, with the top portion being wider than the lower portion. Such an arrangement may mean that the overall shape of the mask is shaped to match the general shape of a humans face i.e. taper from a greater width at the top lip region to a lower width at the chin region. The top portion may be, for example, about 75-85 mm wide. The lower portion may be, for example, about 65-75 mm wide.

Figure 117:
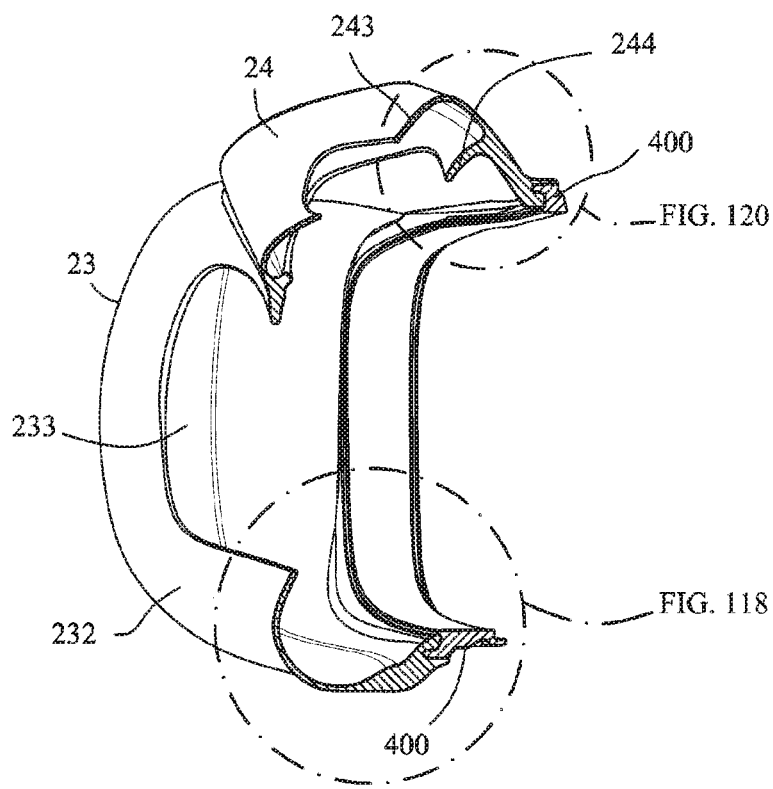
FIG. 117 is a cross section view of the cushion assembly and cushion clip along line 117-117 in FIG. 116.
Figure 118:
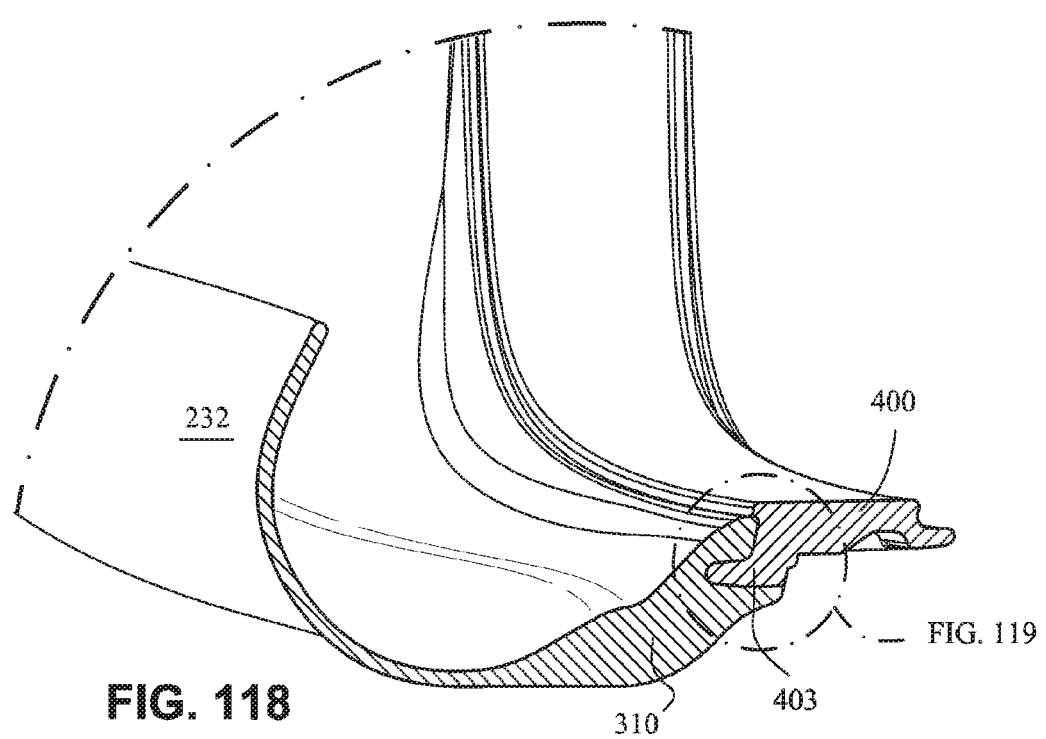
FIG. 118 is a detailed view of the connection of the cushion assembly and the cushion clip at a lower portion of the cushion assembly.
Figure 119:
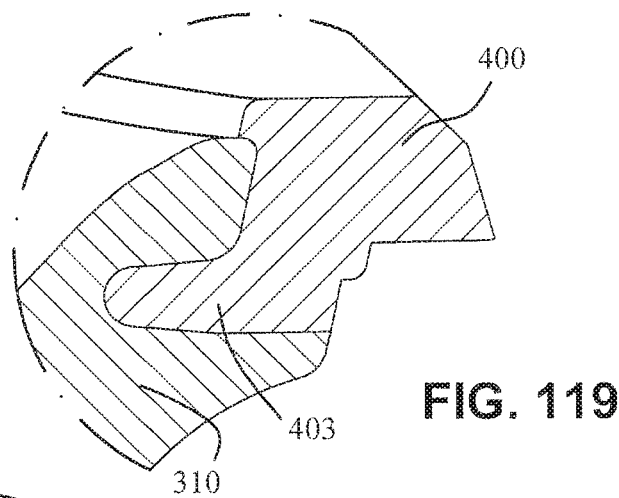
FIG. 119 is a detailed view of FIG. 118.
Figure 120:
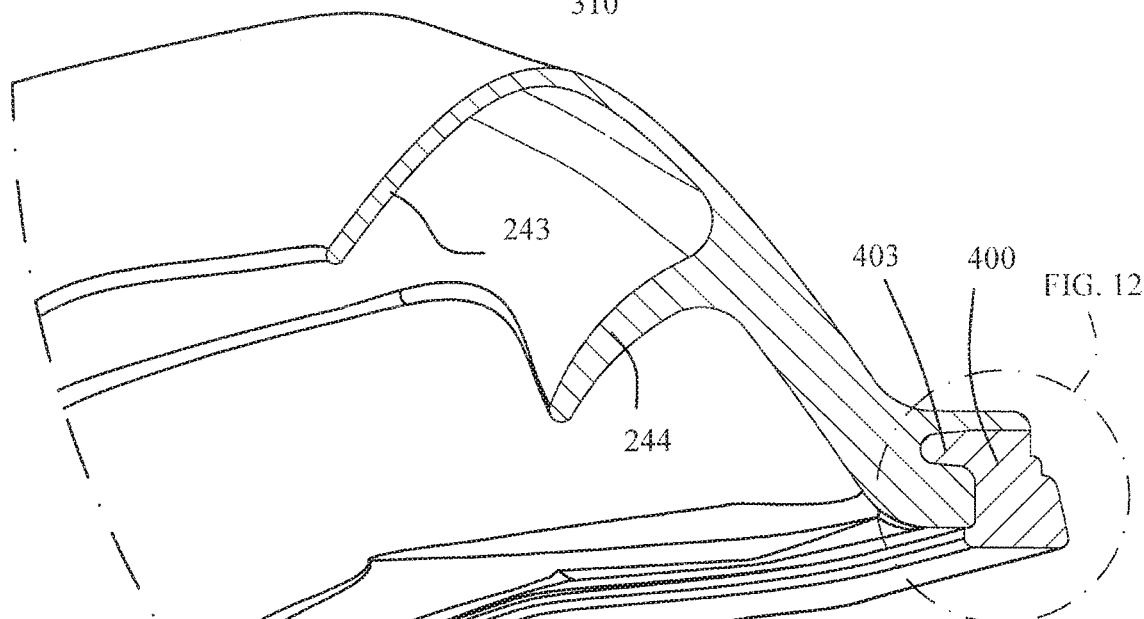
FIG. 120 is a detailed view of the connection of the cushion assembly and the cushion clip at an upper portion of the cushion assembly.
Figure 121:
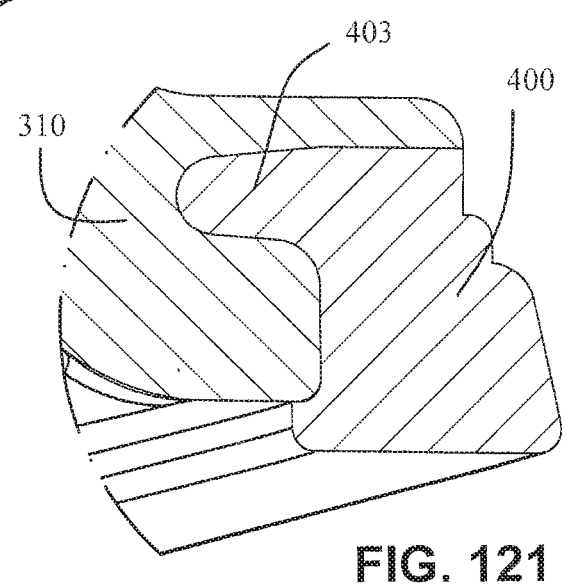
FIG. 121 is a detailed view of FIG. 120.

As shown in, for example, FIGS. 117-121, the cushion may be integrally formed in one piece. The mouth cushion 23 may have a single wall seal 232 and the nasal cushion 24 may have a dual wall construction comprising a sealing wall 243 and a supporting wall 244. It should be appreciated that the mouth cushion 23 and the nasal cushion 24 may each include a single wall, or each may include multiple walls. The sealing walls 232 and 243 of the mouth cushion 23 and the nasal cushion 24 may curve inwards toward a breathing chamber or cavity formed by the cushions. As shown in FIG. 117, only a portion of the supporting wall 244 of the nasal cushion 24 may be present, for example, at the tip of the nose region and not at the top of the lip region. Referring to FIG. 122, a parting line 245 of the mould used to form the cushion assembly may be provided so as to be above the patient contacting areas of the cushion assembly.

Figure 136:
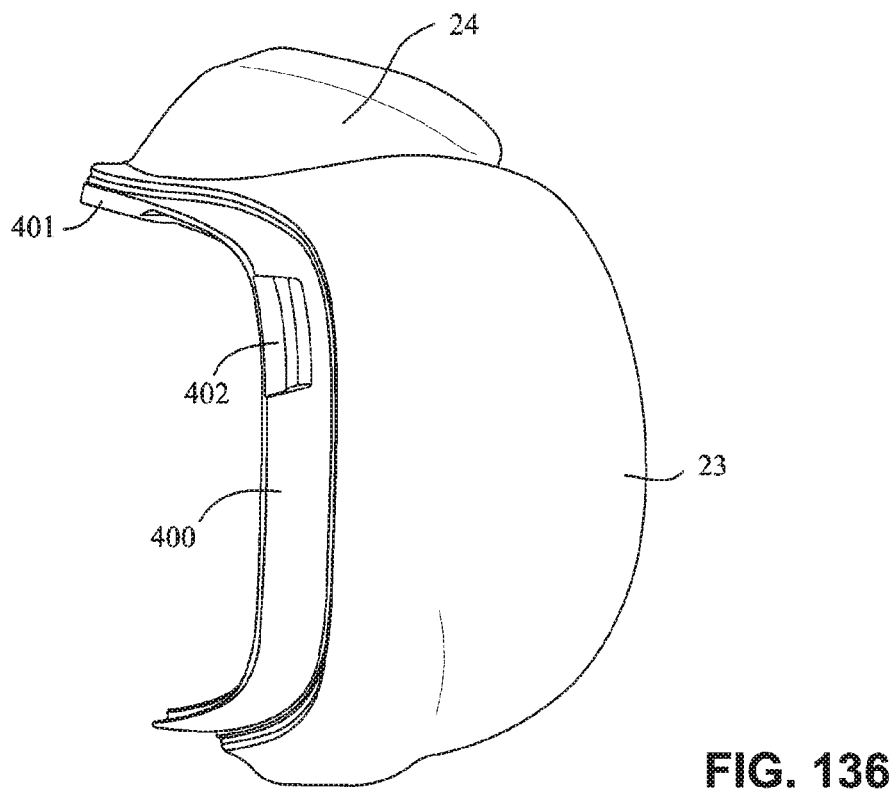
FIG. 136 is a left side view of the cushion assembly and cushion clip of FIG. 135.

Referring to FIG. 136, the cushion assembly and the cushion clip 400 may be formed integrally in one piece. The cushion assembly may be insert, over, or co-moulded into the cushion 23 as one part. Alternatively, the cushion assembly and the cushion clip 400 may be chemically or mechanically bonded together. The cushion assembly and cushion clip 400 may also be repeatably attachable and detachable from one another. For example, the cushion clip 400 may include a flange configured to be received in a channel in the cushion assembly.

As shown in FIGS. 117-121, 126 and 127, the cushion clip 400 may include a flange or rib 403 to increase the surface area of the cushion clip 400 to enhance the bond between the cushion clip 400 and the cushion assembly. The cushion assembly, for example the mouth cushion 23, may include a thickened region 310 to provide support for the sealing wall 232 and to improve the bond to the cushion clip 400. Rib 403 may have a varying height around the perimeter of the cushion clip 400. This varying height may support the cushion more in some regions (i.e. the regions with a greater rib height such as sensitive regions of the face such as the top lip) compared to support in other regions (i.e. regions with a lower rib height such as less sensitive regions of the face such as the cheeks).

Cushion Assembly—Continuous Sealing Surface

Figure 129:
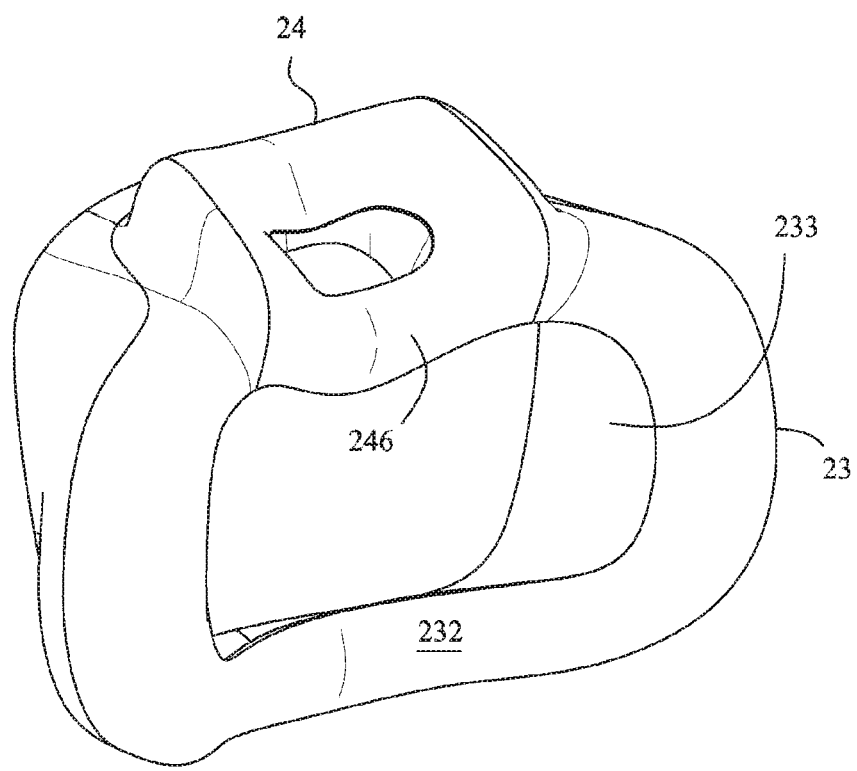
FIG. 129 is a rear isometric view of a cushion assembly according to an embodiment of the present technology.
Figure 130:
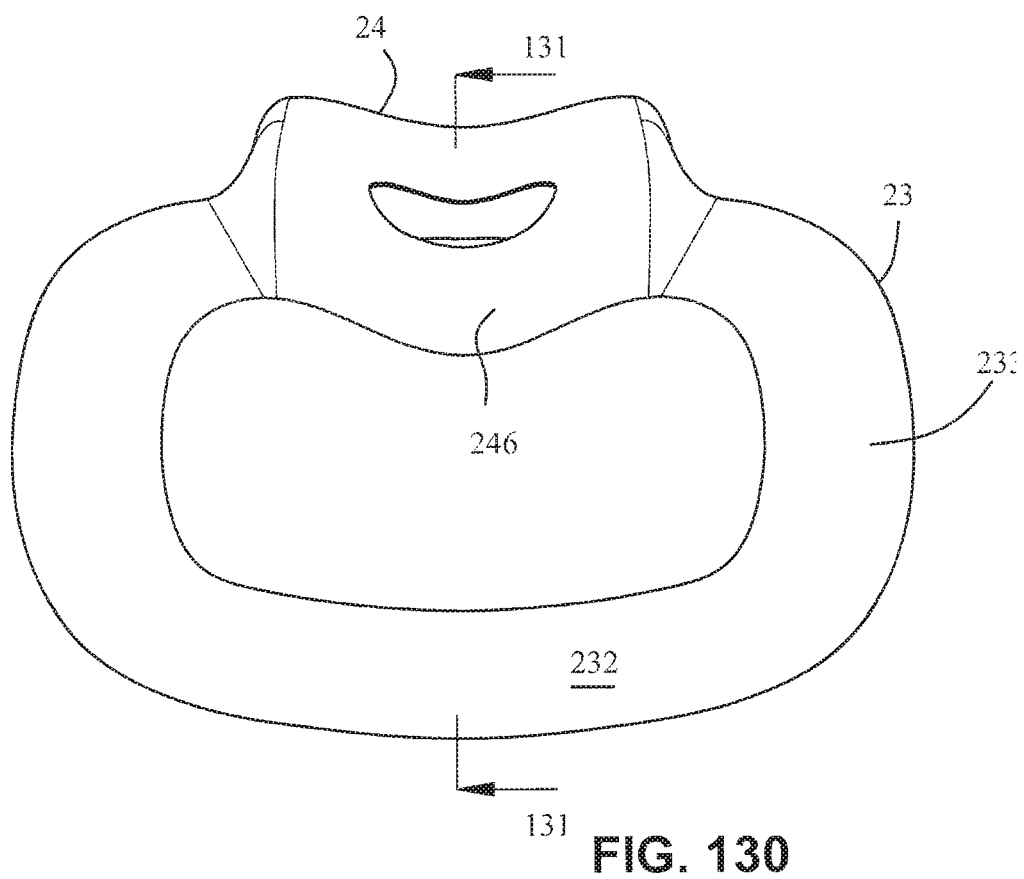
FIG. 130 is a rear view of the cushion assembly of FIG. 129.
Figure 131:
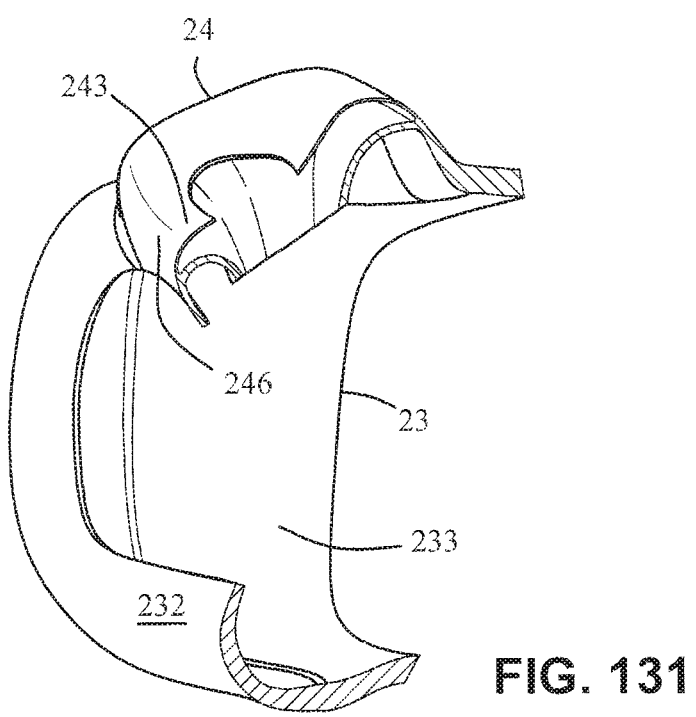
FIG. 131 is a cross section view of the cushion assembly along line 131-131 in FIG. 130.

Referring to FIGS. 129-131, a cushion assembly including a mouth cushion 23 and a nasal cushion 24 may comprise a continuous sealing surface 246. As show in FIG. 131, the sealing surface 246 is continuous with the mouth cushion sealing wall 232 and the nasal cushion sealing wall 243. The curvature of the sealing surface 246 may be constant or approximately constant. Such an arrangement may be comfortable for the patient as there are no ridges or undulations that may mark or otherwise irritate the patient's skin. In this arrangement, the definition between the nose and mouth seal portions is not distinct, such that the seal is continuous.

Cushion Assembly—Separate Sealing Surfaces

Figure 132:
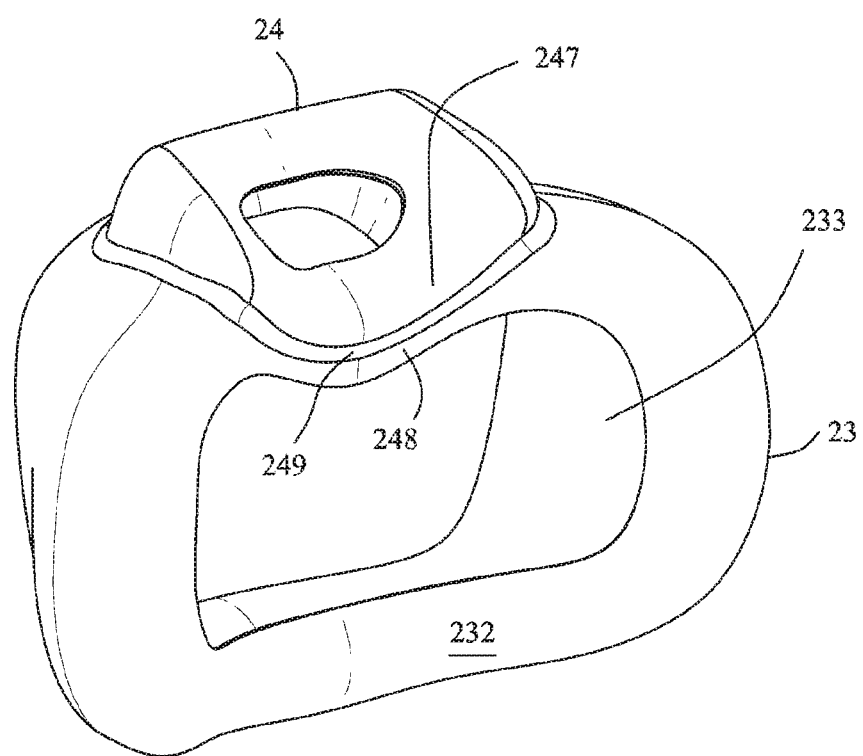
FIG. 132 is a rear isometric view of a cushion according to an embodiment of the present technology.
Figure 133:
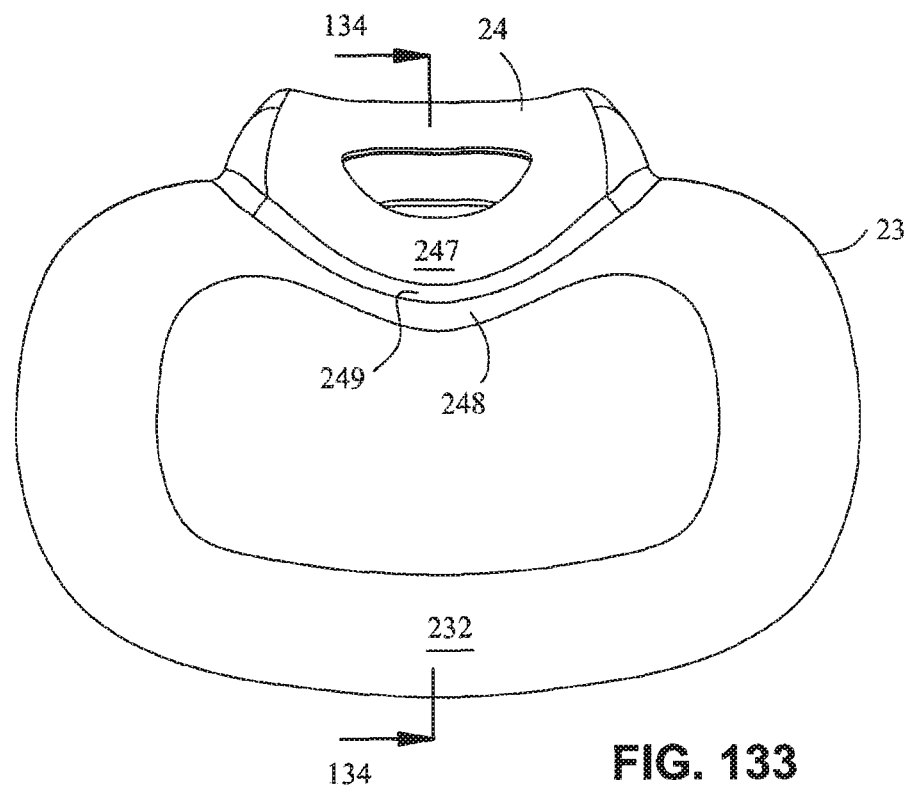
FIG. 133 is a rear view of the cushion assembly of FIG. 132.
Figure 134:
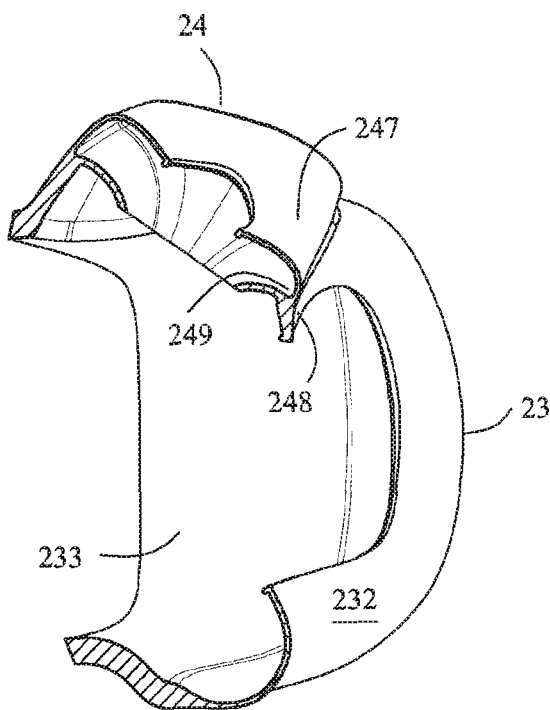
FIG. 134 is a cross section view of the cushion assembly along line 134-134 in FIG. 133.
Figure 135:
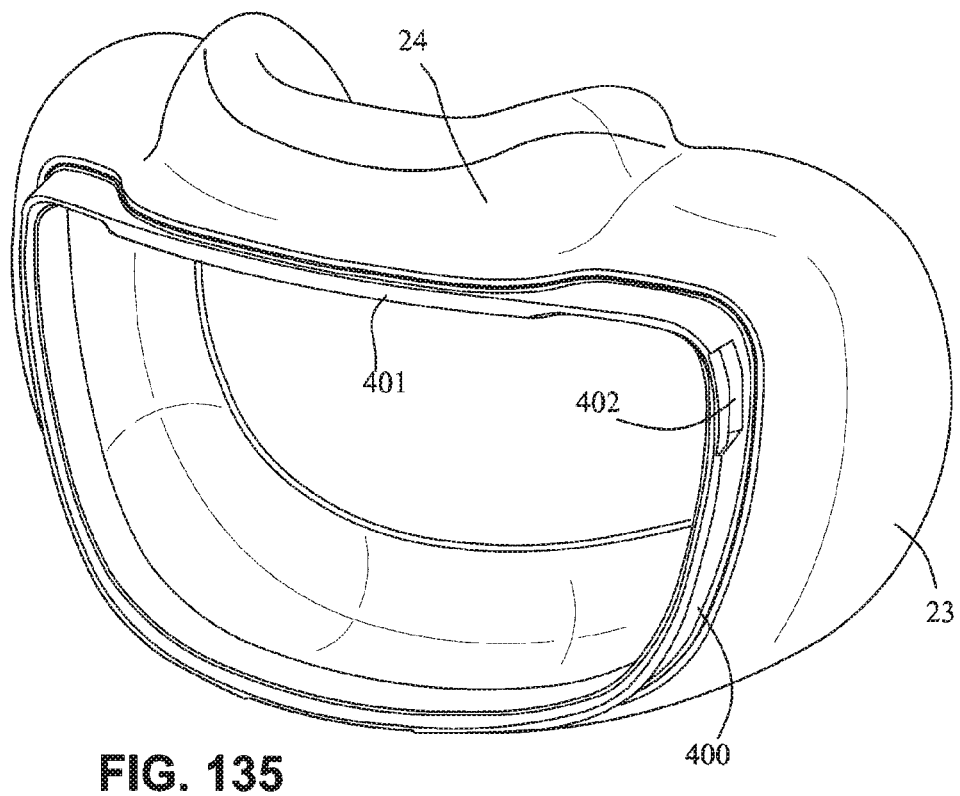
FIG. 135 is a front isometric view of the cushion assembly and cushion clip of FIG. 125.

Referring to FIGS. 132-134, a cushion assembly including a mouth cushion 23 and a nasal cushion 24 includes separate sealing surfaces 247, 248. A channel 249 is provided to separate the nasal sealing surface 247 from the mouth sealing surface 248. Such an arrangement may be preferable as the nose and mouth seal portions are visually distinct which may assist the patient with aligning the device.

Patient Interface Systems—Tube Connection—Behind Connector

Referring to FIGS. 14-25, a patient interface system 10 according to an example embodiment of the present technology includes a delivery hose, or tube, or conduit 11 that is connected to the front plate 21 by a connector 12, e.g. a swivel connector. The tube 11 may be as disclosed in, for example, U.S. Patent Application Publication 2009/0078259 A1, the entire contents of which are incorporated herein by reference. The front plate includes an air inlet or elbow 29 that may be integrally formed with the front plate 21. It should be appreciated that the elbow 29 may be formed separately from the front plate 21 and attached or connected to the front plate 21 or the cushion 23, for example by adhesive or mechanical fasteners. The elbow 29 is positioned behind or adjacent to the connector 22 of the front plate 21 on the left side, although it should be appreciated that the elbow 29 may be provided on the right side of the front plate 21. The shape of the elbow 29 is curved to avoid obscuring the headgear connector 22. However other configurations would be possible if the headgear connector 22 was located in an alternative position.

The tube connection portion of the elbow 29 is adapted to receive the tube 11 in a longitudinal (e.g. vertical) direction, however other orientations are possible. The elbow 29 is not visible from the front as it is hidden behind the headgear connector 22 of the front plate 21. This arrangement is advantageous as it is reduces the part count (i.e. no separate elbow is required) and the design may be more visually appealing. The tube 11 is connected at the side of the patient interface or mask system 10 so as to permit clear view to the patient's mouth. Because the tube connection is positioned behind the headgear connector 22 at the front plate 21, the tube 11 is less obtrusive. The eyes 4 of the patient 1 are unobstructed and in the case of the front plate 21 being in the form of a lens, for example a clear polymer (e.g. polycarbonate), the patient's mouth would also be visible.

The elbow 29 may comprise a lip or protruding edge 41, in the form of for example a chamfer, adapted to receive a slot or aperture of the cushion. The cushion 23 may comprise a slot that may be positioned to abut or align with the chamfer to aid alignment, and also ensure an air tight seal between the cushion 23 and the front plate 21 is achieved.

The patient interface structure 20 sits under the patient's nose 3 and the nasal cushion 24 seals around or in the nares. The mouth cushion 23 sits in the crease of the patient's chin 5. The crown strap 31 of the headgear 30 is positioned over the top of the patient's crown and generally in line with the patient's ears 2, although it should be appreciated that the positioning of the crown strap 31 may vary between patients.

Although the front plate 21 shown in FIGS. 20-25 includes only the bottom side strap connector slots 26, it should be appreciated that the embodiment shown in FIGS. 20-25 may also comprise top sides strap connector slots 27. It should also be appreciated that the front plate 21 may be provided with a vent, or alternatively another component, such as the tube 11, the connector 12, or the elbow 29 may have a vent.

Figure 101:
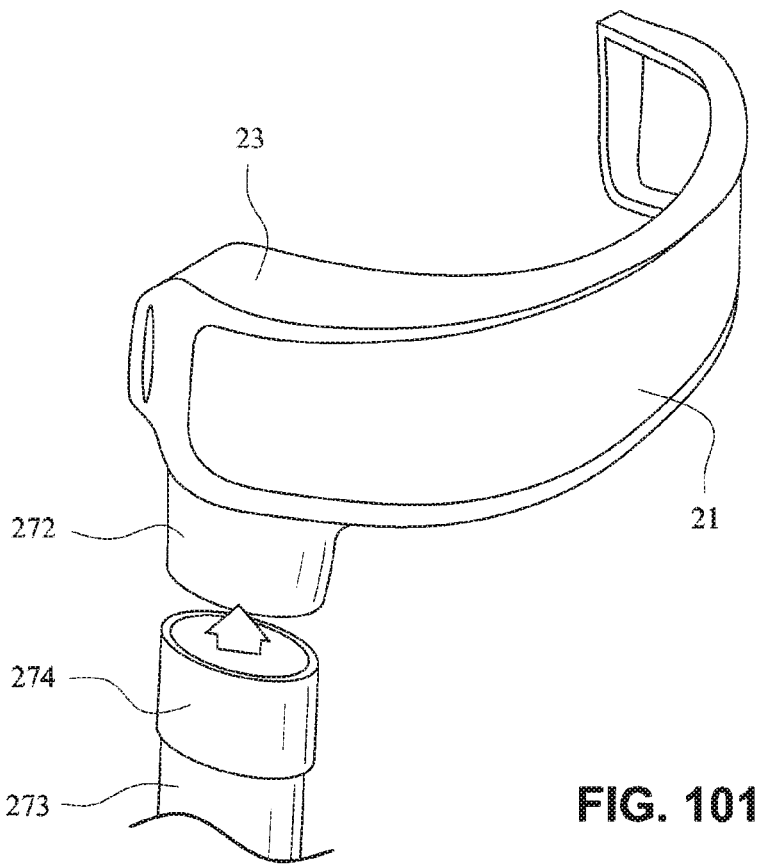
FIG. 101 is a front isometric view of a patient interface system according to another example embodiment of the present technology.

Referring to FIG. 101, a tube connector 272 may be positioned either on the front plate 21 or molded with the cushion 23. The tube connector 272 may receive an intermediate portion or portion 274 of a tube 273 that may interface with the tube connector 272 by an interference fit. The interference fit may be achieved by pinching or otherwise misshaping the intermediate portion or portion 274 of the tube 273 and placing it within the tube connector 272. When the pinch or other force is released, the intermediate portion or portion 274 of the tube 273 may resiliently flex back to its original shape and interface with an inner surface of the tube connector 272. In an alternative arrangement, tube 273 may interface with the tube connector 272 by an interference fit such as an isometric taper or a quarter turn lock.

Patient Interface Systems—Tube Connection—Front Surface

Referring to FIGS. 26-33, a patient interface system 10 according to another example embodiment of the present technology comprises a patient interface structure 20 comprising a front plate 21, a mouth cushion 23 provided to the front plate 21, and a nasal cushion 24 provided to the mouth cushion 23. The front plate 21 comprises a tube connector 42 on a front surface that is configured to receive a tube in a horizontal direction.

A tube may connect directly to the tube connector 42 or may have an intermediate structure such as an elbow or swivel between the tube and the tube connector 42, possibly shaped to avoid the tube obscuring the headgear connector 22. The tube connector 42 may have vent holes 25 molded or otherwise formed in it. The tube connector 42 may also have a lip or protruding edge 43, which may aid in sealing the tube connector 42 to the tube or intermediate structure. The tube connector 42 may have an anti-asphyxia valve (AAV) in form of a flap built in (described in more detail below) that may occlude or block some of the vent holes 25 when air is delivered from the tube and through the tube connector 42. When air pressure is not supplied, the AAV may flip away from the vent holes to permit the patient to breath in sufficient atmospheric air.

The rear face of the front plate 21 may have an aperture 44 adapted to permit the flow of air from the tube connector into the mask. The vent holes 25 may have a thicker cross section than the rest of the tube connector 42 (e.g. they are on a raised rectangular portion) to improve manufacturability. This may also be to increase the length of the vent holes 25 as longer vent holes are typically quieter than comparatively shorter vent holes. The tube connector 42 may follow the same general curvature of the front plate to reduce the visual bulk (i.e. more streamlined look) of the mask and aid in tube management.

Patient Interface Systems—Tube Connection—Elbow

Referring to FIGS. 34-55, a patient interface system 10 according to another example embodiment of the present technology may comprise an elbow 45 connected substantially perpendicular to the front plate 21. The elbow 45 may be a swivel elbow or may be a ball joint elbow. The elbow 45 may be removably attachable or molded with the front plate 21.

Patient Interface Systems—Vents

Figure 84:
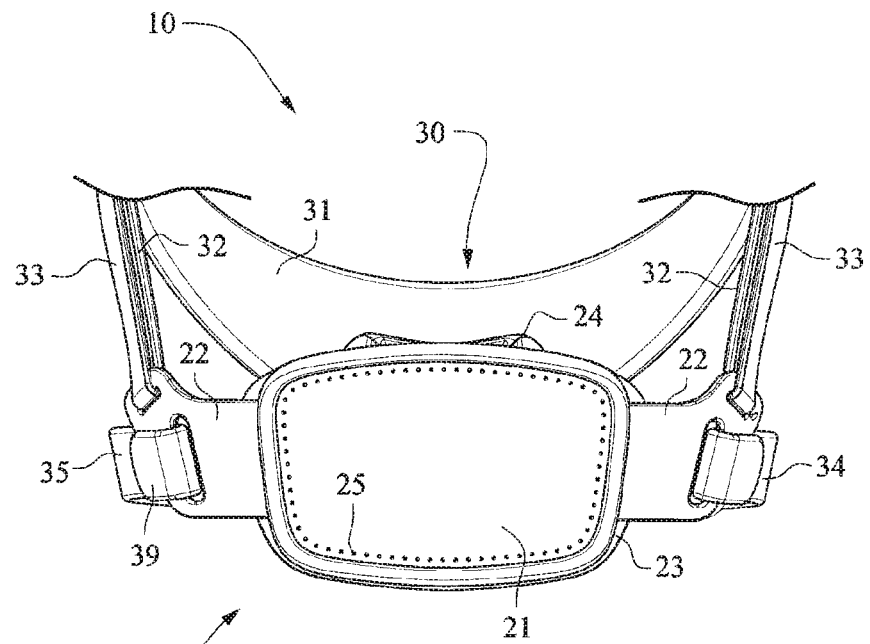
FIG. 84 is a front view of a patient interface system according to another example embodiment of the present technology.

Referring to FIG. 84, a patient interface system 10 may comprise a front plate 21 having a vent 25 comprising a plurality of vent holes provided around a perimeter of the front plate 21. The perimeter arrangement aids diffusivity of the exhaust gases and reduces the visibility of the vent 25.

Figure 85:
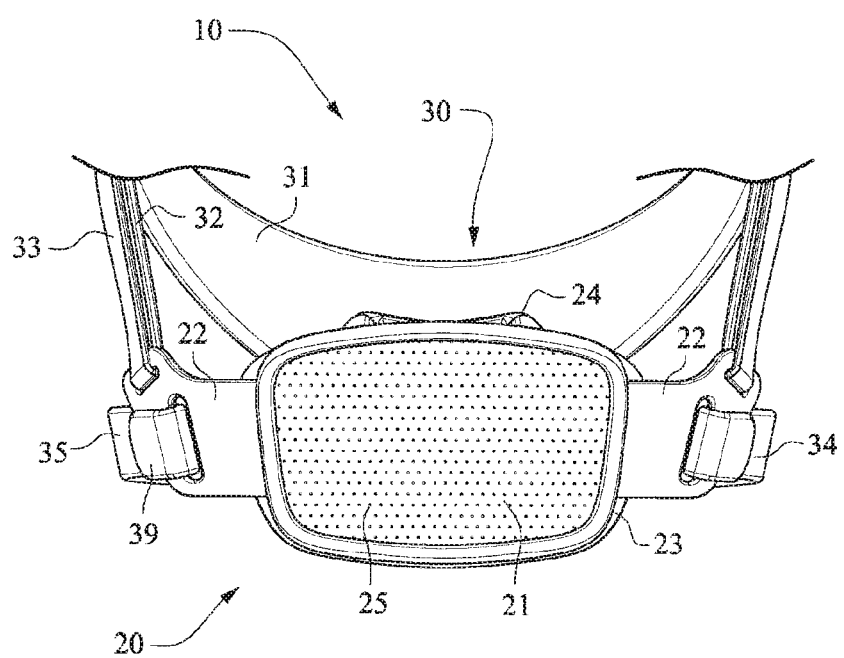
FIG. 85 is a front view of a patient interface system according to another example embodiment of the present technology.

Referring to FIG. 85, a patient interface system 10 may comprise a front plate 21 having a vent 25 that comprises micro-perforated holes over the front surface of the front plate 21.

Figure 113:
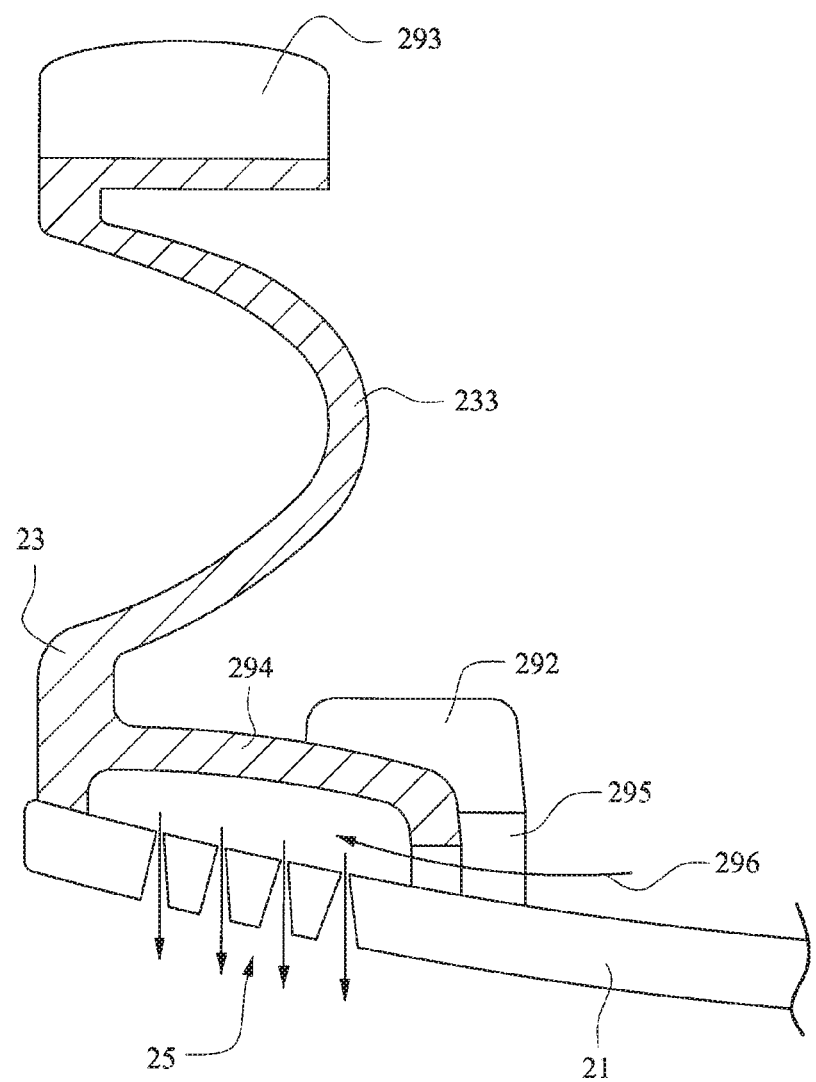
FIG. 113 is a schematic illustration of a fascia, or front plate, including a venting arrangement according to an example embodiment of the present technology.

Referring to FIG. 113, a tortuous vent path through front plate 21 may be provided for reducing noise. The tortuous path will slow down the exhaled gases 296 as it moves through the tortuous path, thereby having a lower sound power. The mouth seal may have an interface seal 293 and a flap or castellation 294 that obstructs the vent holes 25, with the exhaled gases 296 moving through the vented pathway 295 of a raised portion 292 of the front plate 21 rather than directly out of the vent holes 25 to increase the length of the path for exhaled gases to get out of the mask.

Patient Interface Systems—Tube Cuff

Figure 86:
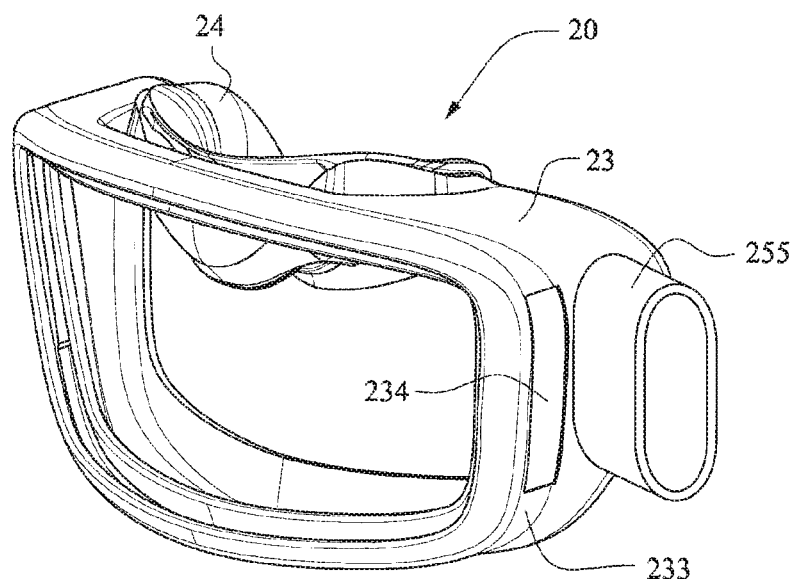
FIG. 86 is a front isometric view of a patient interface system according to another example embodiment of the present technology.

Referring to FIG. 86, a patient interface system 10 may include a mouth cushion 23 having a tube cuff 255 attached to, for example, the side wall 233 of the cushion 23. The tube cuff 255 may be moulded onto the side wall 233 and may have a hardness greater than that of the side wall 233.

Figure 95:
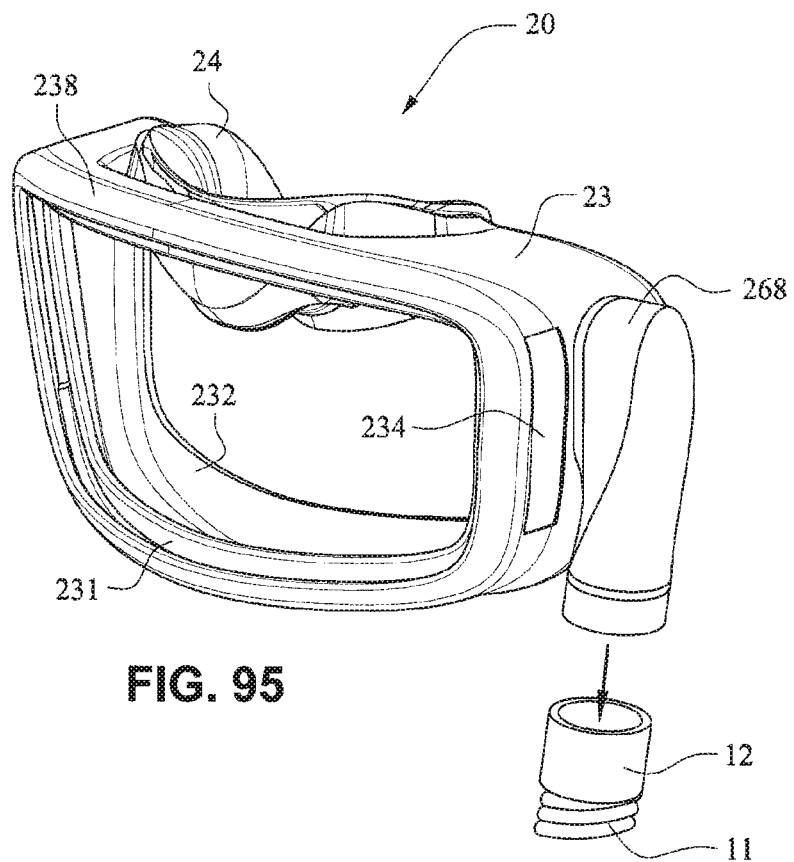
FIG. 95 is a front isometric view of a patient interface system according to another example embodiment of the present technology.

Referring to FIG. 95, a tube cuff 268 may be moulded onto the cushion 23 that is configured to be connected to a connector 12, e.g. a swivel connector, that is configured to be connected to a tube 11, for example a tube as disclosed in U.S. Patent Application Publication 2009/0078259 A1, the entire contents of which are incorporated herein by reference. It should be appreciated that the tube cuff 268 may be connected to the cushion by, for example, adhesive or mechanical connectors.

Figure 103:
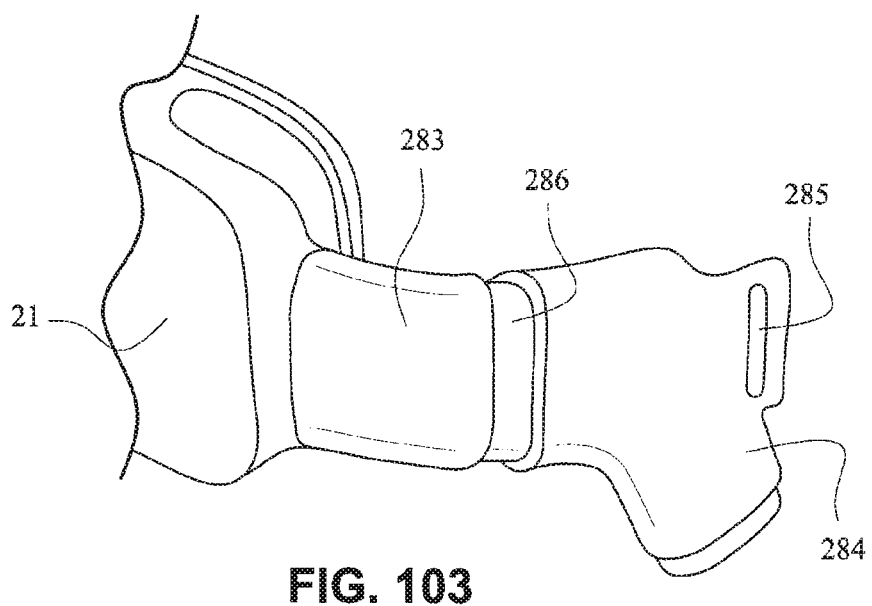
FIG. 103 is a front isometric view of a patient interface system according to another example embodiment of the present technology.

Referring to FIG. 103, a gap 286 between a tube connector 283 and a cuff 284 (having less width when compared to the tube connector for example) may be adapted to receive a headgear strap that extends in a substantially vertical direction. The cuff 284 may include a link or slot 285 to receive a headgear strap that extends in a substantially horizontal direction. The cuff 284 may be soft or relatively flexible. The cuff 284 may be glued on or otherwise attached to the tube connector 283. The cuff 284 may be formed with the tube connector 283.

Patient Interface Systems—Anti-Asphyxia Valves (AAV)

Figure 87:
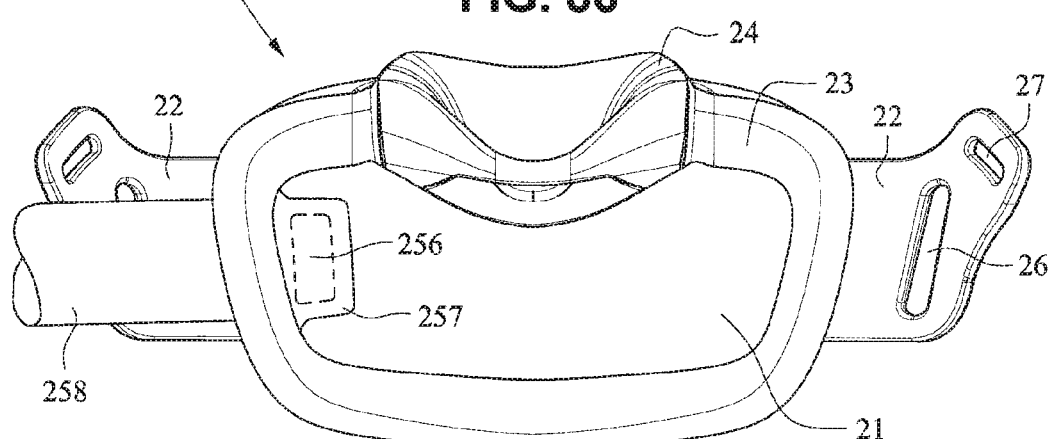
FIG. 87 is a rear view of a patient interface system according to another example embodiment of the present technology.
Figure 88:
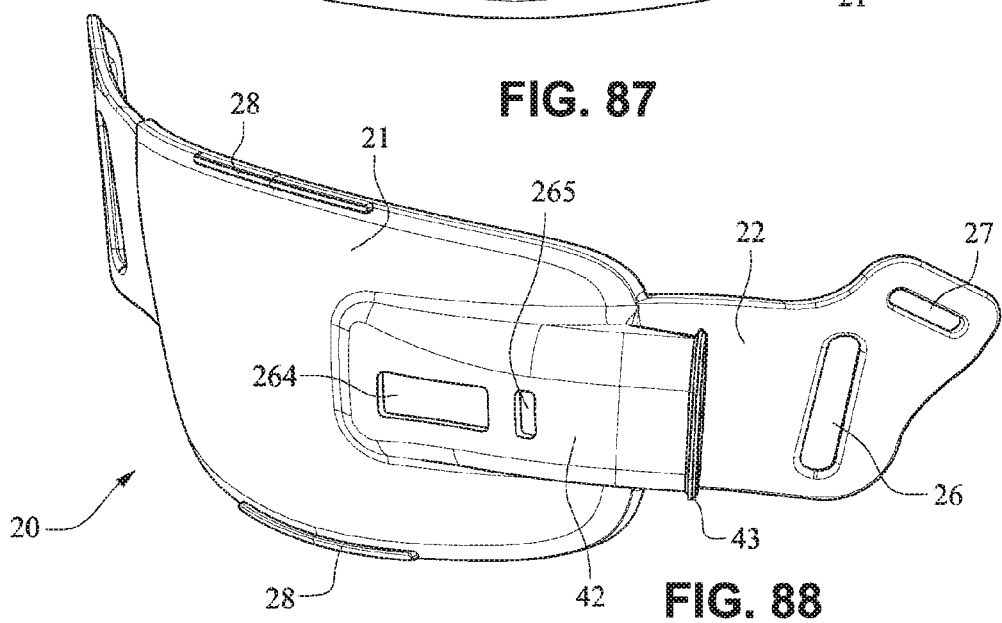
FIGS. 88-94 are views of a patient interface system according to another example embodiment of the present technology.
Figure 89:
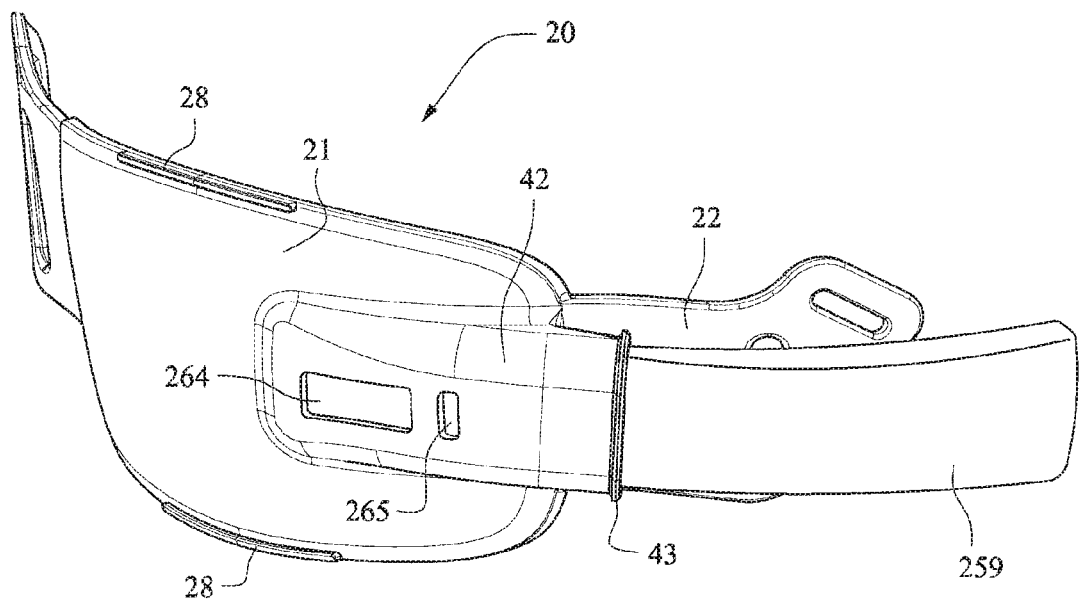
Figure 90:
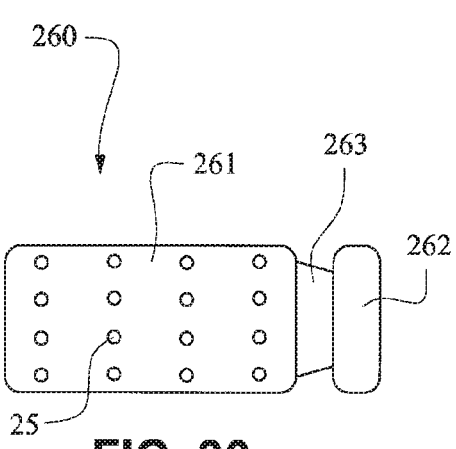
Figure 91:
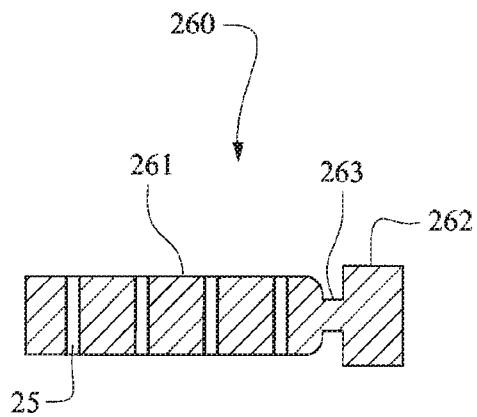

Referring to FIG. 87, a patient interface system 10 may comprise a front plate or lens 21 having a hole 256. An anti-asphyxia valve in the form of a flap 257 formed in the mouth seal or cushion 23 is forced against the front plate 21 and covers the hole 256 when a flow of pressurized gas is delivered through a tube or hose or conduit 258. In the absence of the flow, the flap 257 is released from contact with the front plate 21 and uncovers the hole 256, allowing the patient to breathe ambient air through the hole 256 in the front plate 21.

Figure 92:
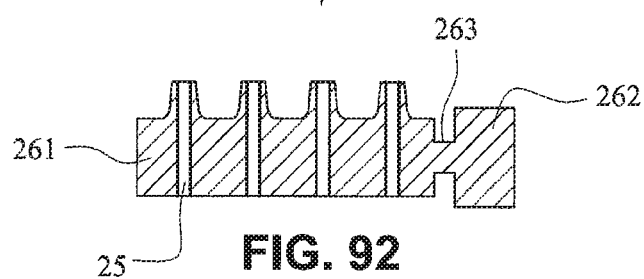
Figure 93:
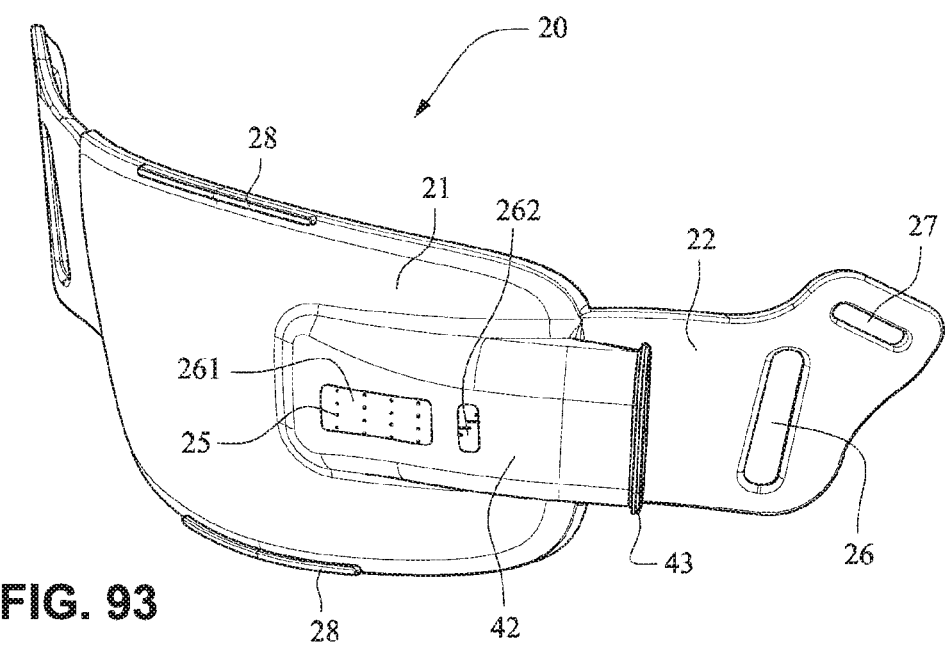
Figure 94:
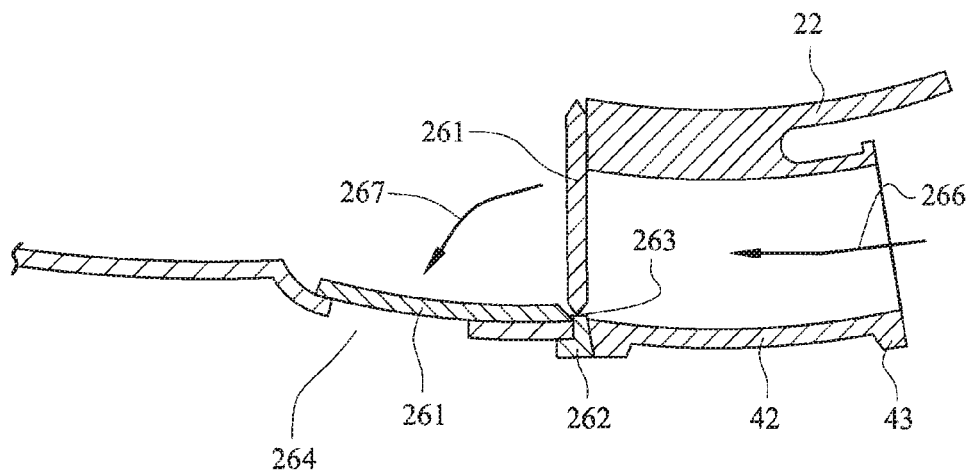

Referring to FIGS. 88-95, a patient interface system 10 may comprise a front plate 21 having a tube connector 42 configured for connection with a tube or hose or conduit 259. The tube connector 42 comprises an aperture or window 264 that may be closed by an anti-asphyxia valve 260. The anti-asphyxia valve 260 comprises a flap 261 that is configured to open and close the aperture 264. The flap 261 may comprise a vent 25 for venting exhalation gases when the flap 261 closes the aperture 264. The anti-asphyxia valve further includes a tab 262 that secures the anti-asphyxia valve 260 in the tube connector 42 through a slot 265 in the tube connector 42. The flap 261 is pivotably connected to the tab 262 by a hinge 263, e.g. a living hinge. As shown in FIG. 94, in the absence of a flow of gas in the tube connector 42, the flap 261 extends across the tube connector, and the patient may breathe through the aperture 264. When gas flow 266 is delivered to the tube connector 42, the pressure of the gas flow 266 pivots the flap 261 in the direction shown by arrow 267 to close the aperture 264. Exhalation gases may be vented through the vent 25. Referring to FIG. 92, the flap 261 may include elongated vent holes 25 to reduce venting noise and increase diffusivity of the vent flow.

Figure 106:
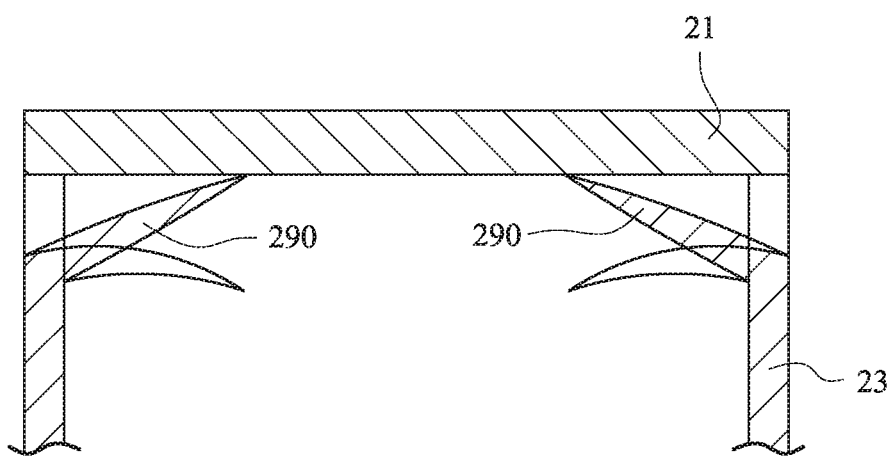
FIG. 106 is a schematic illustration of a fascia, or front plate, and a seal, or cushion, including an anti-asphyxia valve according to an example embodiment of the present technology.
Figure 107:
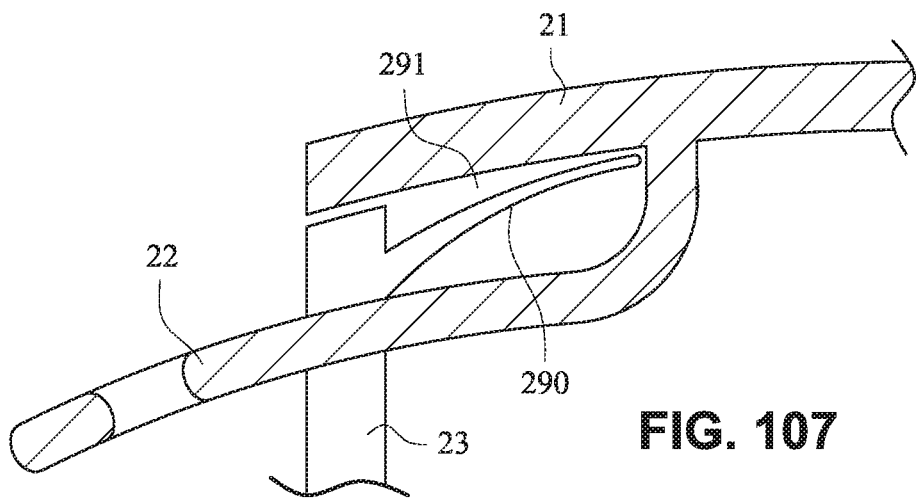
FIG. 107 is a schematic illustration of a fascia, or front plate, and a seal, or cushion, including an anti-asphyxia valve according to another example embodiment of the present technology.

Referring to FIGS. 106 and 107, the cushion may have a flap or thin portion 290 around its perimeter that interfaces or otherwise abuts the front plate 21. The flap 290 may be pressure activated i.e. when air is delivered under pressure into the mask, the flap 290 may be forced to abut the front plate 21 causing an air tight seal. If air is no longer delivered to the mask, the flap 290 may relax and permit air from atmosphere into the mask via a gap 291 created between the flap 290 and the front plate 21.

Patient Interface Systems—Materials

Figure 102:
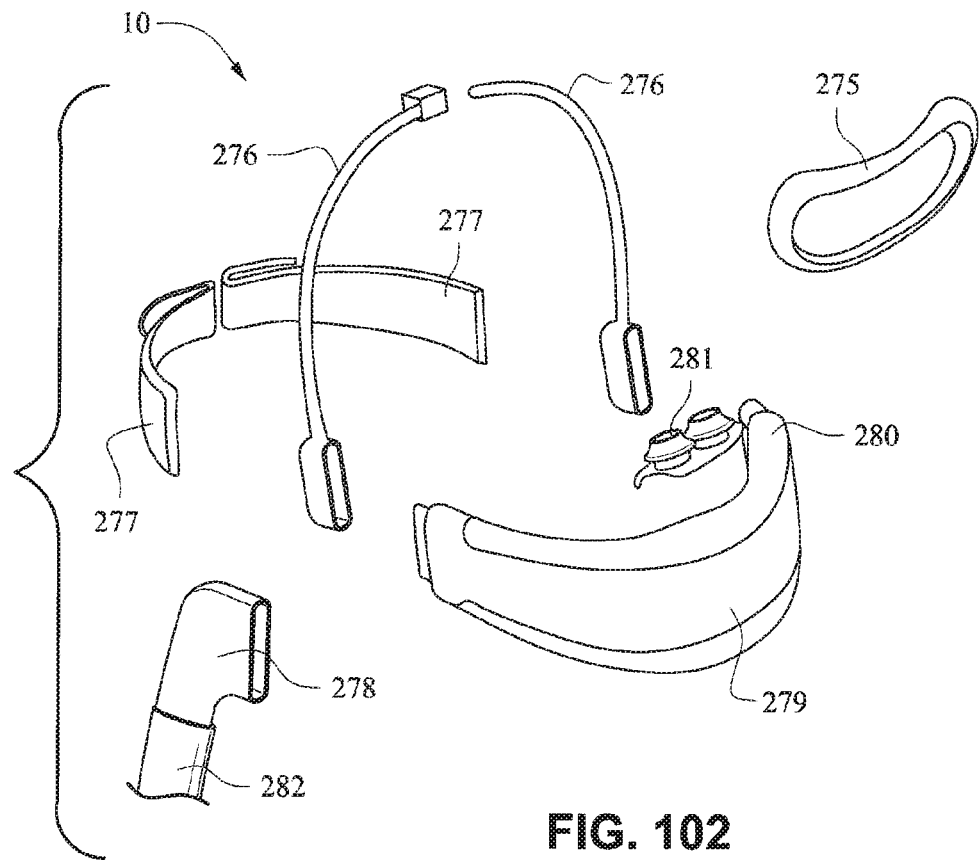
FIG. 102 is an exploded assembly view of a patient interface system according to another example embodiment of the present technology.

Referring to FIG. 102, a patient interface system 10 may comprise a polyester front plate or window 279 having a TPE "macro" seal 280 and a low durometer nasal seal 281 comprising pillows, or a seal as disclosed in WO 2010/139014 A1, the entire contents of which are incorporated herein by reference. A foam "micro" seal 275 may be attached to the seal 280. A TPE or TPU headgear 276 may be provided to position the patient interface system on the patient's head. Elastic webbing or ultrasonic die cut spacer fabric 277 may be provided. A tube connect 278 may be connected to a textile sock 282.

Patient Interface Systems—Headgear Strap and Tube Attachment

Figure 111:
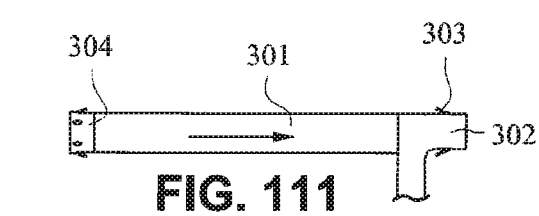
FIG. 111 is a schematic illustration of a strap, for example a rear strap, of a patient interface positioning system (e.g. headgear) according to another example embodiment of the present technology.
Figure 112:
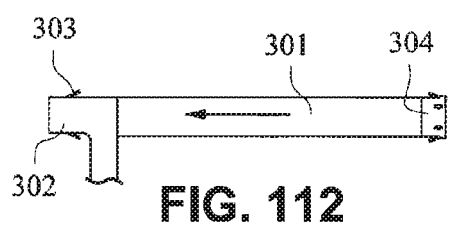
FIG. 112 is a schematic illustration of a strap, for example a rear strap, of a patient interface positioning system (e.g. headgear) according to another example embodiment of the present technology.

Referring to FIGS. 109-112, a headgear strap, e.g. a lower headgear strap that is positioned under the patient's ears and loops through a slot in the crown strap, may be connected to an air delivery tube 298. The air delivery tube 298 may connect to an end of the headgear strap 297, with gases being delivered through the headgear clip 299. The clips 299, 300 may interface with the front plate. As shown in FIGS. 111 and 112, the headgear strap 301 may be configured to deliver gases through an air delivery tube 302 and the clips 303, 304 may be formed in such a way that the strap 301 can be oriented either left (FIG. 111) to right or right to left (FIG. 112).

Patient Interface Structure—Patient Interface Positioning System Connection

Figure 114:
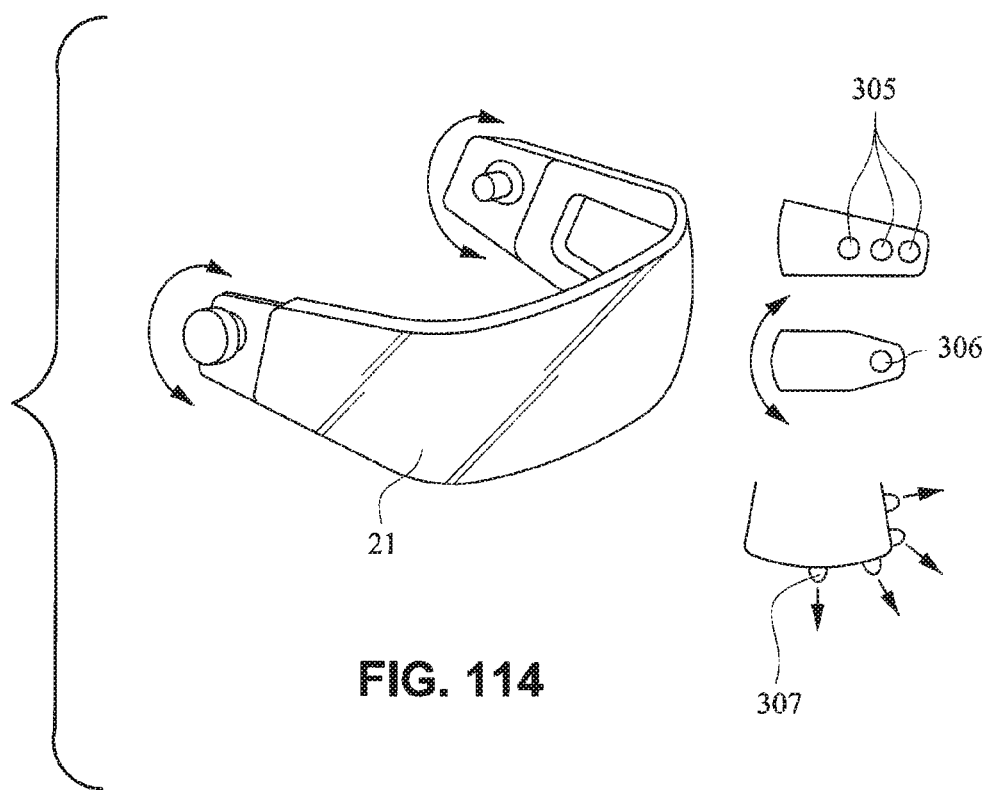
FIG. 114 is a schematic illustration of a patient interface system rotatably connectable to a patient interface positioning system according to an example embodiment of the present technology.

Referring to FIG. 114, the front plate 21 may include a plurality of attachment locations 305 for the patient interface positioning system, e.g. headgear, and/or a rotatable attachment location 306 that provides adjustment of the angle between the patient interface structure, e.g. mask, and the patient interface positioning system, e.g. headgear. The attachment locations may be in the form of rings 307.

Patient Interface Structure—Fascia

The fascia, frame or lens portion may comprise a fixed elbow connection, the elbow connection directed horizontally. Such an arrangement can be seen in, for example, FIG. 99. The fascia be structured and arranged to be flipped or rotated, such that the direction of the elbow may be changed from pointing to the left, for example, to pointing to the right. This means that the fascia may be symmetrical.

While the technology has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask system to treat sleep disordered breathing by providing pressurized air to a patient using components dimensioned to be unobtrusive, the mask system comprising:
a patient interface adapted to receive pressurized air from an air delivery conduit and contemporaneously provide the pressurized air to a nose of the patient and a mouth of the patient, the patient interface including:
a cushion to contact a face of the patient when the mask system is worn by the patient, the cushion including:
a mouth cushion portion shaped to seal (i) below the mouth of the patient between a lower lip of the patient and a chin of the patient, and (ii) above the mouth of the patient between an upper lip of the patient and nares of the patient, when the mask system is worn by the patient, the mouth cushion portion defining a mouth aperture shaped to receive the mouth of the patient, and
a nose cushion portion shaped to seal around the nares of the patient without contacting a bridge of the nose of the patient when the mask system is worn by the patient, the nose cushion portion defining a nose aperture shaped to provide the pressurized air to both nares of the patient, a height of the nose aperture measured between the upper lip of the patient and a tip of the nose of the patient being about 5-15 mm; and
a frame that connects to the cushion at a non-face-contacting portion of the cushion, the frame having greater rigidity than the cushion.

2. The mask system of claim 1, wherein the height of the nose aperture is measured at a center of the nose aperture.

3. The mask system of claim 1, wherein:
wherein the height of the nose aperture is about 7-12 mm;
the nose cushion portion includes a nose sealing wall;
an inner edge of the nose sealing wall defines the nose aperture; and
the nose aperture is shaped so that:
(i) side portions of the inner edge of the nose sealing wall sweep closer towards the upper lip of the patient than a center portion of the inner edge of the nose sealing wall that is between the side portions of the inner edge of the nose sealing wall when the mask system is worn by the patient, and
(ii) the center portion of the inner edge of the nose sealing wall is arranged further away from the upper lip of the patient than the side portions of the inner edge of the nose sealing wall edge when the mask system is worn by the patient.

4. The mask system of claim 1, wherein:
wherein the height of the nose aperture is about 7-12 mm; and
the nose cushion portion includes a nose sealing wall that is arranged to contact the face of the patient when the mask system is worn by the patient, the nose sealing wall defining the nose aperture.

5. The mask system of claim 4, wherein the nose cushion portion has a dual wall construction that includes (i) the nose sealing wall, and (ii) a nose supporting wall that is arranged between the nose sealing wall and a center region of the breathing chamber.

6. The mask system of claim 5, wherein a height of the mouth aperture is about 25-35 mm measured at a center of the mouth aperture, when the mask system is worn by the patient and viewed from in front of the patient.

7. The mask system of claim 6, wherein the height of the mouth aperture is about 25-30 mm.

8. The mask system of claim 6, wherein:
a left height of the mouth aperture measured left of the center of the mouth aperture is greater than the height of the mouth aperture measured at the center of the mouth aperture; and
a right height of the mouth aperture measured right of the center of the mouth aperture is greater than the height of the mouth aperture measured at the center of the mouth aperture.

9. The mask system of claim 6, wherein the mouth cushion portion includes a mouth sealing wall, wherein an inner edge of the mouth sealing wall defines the mouth aperture.

10. The mask system of claim 9, wherein a thickness of the mouth sealing wall is about 0.3-0.7 mm.

11. The mask system of claim 9, wherein a thickness of the mouth sealing wall is about 0.3-1.5 mm.

12. The mask system of claim 11, wherein a thickness of the nose sealing wall is about 0.3-0.7 mm.

13. The mask system of claim 11, wherein a thickness of the nose sealing wall is about 0.3-1.5 mm.

14. The mask system of claim 13, wherein:
a total height of the cushion measured between the chin of the patient and the nose of the patient when the mask system is worn by the patient is about 60-75 mm; and
a total width of the cushion measured between ears of the patient is about 90-105 mm when the mask system is worn by patient.

15. The mask system of claim 1, wherein a total height of the cushion measured between the chin of the patient and the nose of the patient, when the mask system is worn by the patient, is about 60-75 mm.

16. The mask system of claim 15, wherein a total width of the cushion measured between ears of the patient, when the mask system is worn by the patient, is about 90-105 mm.

17. The mask system of claim 16, wherein a height of the mouth aperture measured between the chin of the patient and the nose of the patient, when the mask system is worn by the patient, is about 25-35 mm measured at a center of the mouth aperture.

18. The mask system of claim 1, wherein the frame includes means for connecting with headgear.

19. The mask system of claim 18, wherein:
the nose cushion portion includes means for contacting sides of the nose of the patient; and
the nose cushion portion includes means for sealing with an underside of the nose of the patient.

20. The mask system of claim 19, wherein:
the nose cushion portion includes means for supporting a nose sealing wall; and
the mouth cushion portion includes means for supporting a mouth sealing wall.

21. The mask system of claim 20, wherein the patient interface includes means for connecting with the air delivery conduit.

22. The mask system of claim 1, wherein an entire perimeter of the nose aperture is defined by an inner edge of a nose sealing wall of the nose cushion portion.

23. The mask system of claim 1, wherein the nose cushion portion includes a nose sealing wall that is adapted to engage nasal flares of the patient when the mask system is worn by the patient.

24. The mask system of claim 23, wherein:
the cushion includes a cradle wall that separates the nose aperture from the mouth aperture, the cradle wall being shaped to contact the face of the patient between the upper lip of the patient and the nares of the patient; and
the cradle wall hangs below a top of the frame and is structured so that the tip of the nose of the patient rests below the top of the frame, when the mask system is worn by the patient and the patient interface is viewed from in front of the patient.

25. The mask system of claim 24, wherein the cradle wall that separates the nose aperture from the mouth aperture forms a continuous sealing surface that is shaped to provide part of the seal that the nose cushion portion is shaped to form and part of the seal that the mouth cushion portion is shaped to form.

26. The mask system of claim 25, wherein the cradle wall forms the continuous sealing surface by lacking definition between the nose aperture and the mouth aperture.

27. A mask system to treat sleep disordered breathing by providing pressurized air to a patient using components dimensioned to be unobtrusive, the mask system comprising:
a patient interface adapted to receive pressurized air from an air delivery conduit and contemporaneously provide the pressurized air to a nose of the patient and a mouth of the patient, the patient interface including:
a cushion to contact a face of the patient when the mask system is worn by the patient, the cushion including:
a mouth cushion portion shaped to seal (i) below the mouth of the patient between a lower lip of the patient and a chin of the patient, and (ii) above the mouth of the patient between an upper lip of the patient and nares of the patient, when the mask system is worn by the patient, the mouth cushion portion defining a mouth aperture shaped to receive the mouth of the patient, and
a nose cushion portion shaped to seal around the nares of the patient when the mask system is worn by the patient, the nose cushion portion defining a nose aperture shaped to provide the pressurized air to both nares of the patient, a height of the nose aperture measured between the upper lip of the patient and a tip of the nose of the patient being about 5-15 mm, wherein:
(i) the cushion is shaped to not contact a bridge of the nose of the patient, when the mask system is worn by the patient,
(ii) the mouth cushion portion and the nose cushion portion are integrally formed from silicone,
(iii) a total height of the cushion measured between the chin of the patient and the nose of the patient, when the mask system is worn by the patient, is about 60-75 mm,
(iv) a total width of the cushion measured between ears of the patient, when the mask system is worn by the patient, is about 90-105 mm, and
(v) a height of the mouth aperture measured between the chin of the patient and the nose of the patient, when the mask system is worn by the patient, is about 25-35 mm measured at a center of the mouth aperture; and
a frame that connects to the cushion at a non-face-contacting portion of the cushion, the frame having greater rigidity than the cushion.

28. A mask system to treat sleep disordered breathing by providing pressurized air to a patient using components dimensioned to be unobtrusive, the mask system comprising:
a patient interface adapted to receive pressurized air from an air delivery conduit and contemporaneously provide the pressurized air to a nose of the patient and a mouth of the patient, the patient interface including:
a cushion to contact a face of the patient when the mask system is worn by the patient, the cushion including:
a mouth cushion portion shaped to seal (i) below the mouth of the patient between a lower lip of the patient and a chin of the patient, and (ii) above the mouth of the patient between an upper lip of the patient and nares of the patient, when the mask system is worn by the patient, the mouth cushion portion defining a mouth aperture shaped to receive the mouth of the patient, and
a nose cushion portion shaped to seal around the nares of the patient without contacting a bridge of the nose of the patient when the mask system is worn by the patient, the nose cushion portion defining a nose aperture shaped to provide the pressurized air to both nares of the patient, a height of the nose aperture measured between the upper lip of the patient and a tip of the nose of the patient being about 5-15 mm, wherein:
(i) the nose cushion portion includes a sealing wall that is adapted to engage nasal flares of the patient, when the mask system is worn by the patient,
(ii) an entire perimeter of the nose aperture is defined by an inner edge of the sealing wall of the nose cushion portion, and
(iii) the cushion includes a cradle wall that separates the nose aperture from the mouth aperture, the cradle wall being shaped to contact a face of the patient between the upper lip of the patient and the nares of the patient; and
a frame that connects to the cushion at a non-face-contacting portion of the cushion, the frame having greater rigidity than the cushion, wherein the cradle wall hangs below a top of the frame and is structured so that the tip of the nose of the patient rests below the top of the frame, when the mask system is worn by the patient and the patient interface is viewed from in front of the patient.

29. The mask system of claim 28, wherein the cradle wall that separates the nose aperture from the mouth aperture forms a continuous sealing surface that is shaped to provide part of the seal that the nose cushion portion is shaped to form and part of the seal that the mouth cushion portion is shaped to form.

* * * * *